(12) United States Patent
Addington et al.

(10) Patent No.: US 8,597,184 B2
(45) Date of Patent: *Dec. 3, 2013

(54) TECHNIQUES FOR EVALUATING URINARY STRESS INCONTINENCE AND USE OF INVOLUNTARY REFLEX COUGH AS A MEDICAL DIAGNOSTIC TOOL

(75) Inventors: W. Robert Addington, Melbourne Beach, FL (US); Stuart P. Miller, Indialantic, FL (US); Michael M. Phelipa, Melbourne, FL (US); Mary W. Briganti, Melbourne, FL (US); Robert E. Stephens, Parkville, MO (US)

(73) Assignee: Pneumoflex Systems, LLC, Melbourne, FL (US)

( * ) Notice: Subject to any disclaimer, the term of this patent is extended or adjusted under 35 U.S.C. 154(b) by 755 days.

This patent is subject to a terminal disclaimer.

(21) Appl. No.: 12/878,257

(22) Filed: Sep. 9, 2010

(65) Prior Publication Data

US 2011/0040157 A1    Feb. 17, 2011

Related U.S. Application Data

(63) Continuation-in-part of application No. 12/643,251, filed on Dec. 21, 2009, which is a continuation-in-part of application No. 11/550,125, filed on Oct. 17, 2006.

(60) Provisional application No. 61/296,304, filed on Jan. 19, 2010, provisional application No. 61/311,882, filed on Mar. 9, 2010, provisional application No. 61/356,895, filed on Jun. 21, 2010, provisional application No. 61/139,649, filed on Dec. 22, 2008, provisional application No. 61/244,167, filed on Sep. 21, 2009, provisional application No. 60/727,740, filed on Oct. 18, 2005, provisional application No. 60/752,351, filed on Dec. 21, 2005.

(51) Int. Cl.
*A61B 5/00*    (2006.01)

(52) U.S. Cl.
USPC ............................ 600/301; 600/546; 600/561

(58) Field of Classification Search
None
See application file for complete search history.

(56) References Cited

U.S. PATENT DOCUMENTS 2,337,373 A    12/1943    Chernack ........................ 138/53
(Continued)

FOREIGN PATENT DOCUMENTS

EP    0 608 593    8/1994    ............... A61B 5/20
(Continued)

OTHER PUBLICATIONS

Bolster et al. "*Neurogenesis of cough, other airway defensive behaviors and breathing: A holarchical system?*" Jan. 16, 2006 www.sciencedirect.com.
(Continued)

*Primary Examiner* — Bill Thomson
*Assistant Examiner* — Davin K Sands
(74) *Attorney, Agent, or Firm* — Allen, Dyer, Doppelt, Milbrath & Gilchrist, P.A.

(57) ABSTRACT

A system permits diagnosis of a patient for a physiological abnormality while protecting their airway. An esophageal airway protection device comprises an elongate device body having a distal end for insertion into the stomach through the esophagus and a proximal end. The device includes a main lumen extending the length of the device and an inflatable esophageal cuff carried by the device body mid-esophagus. Emesis and/or reflux is blocked from passing out of the stomach past the esophageal cuff positioned mid-esophagus when it is inflated to protect a patient's airway during an involuntary cough event. At least one electromyogram (EMG) pad is configured to obtain an EMG from an involuntary cough activated paraspinal muscles. A processing device is configured to receive the EMG and process the EMG to determine a physiological abnormality.

16 Claims, 65 Drawing Sheets

(56) References Cited

U.S. PATENT DOCUMENTS

| | | | |
|---|---|---|---|
| 2,918,893 A | 12/1959 | Norton | 116/114 |
| 3,055,371 A | 9/1962 | Kulick | 123/325 |
| 3,286,713 A | 11/1966 | Kurtz et al. | |
| 3,373,735 A | 3/1968 | Gallagher | |
| 3,426,758 A | 2/1969 | Harautuneian | 128/349 |
| 3,895,629 A | 7/1975 | Snyder | 128/171 |
| 4,080,970 A | 3/1978 | Miller | 128/350 |
| 4,090,518 A | 5/1978 | Elam | 128/349 |
| 4,114,625 A | 9/1978 | Onat | 128/348 |
| 4,214,593 A | 7/1980 | Imbruce et al. | 128/748 |
| 4,221,215 A | 9/1980 | Mandelbaum | 128/155 |
| 4,230,108 A | 10/1980 | Young | 128/207.15 |
| 4,327,731 A | 5/1982 | Powell | 128/287 |
| 4,613,323 A | 9/1986 | Norton et al. | 604/43 |
| 4,632,119 A | 12/1986 | Reichstein | 128/632 |
| 4,634,435 A | 1/1987 | Ingraham | 604/268 |
| 4,672,960 A | 6/1987 | Frankel | 128/200.26 |
| 4,676,778 A | 6/1987 | Nelson, Jr. | 604/45 |
| 4,735,607 A | 4/1988 | Keith, Jr. | 604/54 |
| 4,752,286 A | 6/1988 | Okada | 604/96 |
| 4,790,328 A | 12/1988 | Young | 600/561 |
| 4,973,314 A | 11/1990 | Garrett | 604/180 |
| 4,976,261 A | 12/1990 | Gluck et al. | 128/207.15 |
| 4,981,470 A | 1/1991 | Bombeck, IV | 128/635 |
| 5,146,916 A * | 9/1992 | Catalani | 128/207.14 |
| 5,389,074 A | 2/1995 | Parker et al. | 604/96 |
| 5,417,664 A | 5/1995 | Felix et al. | 604/129 |
| 5,433,216 A | 7/1995 | Sugrue et al. | 128/778 |
| 5,462,539 A | 10/1995 | Herman et al. | 604/385.1 |
| 5,819,733 A | 10/1998 | Bertram | 128/207.15 |
| 5,862,804 A | 1/1999 | Ketchum | 128/885 |
| 5,904,656 A | 5/1999 | Addington et al. | 600/529 |
| 5,904,666 A | 5/1999 | Dedecker et al. | 604/65 |
| 5,916,153 A | 6/1999 | Rhea, Jr. | 600/310 |
| 5,947,943 A | 9/1999 | Lee | 604/361 |
| 5,980,507 A | 11/1999 | Fassuliotis et al. | 604/540 |
| 6,004,268 A | 12/1999 | Addington et al. | 600/300 |
| 6,056,699 A | 5/2000 | Sohn et al. | 600/561 |
| 6,267,729 B1 | 7/2001 | Addington et al. | 604/890.1 |
| 6,267,792 B1 | 7/2001 | Nagamiya et al. | 48/197 |
| 6,284,942 B1 | 9/2001 | Rabin | 604/361 |
| 6,302,917 B1 | 10/2001 | Dua et al. | 623/23.68 |
| 6,561,195 B2 | 5/2003 | Addington et al. | 128/898 |
| 6,568,397 B1 | 5/2003 | Addington et al. | 128/897 |
| 6,581,605 B2 | 6/2003 | Addington et al. | 128/897 |
| 6,602,243 B2 | 8/2003 | Noda | 604/544 |
| 6,626,169 B2 | 9/2003 | Gaitini | 128/200.14 |
| 6,648,906 B2 | 11/2003 | Lasheras et al. | 607/105 |
| 6,655,376 B2 | 12/2003 | Addington et al. | 128/200.24 |
| 6,679,249 B2 | 1/2004 | Addington et al. | 128/200.14 |
| 6,723,053 B2 | 4/2004 | Ackerman et al. | 600/486 |
| 6,863,664 B2 | 3/2005 | Wada et al. | 604/385.17 |
| 6,918,924 B2 | 7/2005 | Lasheras et al. | 607/105 |
| 6,958,052 B1 | 10/2005 | Charlton | 604/102.02 |
| 7,013,899 B2 | 3/2006 | Alfery et al. | 128/207.18 |
| 7,040,322 B2 | 5/2006 | Fortuna | 128/207.15 |
| 7,140,370 B2 | 11/2006 | Tresnak et al. | 128/207.14 |
| 7,311,696 B2 | 12/2007 | Christon et al. | 604/385.01 |
| 7,322,359 B2 | 1/2008 | Ketchum | 128/886 |
| 7,332,642 B2 | 2/2008 | Liu | 604/361 |
| 7,343,915 B2 | 3/2008 | Addington et al. | 128/203.12 |
| 7,381,190 B2 | 6/2008 | Sugrue et al. | 600/561 |
| 7,507,239 B2 | 3/2009 | Shadduck | 606/41 |
| 7,761,169 B2 | 7/2010 | Zelickson et al. | 606/27 |
| 7,762,261 B1 | 7/2010 | Fortuna | 128/207.14 |
| 7,794,425 B2 | 9/2010 | Gobel | 604/101.05 |
| 2001/0050086 A1 | 12/2001 | Addington et al. | 128/898 |
| 2002/0049425 A1 | 4/2002 | Mosel et al. | 604/544 |
| 2002/0077680 A1 | 6/2002 | Noda | 607/105 |
| 2002/0112731 A1 | 8/2002 | Ketchum | 128/866 |
| 2003/0028075 A1 | 2/2003 | Ulmsten et al. | 600/29 |
| 2003/0078553 A1 | 4/2003 | Wada et al. | 604/361 |
| 2003/0114809 A1 | 6/2003 | Gagliardi et al. | 604/361 |
| 2003/0114835 A1 | 6/2003 | Noda | 604/544 |
| 2004/0015100 A1 | 1/2004 | Schmidt | 600/561 |
| 2004/0116457 A1 | 6/2004 | Ishihara et al. | 514/290 |
| 2004/0133067 A1 | 7/2004 | Tracey | 600/29 |
| 2004/0172010 A1 | 9/2004 | Addington et al. | 604/890.1 |
| 2004/0181161 A1 * | 9/2004 | Addington et al. | 600/529 |
| 2004/0267336 A1 | 12/2004 | Morrison et al. | 607/99 |
| 2005/0038328 A1 | 2/2005 | Stoehrer et al. | 600/301 |
| 2005/0059900 A1 | 3/2005 | Berger et al. | 600/546 |
| 2005/0065450 A1 * | 3/2005 | Stuebe et al. | 600/547 |
| 2005/0265978 A1 * | 12/2005 | Chancellor et al. | 424/93.7 |
| 2007/0123793 A1 | 5/2007 | Addington et al. | 600/546 |
| 2007/0225576 A1 | 9/2007 | Brown et al. | 600/301 |
| 2008/0077043 A1 * | 3/2008 | Malbrain et al. | 600/547 |
| 2008/0208151 A1 | 8/2008 | Zacharias et al. | 604/361 |
| 2008/0255529 A1 | 10/2008 | Christon et al. | 604/361 |
| 2008/0255530 A1 | 10/2008 | Christon et al. | 604/361 |
| 2008/0262454 A1 | 10/2008 | Christon et al. | 604/361 |
| 2009/0062771 A1 | 3/2009 | Tarola et al. | 604/516 |
| 2009/0125002 A1 | 5/2009 | Totz | 604/528 |
| 2010/0163023 A1 | 7/2010 | Singh | 128/200.26 |
| 2010/0224186 A1 | 9/2010 | Uesigi | 128/200.26 |

FOREIGN PATENT DOCUMENTS

| | | | | |
|---|---|---|---|---|
| EP | 0 694 284 | | 1/1996 | A61B 5/0215 |
| WO | 99/53837 | | 10/1999 | A61B 5/08 |
| WO | 03/092495 | | 11/2003 | A61B 5/05 |
| WO | 2004/073516 | | 9/2004 | A61B 5/08 |
| WO | 2006/105283 | | 10/2006 | A61B 1/12 |
| WO | WO2007018963 | | 2/2007 | A61B 5/03 |
| WO | 2007/079271 | | 7/2007 | A61B 5/03 |
| WO | 2007/081626 | | 7/2007 | A61B 5/100 |
| WO | WO 2007079271 | A2 * | 7/2007 | A61B 5/03 |
| WO | WO 2007081626 | A2 * | 7/2007 | A61B 5/07 |
| WO | 2008/094771 | | 8/2008 | A61B 10/00 |

OTHER PUBLICATIONS

DeBacker "*Abdominal compartment syndrome*" http://ccforum.com. Sep. 30, 1999.

Dziewas et al. *Pneumonia in acute stroke patients fed by nasogastric tube* www.jnnp.com Sep. 10, 2003.

Irwin, Richard "*Chronic Cough Due to Gastroesophageal Reflux Disease: ACCP Evidence-Based Clinical Practice Guidelines*" http://chestjournal.chestpubs.org/content/129/1_supII/80S.full.html.

Irwin et al. "The Cough Reflex and Its Relation to Gastroesophageal Reflux" *Am J Med*. 2000;108(4A): 73S-78S.

Handa et al. "*Federal Guidelines for the Management of Urinary Incontinence in the United States: Which Patients Should Undergo Urodynamic Testing?*" Int. Urogynecol J (1995) 6:198-203.

Jakus et al. "*Brainstem Areas Involved in the Aspiration Reflex: c-Fos Study in Anesthetized Cats*" Physiol. Res. 53: 703-717, 2004.

Poliacek et al. "*Cough, Expiration and Aspiration Reflexes following Kainic Acid Lesions to the Pontine Respiratory Group in Anesthetized Cats*" Physiol. Res. 53: 155-163, 2004.

Widdicombe et al. "*Supramedullary influences on cough*" Respiratory Physiology Neurobiology 152 (2006) 320-328.

Lasserson et al., "*Differences in Motor Activation of Voluntary and Reflex Cough in Humans*," Thorax, Aug. 2006; 61(8):699-705. Epub, Apr. 6, 2006, Abstract Only, 2 pp.

WD. Man et al., "Cough Gastric Pressure and Maximum Expiratory Mouth Pressure in Humans", American Journal of Respiratory and Critical Care Medicine, vol. 168, 2003, 4 pages.

F. Lavorini et al., "Fog-Induced Cough with Impaired Respiratory Sensation in Cogenital Central Hypoventilation Syndrome", Am J Respir Crit Care Med., Oct. 15, 2007; 176(8):825-32. Epub Aug. 2007.

Cadiere et al. "*Antireflux Transoral Incisionless Fundoplication Using EsophyX: 12-Month Results of a Prospective Multicenter Study*" World J Surg (2008) 32:1676-1688.

Marino et al. "*Induction of Lower Esophageal Sphincter (LES) Dysfunction during Use of the Negative Pressure Body Ventilator*" The American Journal of Gastroenterology vol. 83, No. 12, 1988.

"GERD" http://www.endogartricsolutions.com/aboutGERD_for-surgeons.htm.

Jones et al. "*Mechanisms of Pelvic Floor Muscle Function and the Effect on the Urethra during a Cough*" www.sciencedirect.com.

(56) References Cited

OTHER PUBLICATIONS

Chang et al. "*An objective study of acid reflux and cough in children using an ambulatory pHmetry-cough logger*"http://adc.bmj.com/cgi/reprintform.
Mutolo et al. "*Depression of the cough reflex by microinjectins of antitussive agents into the caudal ventral respiratory group of the rabbit*" J Appl Physiol (Jul. 22, 2010). Doi:10.1152/japplphysiol.00406.2010.
Yapici et al. "*The role of coughing as a gastroesophageal-reflux provoking maneuver: the scintigraphical evaluation*" DOI: 10.1097/MNM.Ob013e3283298f90.
Vizel et al. "*Validation of an ambulatory cough detection and counting application using voluntary cough under different conditions*" Http://www.coughjournal.com/content/6/1/3.
Ryan et al. "*Cough reflex sensitivity improves with speech language pathology management of refractory chronic cough*"http://www.coughhournal.com/content/6/1/5.
Smith et al. "*Spatial and Functional Architecture of the a mammalian Brain Stem Respiratory Network: A Hierarchy of Three Oscillatory Mechanisms*"J Neurophysiol 98: 3370-3387, 2007.
Rybak et al. "*Spatial organization and state-dependent mechanisms for respiratory rhythm and pattern generation*" Prog Brain Res. 2007: 165: 201-220.
Hernadez et al "*Anatomic-manometric correlation of the upper esophageal sphincter: a concurrent US and manometry study*" www.giejournal.org.
Kocjancic et al. "*Adjustable Continence Therapy for Severe Intrinsic Sphincter Deficiency and Recurrent Female Stress Urinary Incontinence: Long-Term Experience*" wwwljurology.com vol. 184, 1017-1021. Sep. 2010.
Canning et al. "*An essential component to brainstem cough gating identified in anesthetized guinea pigs*" The FASEB Journal article fj.09-151068.
Abdala et al. "*Multiple Pontomedullary mechanisms of respiratory rhythmogenesis*" Respiratory Physiology & Neurobiology 168 (2009) 19-25.
Vizel et al. "*Validation of an ambulatory cough detection and counting application using voluntary cough under different conditions*" http://www.coughjornal.com/content/6/1/3.
Satou et al. "*Gastroesophageal Reflux during Entemal Feeding in Stroke Patients: A 14-hour Esophageal pH-monitoring Study*" Journal of Stroke and Cerebrovascular Diseases.
DeLancey, John *Why Do Women have Stress Urinary Incontinence?* Neurourology and Urodynamics 29:S13-S17 (2010).
Douzinal et al. "*Reasons of PEG failure to eliminate gastroesophageal reflux in mechanically ventilated patients*" wjg.whgnet.com doi:10.3748/wjg.15.5455.
Kuribayashi et al. "*Terminating motor events for TLESR are influenced by the presence and distribution of reluxate*" AM J Physiol Gastrointeres Liver Physiol 297: G71-G75 2009.
Marik, PE "*Aspiration syndromes: aspiration pneumonia and pneumonitis*" Hop PRact (minneap) Feb. 2010; 38(1): 35-42. Abstract only.
Hurt et al. *Gastric residual volumes in critical illness: what do they really mean?* Crit Care Clin. Jul. 2010; 26 (3): 481-90, viii-ix. Abstract only.
Voorham-van der et al. "*Diganotic investigation of the pelvic floor*": J Sex Med. Apr. 2008; 5 (4): 864-71. Epub Jan. 21, 2008. Abstract only.
Nicolau et al. "*Endoluminal fundoplication (ELF) with EsophyX2 for gastroesophageal reflux disease (GERD)*" Chirurgia (Bucur). Jul.-Aug. 2009; 104(4):381-7. Abstract only.
Turker et al. "*The presencer of transurethral cystometry catheter and type of stress test affect the measurement of abdominal leak point pressure (ALPP) in women with stress urinary incontinence*" Neurourol Urodyn. Apr. 2010; 29(4): 536-9. Abstract only.
"*Urinary Incontinence in Women*" American Family Physician: American Family Physician vol. 62, No. 11 Dec. 1, 2000.
"*Exercising Your Pelvic Muscles*" American Family Physician: American Family Physician vol. 62, No. 11 Dec. 1, 2000.

Azpiroz et al. "*Anorectal Functional Testing: Review of Collective Experience*" PMID: 11866256; Am. J. Gastroenterol. Feb. 2002; 97(2)L 2320-240. (Abstract Only).
Bolster et al. "*Responses of the Anterolateral Abdominal Muscles During Cough and Expiratory Threshold Loading in the Cat*" Journal of Applied Physiology 88: 1207-1214, 2000.
Brown et al. "*Prevalence of Urinary Incontinence and Associated Risk Factors in Postmenopausal Women*" Obstetrics & Gynecology: 1999: 94: 66-70.
Cormier et al., "*Diagnosis of Female Bladder Outlet Obstruction and Relevance of the Parameter Area Under the Curve of Detrusor Pressure During Voiding: Preliminary Results*," Journal of Urology, May 2002, vol. 167, pp. 2083-2087.
Addington et al. "Intra-abdominal Pressures During Voluntary and Reflex Cough" *Cough*: vol. 4, 2, Apr. 30, 2008; pp. 1-9.
Deffieux et al. "Pelvic Floor Muscle Activity during Coughing: Altered Pattern in Women with Stress Urinary Incontinence" *ScienceDirect: Urology* vol. 70. Issue 3; Sep. 2007, pp. 443-447.
Deffieux et al."Sacral Reflexes and Urinary Incontinence in Women: New Concepts" *ScienceDirect; Annals of Physical and Rehabilitation Medicine*; vol. 52, Issue 3. Apr. 2009, pp. 256-268.
Steier et al. "The Value of Multiple Tests of Respiratory Muscle Strength" *Thorax*, Jun. 8, 2007, Epub, Abstract Only, 2 pages.
Vovk et al., "Capsaicin Exposure Elicits Complex Airway Defensive Motor Patterns in Normal Humans in a Concentration-Dependent Manner" *Pulm Pharmacol Ther*. 2007; 20(4):423-32, Epub, Dec. 12, 2006. Abstract Only, 2 pages.
Vernon et al. "*Measuring Cough Severity: Perspective Form the Literature and From Patients with Chronic Cough*" http://www.coughjournal, 2009.
Yuan, et al. "*Vibratory Perception and Female Stress Urinary Incontinence*" Science Direct: Journal of Urology Apr. 2, 2009.
Xie, et al. "*Alterations of Estrogen Receptor-a and -b in the Anterior Vaginal Wall of Women with Urinary Incontinence*" ScienceDirect: European Journal of Obstetrics & Gynecology and Reproductive Biology, vol. 134. Ossie 2. Pct/2007, pp. 254-258.
Zalm et al. "Diagnostic Investigation of the Pelvic Floor: a Helpful Tool in the Approach in Patients with Complaints of Micturition, Defecation, and/or Sexual Dysfunction" *J. Sex. Med*. Apr. 2008; 5(4): 864-71. Epub Jan. 21, 2008 (Abstract Only).
Shishido et al. "Influence of Pelvic Floor Muscle Contraction on the Profile of Vaginal Closure Pressure in Continent and Stress Urinary Incontinent Women" *ScienceDirect: Journal of Urology*; vol. 179. Issue 5 May 2008, pp. 1917-1922.
Trabucco, et al. "*Role of Proteoglycans in the Organization of Periurethral Connective Tissue in Women with Stress Urinary Incontinence*" ScienceDirect: Maturital; vol. 58, Issue 4, Dec. 20, 2007, pp. 395-405.
Bump et al. "*Cigarette Smoking and Pure Genuine Stress Incontinence of Urine: A Comparison of Risk Factors and Determinants Between Smokers and Nonsmokers*" Am. J. Obstet Gynecol. Feb. 1994; 170(2): 579-82. (Abstract Only).
Bump et al. "*Valsalva Leak Point Pressures in Women With Genuine Stress Incontinence: Reproducibility, Effect of Catheter Caliber, and Correlations With Other Measures of Urethral Resistance. Continence Program for Women Research Group*"Am. J. Obstet. Gynecol. Aug. 1995; 173(2):551-7. (Abstract Only).
Carry et al. "*Intra-abdominal Pressure*" Ann. Fr. Aneshth. Ranim. 1994; 13(3): 381-99. (Abstract Only).
Chang et al. "*Transrectal Sonographic Cystourethrography: Studies in Stress Urinary Incontinence*" Science Direct-Urology; vol. 36, Issue 6, Dec. 1990, pp. 488-492. (Abstract Only).
Chiara et al. "Expiratory Muscle Strength Training in Persons With Multiple Sclerosis Having Mild to Moderate Disability: Effect on Maximal Expiatory Pressure, Pulmonary Function, and Maximal Voluntary Cough" *Arch Phys Med REhabil*. vol. 87, Apr. 2006 pp. 468-473.
Ciofu et al. "*Contribution of VLPP (Valsalva Leak Point Pressure) in the Urodynamic Assessment*" Gynecol. Obstet. Fertil. Feb 2004; 32(2): 160-3. (Abstract Only).
Culligan et al. "*Urinary Incontinence in Women: Evaluation and Management*" American Family Physician, vol. 62 No. 11. Dec. 1, 2000.

(56) References Cited

OTHER PUBLICATIONS

Freestone et al."*Assessment of the Antitussive Efficacy of Codeine in Cough Associated with Common Cold*" PubMed: J. Pharm. Pharmacol. Oct. 1997; 49(10) 1045-1049. (Abstract Only).

Hammond et al. "*Assessment of aspiration risk in stroke patients with quantification of voluntary cough*" American Academy of Neurology. www.neurology.org 2001;56;502-506.

Hundley et al. "*A Multicentered Comparison of Measurements Obtained with Microtip and External Water Pressure Transducers*" PubMed: Int. Urogynecol. J. Pelvic Floor Dystfunct. Nov. 12, 2005: 1-7. (Abstract Only).

Kim et al. "*The Vesico-Urethral Pressuregram Analysis of Urethral Function Under Stress*" Science Direct; Journal of Biomechanics, vol. 30. Issue 1, Jan. 1997, pp. 19-25. (Abstract Only).

Kocjancic et al. "*Evaluation of Minimally Invasive Analysis System for Cough Leak Point Pressure Measurement*" PubMed: J. Uro. Sep. 2004; 172(3): 994-7. (Abstract Only).

Langdon et al. "*High Incidence of Respiratory Infections in 'Nil by Mouth' Tube-Fed Acute Ischemic Stroke Patients*" Neuroepidemiiology 2009; 32: 107-113.

Lin et al. "*Comparisons of Urodynamic Characteristics Between Female Patients with Overactive Bladder and Overactive Bladder Plus Stress Urinary Incontinence*" Science Direct: Urology vol. 64, Issue 5, Nov. 2004, pp. 945-949.

Majoros et al. "*Value of Testing the Abdominal Leak Point Pressure in the Differential Diagnosis of Urinary Stress Incontinence*" PubMed: Orv. Hetil. Nov. 23, 2003; 144(47): 2321-5. (Abstract Only).

Man et al., "Cough Gastric Pressure and Maximum Expiratory Mouth Pressure in Humans", Am. J. Respir. Crit. Care Med. Sep. 15, 2003;168(6):714-7. Epub Jul. 11, 2003.

Martin, et al. "Systematic review and evaluation of methods of assessing urinary incontinence" Health Technology Assessment, Feb. 2006. vol. 10, No. 6.

Matthys et al. "*Objectivation of the Effect of Antitussive Agents Using Tussometry in Patients with Chronic Cough*" PubMed: Schweiz Med Wochenschr. Mar. 2, 1985; 115(9): 307-11. (Abstract Only).

McEwan, Jr. et al. "*Change in Cough Reflex after Treatment with Enalapril and Ramipril*" PubMed: BMJ. Jul. 1, 1989; 299(6690): 13-6. (Abstract Only).

Miklos, Jr. et al. "*A Critical Appraisal of the Methods of Measuring Leak-Point Pressures in Women with Stress Incontinence*" PubMed: Obstet. Gynecol. Sep. 1995; 86(3): 349-52. (Abstract Only).

Phua, et al. "*Patients with Gastro-Oesophageal Reflux Disease and Cough have Impaired Laryngopharyngeal Mechanosensitivity*" PubMed: Thorax. Jun. 2005; 60(6): 488-91. (Abstract Only).

Quek, et al. "*Morbidity and Significant Bacteriuria after Urodynamic Studies*" Annals Academy of Medicine; Singapore 2004; 33:754-7.

Richter, et al. "Lower Urinary Tract Symptoms, Quality of Life and Pelvic Organ Prolapse: Irritative Bladder an Obstructive Voiding Symptoms in Women Planning to Undergo Abdominal Sacrocolpopexy for Advanced Pelvic Organ Prolapse" *ScienceDirect: Journal of Urology* vol. 178, issue 3, Sep. 1997, pp. 965-969.

Shaker, et al. "Vocal Cord Closure Pressure During Volitional Swallow and other Voluntary Tasks" *PubMed: Dysphagia*. Winter 2002; 17(1)L 13-8. (Abstract Only).

Steffen, et al. "Measurement of Pressure and Force as a Basis of the Postoperative Evaluation of Abdominal Wall Function" *PubMed: Z. Exp. Chir. Transplant. Kunstliche Organe*. 1987; 20(1): 44-9. (Abstract Only).

Swift et al. "Test-retest Reliability of the Cough Stress Test in the Evaluation of Urinary Incontinence" *Obstetrics and Gynecology*; vol. 94, No. 1, Jul. 1999; pp. 99-102.

Van Hengstum, et al. "Effect of Positive Expiratory Pressure Mask Physiotherapy (PEP) Versus Forced Expiration Technique 9FET/PD) on Regional Lung Clearance in Chronic Bronchitis" *PubMed: Eur. Erspir. J*. 1991; 4(6): 651-4. (Abstract Only).

Wall, et al. "Are Vaginal and Rectal Pressures Equivalent Approximations of One Another for the Purpose of Performing Subtracted Cystometry?" *PubMed: Obstet. Gynecol*. Apr. 1995; 85(4):488-93. (Abstract Only).

Cobb et al., "Normal Intraabdominal Pressure in Healthy Adults," Journal of Surgical Research, vol. 129, Feb. 18, 2005, pp. 231-235.

Upadya et al., "Predictors and Consequences of Pneumonia in Critically Ill Patients With Stroke," Journal of Critical Care, vol. 19, No. 1, Mar. 2004, pp. 16-22.

Chiumello et al. "*A validation study of a new nasogastric polyfunctional catheter*" Intensive Care Med. DOI 10.1007/s00134-011-2178-4. Published online Mar. 2, 2011.

* cited by examiner

VOLUNTARY COUGH

| SUBJECT | TEST ORDER | AUC | PEAK PRESSURE (CM OF WATER) | DURATION (SEC.) | NO. OF SPIKES | LEAK |
|---|---|---|---|---|---|---|
| SUBJECT #1 | VC 1ST | 92 | 87 | 3 | 2 | NO |
| SUBJECT #2 | VC 1ST | 290 | 167 | 6 | 2 | NO |
| SUBJECT #3 | RCT 1ST | 326 | 100 | 11 | 7 | NO |
| SUBJECT #4 | VC 1ST | 430 | 165 | 10 | 2 | NO |
| SUBJECT #5 | RCT 1ST | 612 | 211 | 7 | 5 | YES |
| SUBJECT #6 | RCT 1ST | 518 | 180 | 8 | 5 | YES |

FIG. 7A

INVOLUNTARY COUGH (REFLEX COUGH TEST)

| SUBJECT | TEST ORDER | AUC | PEAK PRESSURE (CM OF WATER) | DURATION (SEC.) | NO. OF SPIKES | LEAK |
|---|---|---|---|---|---|---|
| SUBJECT #1 | VC 1ST | 125 | 100 | 3 | 2 | YES |
| SUBJECT #2 | VC 1ST | 963 | 175 | 23 | 10 | NO |
| SUBJECT #3 | RCT 1ST | 1276 | 170 | 27 | 11 | NO |
| SUBJECT #4 | VC 1ST | 1575 | 139 | 41 | 9 | NO |
| SUBJECT #5 | RCT 1ST | 1428 | 174 | 26 | 16 | YES |
| SUBJECT #6 | RCT 1ST | 1148 | 194 | 16 | 14 | YES |

FIG. 7B

PAIRED SAMPLES STATISTICS

| | | MEAN | N | STD. DEVIATION | STD. ERROR MEAN |
|---|---|---|---|---|---|
| PAIR 1 | RCTAIAP | 50.739 | 168 | 19.662 | 1.517 |
| | VCTAIAP | 44.907 | 168 | 13.910 | 1.073 |

PAIRED SAMPLES CORRELATIONS

| | | N | CORRELATION | Sig. |
|---|---|---|---|---|
| PAIR 1 | RCTAIAP & VCTAIAP | 168 | .514 | .000 |

PAIRED SAMPLES TEST

| | | PAIRED DIFFERENCES | | | | | |
|---|---|---|---|---|---|---|---|
| | | | | | 95% CONFIDENCE INTERVAL OF THE DIFFERENCE | | |
| | | MEAN | STD. DEVIATION | STD. ERROR MEAN | LOWER | UPPER | t |
| PAIR 1 | RCTAIAP - VCTAIAP | 5.832 | 17.282 | 1.333 | 3.199 | 8.464 | 4.374 |

PAIRED SAMPLES TEST

| | | df | SIG. (2-TAILED) |
|---|---|---|---|
| PAIR 1 | RCTAIAP - VCTAIAP | 167 | .000 |

FIG. 11

PAIRED SAMPLES STATISTICS

| | | MEAN | N | STD. DEVIATION | STD. ERROR MEAN |
|---|---|---|---|---|---|
| PAIR 1 | RCTPIAP | 151.733 | 168 | 45.629 | 3.520 |
| | VCTPIAP | 128.937 | 168 | 37.856 | 2.921 |

PAIRED SAMPLES CORRELATIONS

| | | N | CORRELATION | Sig. |
|---|---|---|---|---|
| PAIR 1 | RCTPIAP & VCTPIAP | 168 | .630 | .000 |

PAIRED SAMPLES TEST

| | | PAIRED DIFFERENCES | | | | | |
|---|---|---|---|---|---|---|---|
| | | | | | 95% CONFIDENCE INTERVAL OF THE DIFFERENCE | | |
| | | MEAN | STD. DEVIATION | STD. ERROR MEAN | LOWER | UPPER | t |
| PAIR 1 | RCTPIAP - VCTPIAP | 22.796 | 36.603 | 2.824 | 17.221 | 28.371 | 8.072 |

PAIRED SAMPLES TEST

| | | df | SIG. (2-TAILED) |
|---|---|---|---|
| PAIR 1 | RCTPIAP - VCTPIAP | 167 | .000 |

FIG. 12

PAIRED SAMPLES STATISTICS

|  |  | MEAN | N | STD. DEVIATION | STD. ERROR MEAN |
|---|---|---|---|---|---|
| PAIR 1 | RCTAUC | 753.089 | 168 | 457.718 | 35.314 |
|  | VCTAUC | 512.101 | 168 | 298.110 | 23.000 |

PAIRED SAMPLES CORRELATIONS

|  |  | N | CORRELATION | Sig. |
|---|---|---|---|---|
| PAIR 1 | RCTAUC & VCTAUC | 168 | .289 | .000 |

PAIRED SAMPLES TEST

|  | PAIRED DIFFERENCES | | | | | t |
|---|---|---|---|---|---|---|
|  | MEAN | STD. DEVIATION | STD. ERROR MEAN | 95% CONFIDENCE INTERVAL OF THE DIFFERENCE | | |
|  |  |  |  | LOWER | UPPER | |
| PAIR 1 RCTAUC-VCTAUC | 240.988 | 468.567 | 36.151 | 169.617 | 312.359 | 6.666 |

PAIRED SAMPLES TEST

|  | df | SIG. (2-TAILED) |
|---|---|---|
| PAIR 1 RCTAUC-VCTAUC | 167 | .000 |

FIG. 13

SUMMARY OF SENSITIVITY, SPECIFICITY, PPV, NPV (PRIMARY ANALYSES)
EFFICACY POPULATION

| STATUS | VOLUNTARY COUGH (N=180) | REFLEX COUGH (N=179) | P-VALUE |
|---|---|---|---|
| SENSITIVITY [1] | | | |
| MILD SUI | 74/140 (53) | 110/139 (79) | <.0001 |
| | 35/65 (54) | 51/65 (78) | 0.0145 |
| MODERATE/SEVERE SUI | 39/75 (52) | 59/74 (80) | <.0001 |
| SPECIFICITY [2] | 38/40 (95) | 34/40 (85) | 0.0352 |
| 95% CI (VCT-IRCT): (-1.6, 21.6) | | | |
| POSITIVE PREDICTIVE VALUE [3] | 74/76 (97) | 110/116 (95) | |
| MILD SUI | 35/37 (95) | 51/57 (89) | |
| MODERATE/SEVERE SUI | 39/41 (95) | 59/65 (91) | |
| NEGATIVE PREDICTIVE VALUE [4] | 38/104 (37) | 34/63 (54) | |

[1] SENSITIVITY = TP/(TP+FN)
[2] SPECIFICITY = TN/(TN+FP)
[3] POSITIVE PREDICTIVE VALUE = TP/(TP+FP)
[4] NEGATIVE PREDICTIVE VALUE = TN/(TN+FN)
TN = TRUE NEGATIVE, TP = TRUE POSITIVE, FN = FALSE NEGATIVE, FP = FALSE POSITIVE.
FOR THE PRIMARY ANALYSES, LEAKAGE IS DEFINED AS A LEAK DURING A TEST WHILE IN THE SEMI-RECUMBENT POSITION.
NOTE: THE EFFICACY POPULATION IS DEFINED AS ALL SUBJECTS WHO ARE RANDOMIZED AND EXPOSED TO STUDY DRUG.
TO DETERMINE WHETHER OR NOT THERE IS A PROVOCATION EFFECT, GENERALIZED ESTIMATING EQUATIONS ASSUMING AN EXCHANGEABLE CORRELATION MATRIX, LOGIT LINK AND BINOMIAL DISTRIBUTION WITH FIXED EFFECTS FOR TEST (VCT VS. IRCT) AND PERIOD (1 VS. 2) WERE USED.

FIG. 17A

SUMMARY OF SENSITIVITY, SPECIFICITY, PPV, NPV (PRIMARY ANALYSES)
EFFICACY POPULATION - ADJUDICATED STRATA

| STATUS | VOLUNTARY COUGH (N=180) | REFLEX COUGH (N=179) | P-VALUE |
|---|---|---|---|
| SENSITIVITY [1] | | | |
| MILD SUI | 74/148 (51) | 115/147 (78) | <.0001 |
| | 36/73 (49) | 56/73 (77) | 0.0037 |
| MODERATE/SEVERE SUI | 39/75 (52) | 59/74 (80) | <.0001 |
| SPECIFICITY [2] | 31/32 (97) | 31/32 (97) | 1.0000 |
| 95% CI (VCT-IRCT): (0.0, 0.0) | | | |
| POSITIVE PREDICTIVE VALUE [3] | | | |
| MILD SUI | 75/76 (99) | 115/116 (99) | |
| | 36/37 (97) | 56/57 (98) | |
| MODERATE/SEVERE SUI | 39/40 (98) | 59/60 (98) | |
| NEGATIVE PREDICTIVE VALUE [4] | 31/104 (30) | 31/63 (49) | |

[1] SENSITIVITY = TP/(TP+FN)
[2] SPECIFICITY = TN/(TN+FP)
[3] POSITIVE PREDICTIVE VALUE = TP/(TP+FP)
[4] NEGATIVE PREDICTIVE VALUE = TN/(TN+FN)
TN = TRUE NEGATIVE, TP = TRUE POSITIVE, FN = FALSE NEGATIVE, FP = FALSE POSITIVE.
FOR THE PRIMARY ANALYSES, LEAKAGE IS DEFINED AS A LEAK DURING A TEST WHILE IN THE SEMI-RECUMBENT POSITION.
NOTE: THE EFFICACY POPULATION IS DEFINED AS ALL SUBJECTS WHO ARE RANDOMIZED AND EXPOSED TO STUDY DRUG.
TO DETERMINE WHETHER OR NOT THERE IS A PROVOCATION EFFECT, GENERALIZED ESTIMATING EQUATIONS ASSUMING AN EXCHANGEABLE CORRELATION MATRIX, LOGIT LINK AND BINOMIAL DISTRIBUTION WITH FIXED EFFECTS FOR TEST (VCT VS. IRCT) AND PERIOD (1 VS. 2) WERE USED.

FIG. 17B

SUMMARY OF SENSITIVITY, SPECIFICITY, PPV, NPV (PRIMARY ANALYSES)
PER-PROTOCOL POPULATION

| STATUS | VOLUNTARY COUGH (N=172) | REFLEX COUGH (N=171) | P-VALUE |
|---|---|---|---|
| SENSITIVITY [1] | | | |
| MILD SUI | 74/140 (53) | 110/139 (79) | <.0001 |
| | 35/65 (54) | 51/65 (78) | 0.0145 |
| MODERATE/SEVERE SUI | 39/75 (52) | 59/74 (80) | <.0001 |
| SPECIFICITY [2] | 31/32 (97) | 31/32 (97) | 1.0000 |
| 95% CI (VCT-IRCT): (0.0, 0.0) | | | |
| POSITIVE PREDICTIVE VALUE [3] | 74/75 (99) | 110/111 (99) | |
| MILD SUI | 35/36 (97) | 51/52 (98) | |
| MODERATE/SEVERE SUI | 39/40 (98) | 59/60 (98) | |
| NEGATIVE PREDICTIVE VALUE [4] | 31/97 (32) | 31/60 (52) | |

[1] SENSITIVITY = TP/(TP+FN)
[2] SPECIFICITY = TN/(TN+FP)
[3] POSITIVE PREDICTIVE VALUE = TP/(TP+FP)
[4] NEGATIVE PREDICTIVE VALUE = TN/(TN+FN)
TN = TRUE NEGATIVE, TP = TRUE POSITIVE, FN = FALSE NEGATIVE, FP = FALSE POSITIVE.
FOR THE PRIMARY ANALYSES, LEAKAGE IS DEFINED AS A LEAK DURING A TEST WHILE IN THE SEMI-RECUMBENT POSITION.
NOTE: THE PER-PROTOCOL POPULATION IS DEFINED AS ALL SUBJECTS WHO ARE RANDOMIZED, EXPOSED TO STUDY DRUG AND HAVE NO MAJOR PROTOCOL VIOLATIONS
TO DETERMINE WHETHER OR NOT THERE IS A PROVOCATION EFFECT, GENERALIZED ESTIMATING EQUATIONS ASSUMING AN EXCHANGEABLE CORRELATION MATRIX, LOGIT LINK AND BINOMIAL DISTRIBUTION WITH FIXED EFFECTS FOR TEST (VCT VS. IRCT) AND PERIOD (1 VS. 2) WERE USED.

FIG. 17C

CHI-SQUARED (2x2)

| OBSERVED FREQUENCIES | | | |
|---|---|---|---|
| | COLUMN VARIABLE | | |
| ROW VARIABLE | IRCT | VCT | TOTAL |
| EARLY LEAK | 42 | 13 | 55 |
| LATE LEAK | 76 | 58 | 134 |
| TOTAL | 118 | 71 | 189 |

CALCULATIONS
fo-fe 7.661376   -7.66138
-7.66138    7.661376

| EXPECTED FREQUENCIES | | | |
|---|---|---|---|
| | COLUMN VARIABLE | | |
| ROW VARIABLE | IRCT | VCT | TOTAL |
| EARLY LEAK | 34.33862 | 20.66138 | 55 |
| LATE LEAK | 83.66138 | 50.33862 | 134 |
| TOTAL | 118 | 71 | 189 |

(fo-fe)^2/fe 1.709349   2.840889
0.701598   1.166037

| DATA | |
|---|---|
| LEVEL OF SIGNIFICANCE | 0.05 |
| NUMBER OF ROWS | 2 |
| NUMBER OF COLUMNS | 2 |
| DEGREES OF FREEDOM | 1 |

| RESULTS | |
|---|---|
| CRITICAL VALUE | 3.8415 |
| CHI-SQUARE TEST STASTISTIC | 6.4179 |
| p-VALUE | 0.0113 |
| REJECT THE NULL HYPOTHESIS | |

EXPECTED FREQUENCY ASSUMPTION IS MET.

FISHER'S EXACT TEST

| | IRCT | VCT | TOTAL |
|---|---|---|---|
| EARLY LEAK | 42 | 13 | 55 |
| LATE LEAK | 76 | 58 | 134 |
| TOTAL | 118 | 71 | 189 | p-VALUE= 0.01307                    REJECT THE NULL HYPOTHESIS

FIG. 20

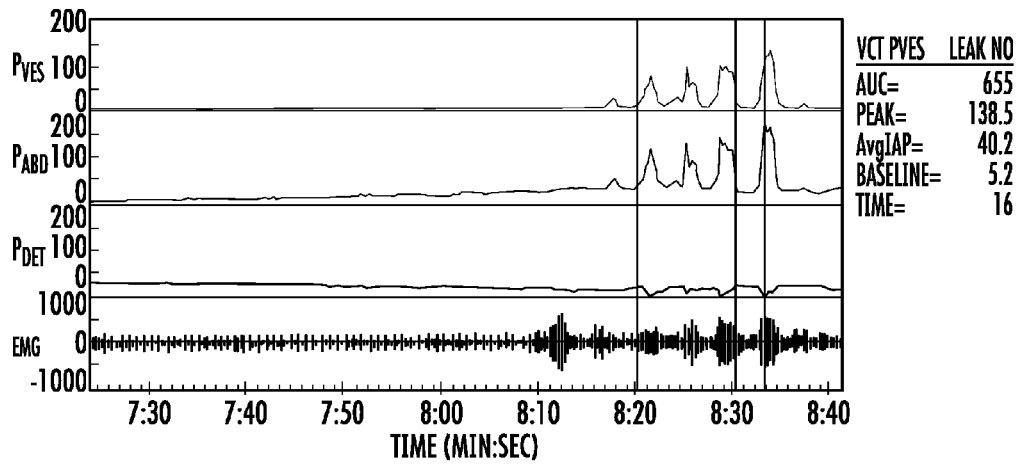
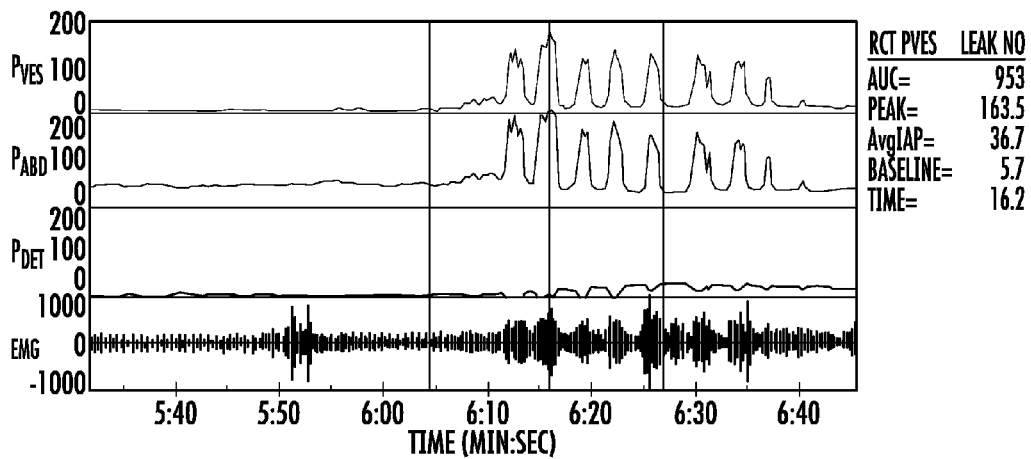
AN URODYNAMIC TRACING OF A SERIES OF FORCEFUL VC IN A FEMALE SUBJECT WHO DOES NOT HAVE A HISTORY OF SUI. THE URINARY BLADDER WAS FILLED WITH 200 ml OF SALINE AND INTRAVESICAL AND RECTAL PRESSURE CATHETERS WERE USED.
FIG. 21

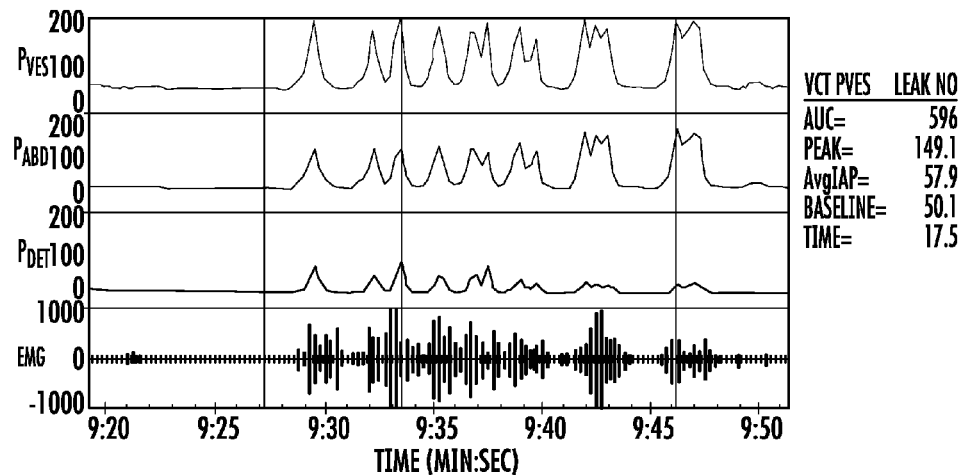
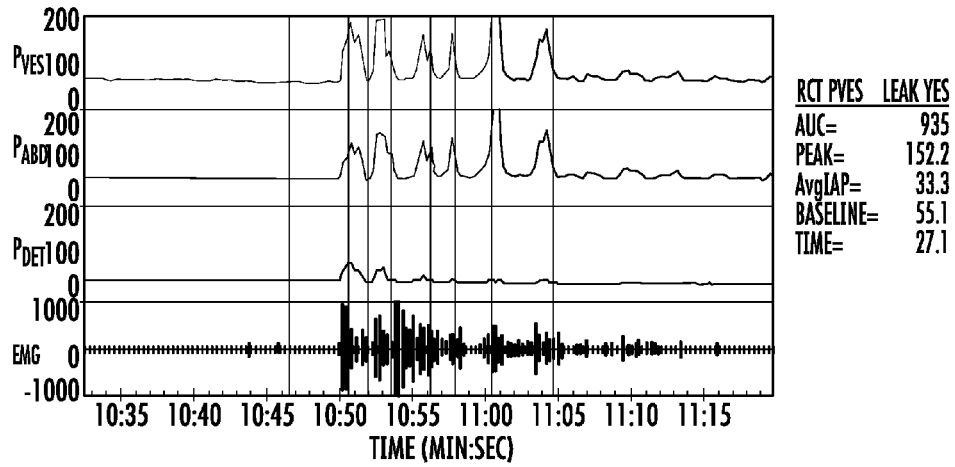
AN URODYNAMIC TRACING OF A SERIES OF FORCEFUL VC IN A FEMALE SUBJECT, WHO HAS MODERATE/SEVERE SUI. THE URINARY BLADDER WAS FILLED WITH 200 ml OF SALINE AND INTRAVESICAL AND RECTAL PRESSURE CATHETERS WERE USED. VC DID NOT ELICIT SUI DESPITE THE SERIES OF VIGOROUS INDIVIDUAL CONSECUTIVE INHALATION VC EFFORTS.
FIG. 22

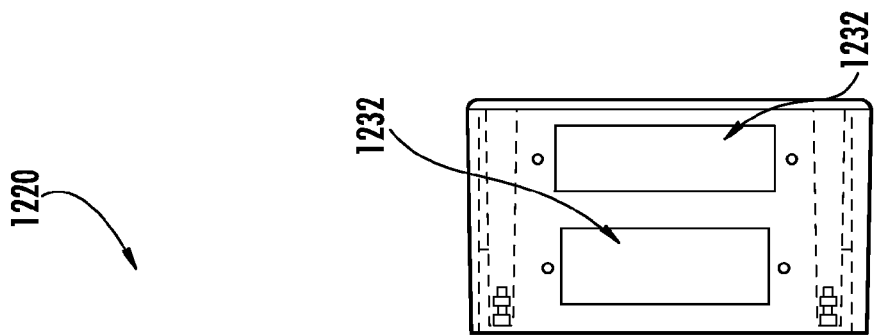
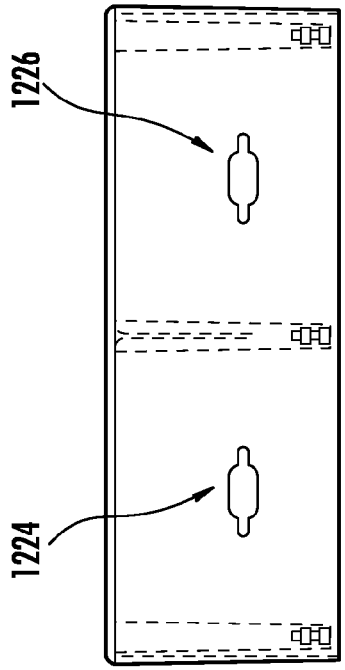
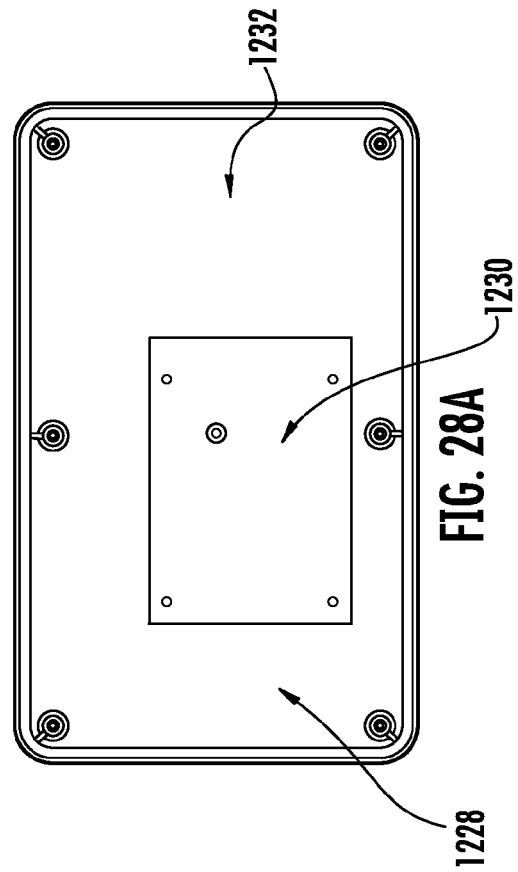
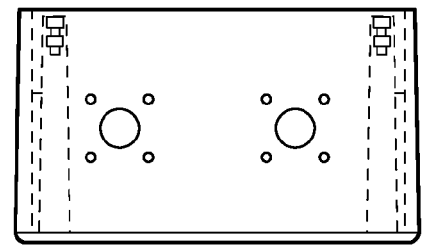
FIG. 28A
FIG. 28B
FIG. 28C
FIG. 28D

FLOW CHART OF THE COHORT SHOWING TUBE FEEDING STATUS AND SUBSEQUENT INFECTION RATES.

TIME-TO-INFECTION DATA FOR SURVIVORS (n=51) WHO WERE TUBE FED AND DEVELOPED INFECTIONS AFTER STROKE.

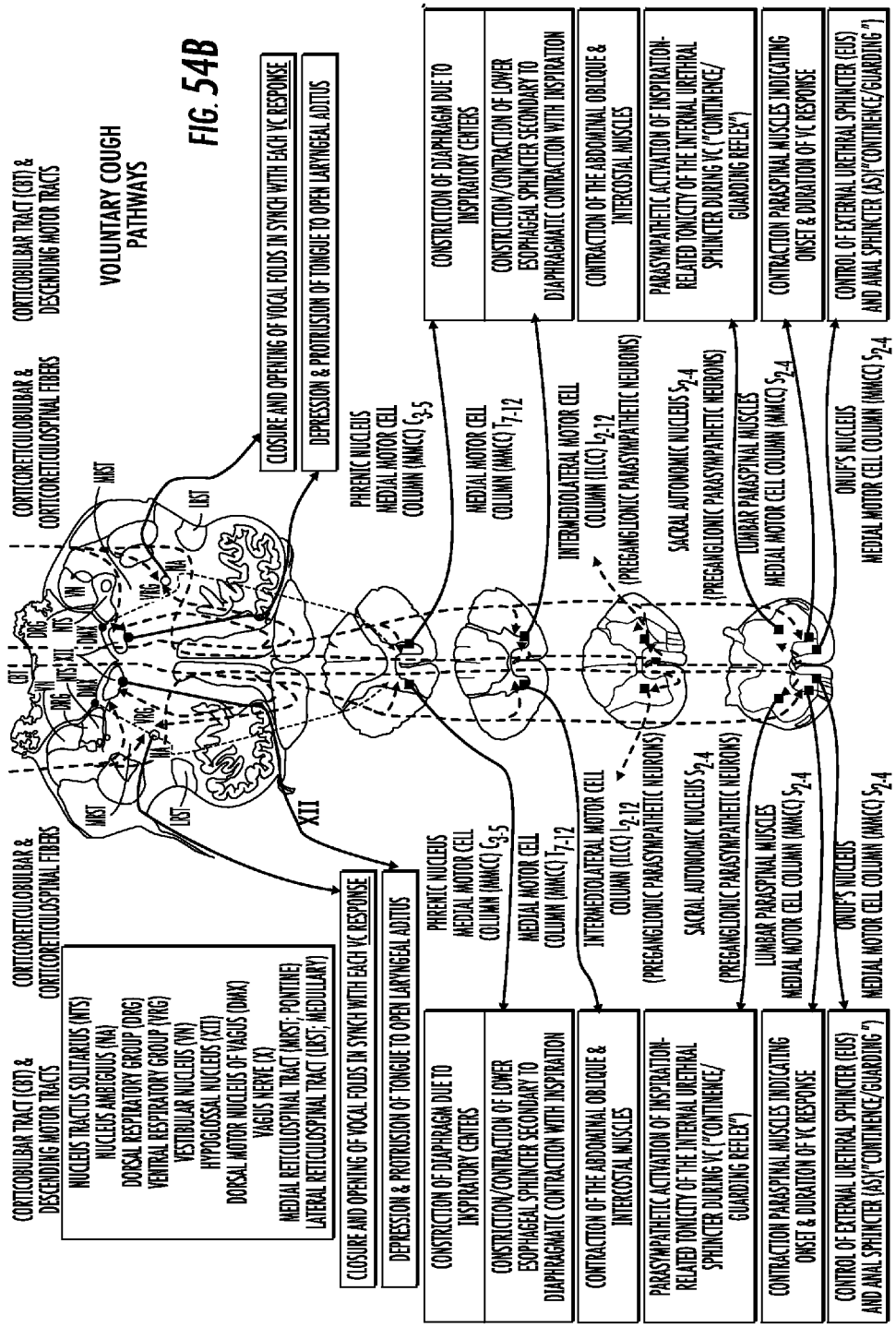

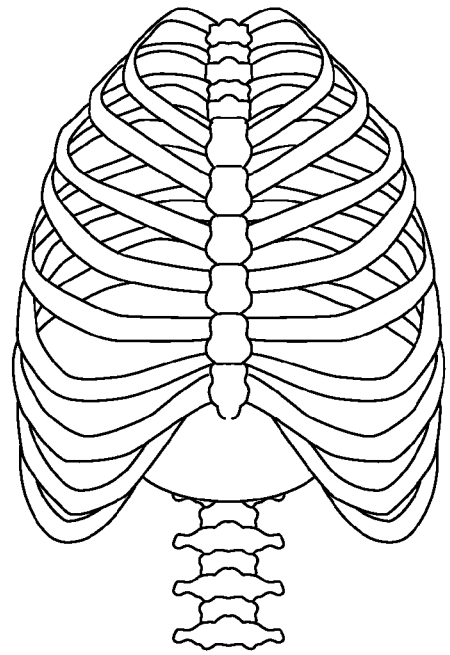
RELAXATION OF THE DIAPHRAGM DURING THE EXPIRATORY EPOCH OF LER
RELAXATION OF LOWER ESOPHAGEAL SPHINCTER (LES) DURING LER
FIG. 56

TECHNIQUES FOR EVALUATING URINARY STRESS INCONTINENCE AND USE OF INVOLUNTARY REFLEX COUGH AS A MEDICAL DIAGNOSTIC TOOL

RELATED APPLICATION(S)

This application claims priority to U.S. provisional application Ser. Nos. 61/296,304, filed Jan. 19, 2010; 61/311,882, filed Mar. 9, 2010; and 61/356,895, filed Jun. 21, 2010, and is a continuation-in-part of U.S. patent application Ser. No. 12/643,251 filed Dec. 21, 2009, which claims priority to prior filed U.S. provisional application Ser. No. 61/139,649 filed Dec. 22, 2008, and prior filed U.S. provisional application Ser. No. 61/244,167 filed Sep. 21, 2009, and which is a continuation-in-part application of prior filed U.S. application Ser. No. 11/550,125 filed Oct. 17, 2006, which claims priority to U.S. provisional application Ser. No. 60/727,740 filed Oct. 18, 2005, U.S. provisional application Ser. No. 60/752,351 filed Dec. 21, 2005, all disclosures which are hereby incorporated herein by reference in their entirety.

FIELD OF THE INVENTION

This invention is directed to the field of medical devices and testing and, more particularly, to apparatus and techniques for evaluating urinary stress incontinence.

BACKGROUND OF THE INVENTION

According to the American Academy of Family Physicians, urinary incontinence (UI) affects approximately twelve million persons in the United States alone. Although urinary incontinence can occur in both men and women, it is most common in women over the age of 50. There are many causes of UI, including age related atrophic changes in the genitourinary anatomy in women after menopause, enlargement of the prostate in men as well as generalized weakening of the pelvic floor muscles, medication side effects, immobility, infection of the urinary tract and various underlying medical co-morbidities including diabetes and hypercalcemia.

There are four basic types of urinary incontinence; functional, overflow, urge and stress. Stress incontinence occurs when there is a sudden pressure on the lower abdominal musculature, such as with a cough, sneeze, laugh or lifting. Stress incontinence is often secondary in part to weakening of the pelvic floor musculature, and is common after childbirth or abdominal surgery. It has been estimated that stress urinary incontinence occurs at least weekly in one third of adult women.

Additional reports indicate that more than 65% of female incontinence patients in the United States or 8.3 million women experience stress urinary incontinence. Of these women, approximately 85% or 7 million have incontinence primarily due to hypermobility of the bladder outlet, and approximately 15% or 1.3 million have incontinence primarily due to an intrinsic sphincter deficiency. Regardless of the etiology of UI, for the affected person it maybe a source of significant embarrassment and social isolation. As a result of this social stigma, many patients are reluctant to address this issue with their physician. Most primary care physicians "screen" for urinary incontinence by verbal or written questioning of the patient only. Additional basic evaluation may include a voluntary cough stress test, voiding diary, post void residual urinary volume, and urinalysis.

A patient experiencing urinary incontinence must be properly diagnosed to identify the specific type of incontinence from which the patient suffers. The treatments may be different, depending on the type of incontinence. Therefore, proper diagnosis becomes important at least for that reason.

Stress incontinence may result primarily in older women due to loss of extrinsic support for the pelvic organs and for the neck of the bladder. The tissues of the pelvis and of the distal urethra contain estrogen and progesterone receptors. Following menopause and decrease of the hormones, the tissues of the urethra may lose resiliency and become somewhat flaccid. Under those conditions, any increase in intra-abdominal pressure causes urine in the bladder to be pushed outwardly as resistance in the urethra is overcome, resulting in leakage of urine. This condition is known as stress incontinence and occurs in the absence of contractions by the detrusor muscle of the bladder. Stress incontinence may be responsive to treatment with exogenous estrogens, although this is not an effective treatment for all patients, particularly depending on age. Alternative treatments may include pelvic muscle exercises, α-adrenergic agents, such as phenylpropanolamine, that act on the α-adrenergic receptors along the urethra and increase urethral tone.

The most common cause of urinary incontinence, however, is detrusor hyperreflexia, or hyperactivity of the detrusor muscle. This type of incontinence is believed to result from lack of inhibition of the detrusor muscle due to a decreased detrusor reflex in the brain stem. Nevertheless, in most affected elderly there appears to be no underlying neurological defect. In this condition, treatment may include antispasmodic agents which tend to relax the wall of the bladder.

A typical test employed to distinguish these two types of urinary incontinence is one which increases intra-abdominal pressure so as to, in turn, put pressure on the bladder. The Valsalva maneuver is one such test. In this technique, the patient generates a muscular contraction of the chest, abdomen and diaphragm in a forced expiration against a closed glottis. This increases pressure within the thoracic cavity and also in the abdominal cavity. The Valsalva maneuver also refers to raising the pressure in the nasopharynx by a forced expiration with the mouth closed and the nostrils pinched, for example, to clear the patency of the Eustachian tubes. Other testing techniques involve having the patient jump up and down to jostle the bladder, or bend down so as to compress the abdomen. Yet another method involves having the patient generate one or more strong voluntary coughs.

It is known, however, that some patients are unable to perform these physical acts. For example, a patient may not be able to jump, or to bend, or to generate a strong voluntary cough. Additionally, there are some patients who will not be correctly diagnosed on the basis of the cough test, perhaps because their coughs are insufficiently strong. Accordingly, there is a need for alternative or supplementary tests that will aid in diagnosing urinary stress incontinence.

A rather complete discussion of methods of evaluating urinary incontinence is found in a February 2006 article by J L Martin et al. entitled, "Systematic Review and Evaluation of Methods of Assessing Urinary Incontinence (hereinafter referred to as Systematic review)."

One of the problems associated with the prior art techniques is that some patients are unable or are unwilling to perform the physical acts to the extent needed. For example, a patient may not be able to jump, or to bend, or to generate a strong voluntary cough. For some patients, they maybe able to perform these acts, but be unwilling to do so because an involuntary release of urine may be embarrassing or contrary to what is considered proper in society.

SUMMARY OF THE INVENTION

A system permits diagnosis of a patient for a physiological abnormality while protecting their airway. An esophageal airway protection device comprises an elongate device body having a distal end for insertion into the stomach through the esophagus and a proximal end. The device includes a main lumen extending the length of the device and an inflatable esophageal cuff carried by the device body mid-esophagus. Emesis and/or reflux is blocked from passing out of the stomach past the esophageal cuff positioned mid-esophagus when it is inflated to protect a patient's airway during an involuntary cough event. At least one electromyogram (EMG) pad is configured to obtain an EMG from an involuntary cough activated paraspinal muscles. A processing device is configured to receive the EMG and process the EMG to determine a physiological abnormality.

A nebulizer lumen in one example extends along the device body and includes a port through which medication is delivered for administrating the involuntary reflex cough test. The esophageal cuff protects the airway during the involuntary reflex cough test. A nebulizer venturi connects the nebulizer lumen and is configured to deliver nebulized medication around the device body.

In another example, at least one pressure sensor is located on the device body and configured to measure intra-abdominal pressure (IAP). The processing device receives the IAP and correlates the IAP and EMG and involuntary reflex cough epoch. In another example, the at least one pressure sensor comprises a pressure transducer and a transducer lead connecting the pressure transducer and extending into the sump lumen. At least one pH sensor is carried by the device body and the processing device receives pH measurements and processes same with EMG and IAP. A sump port is located at the distal end and the sump lumen is formed the length of the device body and configured for venting gas and preventing adherence of the device against the gastric wall.

BRIEF DESCRIPTION OF THE DRAWINGS

Other objects, features and advantages of the present invention will become apparent from the detailed description of the invention which follows, when considered in light of the accompanying drawings in which:

FIGS. 7A and 7B illustrate test results comparing a voluntary cough test and involuntary cough reflex test for assessing stress urinary incontinence.

FIGS. 11-13 are tables of results and showing statistics, correlation and samples for the average intraabdominal pressure (AIAP) (FIG. 11), the peak intraabdominal pressure (AIAP) (FIG. 12), and the Area under Curve (AUC)(FIG. 13) and comparing the involuntary reflex cough test (RCT) and the voluntary cough test (VCT).

FIGS. 17A-17C are tables showing a summary of the sensitivity, specificity, PPV and NPV in a study of urodynamic testing for SUI with comparisons for the voluntary cough test and the involuntary reflex cough test.

FIG. 20 is a table of results showing a (2×2) chi-squared statistical analysis for a series of tests and comparing the involuntary reflex cough test and voluntary cough test.

FIG. 21 are graphs showing urodynamic tracings for a voluntary cough test and the involuntary reflex cough test in a female patient who does not have a history of SUI and showing a summary of results.

FIG. 22 are graphs showing urodynamic tracings for a voluntary cough test and the involuntary reflex cough test in a female patient who has a moderate/severe history of SUI and showing a summary of results.

FIGS. 28A-28D are respective top, front elevation and side elevation views for the case or housing that can be used for the handheld device in accordance with a non-limiting example.

FIGS. 54a, 54b and 55 to 58 are figures detailing what occurs during LER and involuntary cough and showing nerve conduction pathways.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
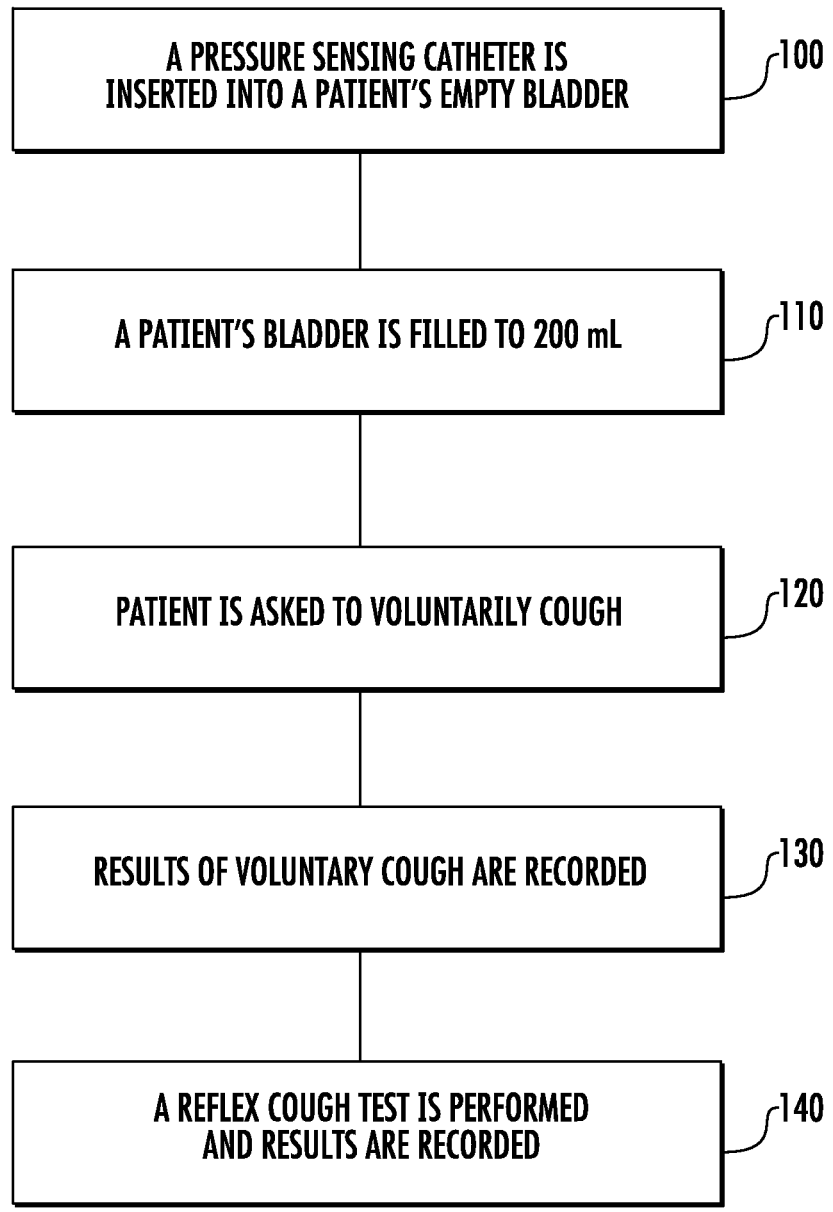
FIG. 1 shows a flowchart of a technique for evaluating a patient for urinary stress incontinence in accordance with one aspect of the invention.

FIG. 1 shows a flowchart of a technique for evaluating a patient for urinary stress incontinence in accordance with one aspect of the invention. As an initial step, pressure sensing catheter is inserted into a patient's empty bladder (100). The patient's bladder is then filled slowly with sterile water until 200 ml have been delivered (110).

The patient is then asked to voluntarily cough (120) and the results of the voluntary cough are recorded (130) by recording the variations in pressure as a function of time and by recording whether or not the cough induced involuntary expulsion of urine. See item 130.

Then, a reflex cough test is performed (140) and the results are recorded in a manner substantially similar to step 130. Details of the reflex cough tests are discussed more in conjunction with FIG. 2.

Figure 2:
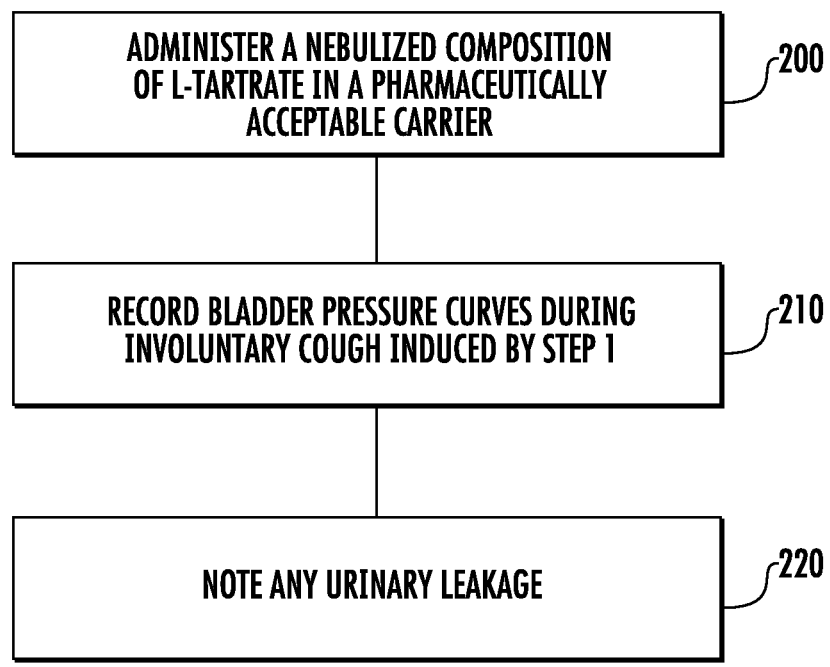
FIG. 2 shows a flowchart of a technique for conducting a reflexive cough test (RCT).

FIG. 2 shows a flowchart of a technique for conducting a reflex cough test. With the test arrangement in place as described in conjunction with items 100 and 110 of FIG. 1, instead of asking a patient to voluntarily cough, the patient is administered a nebulized composition of L-tartrate in a pharmaceutically acceptable carrier (200). The variations in bladder pressure that occur during the involuntary coughs induced by step 200 are then recorded and plotted for display (210). The patient is checked for any urinary leakage that occurs during the involuntary coughs (220).

Figure 3:
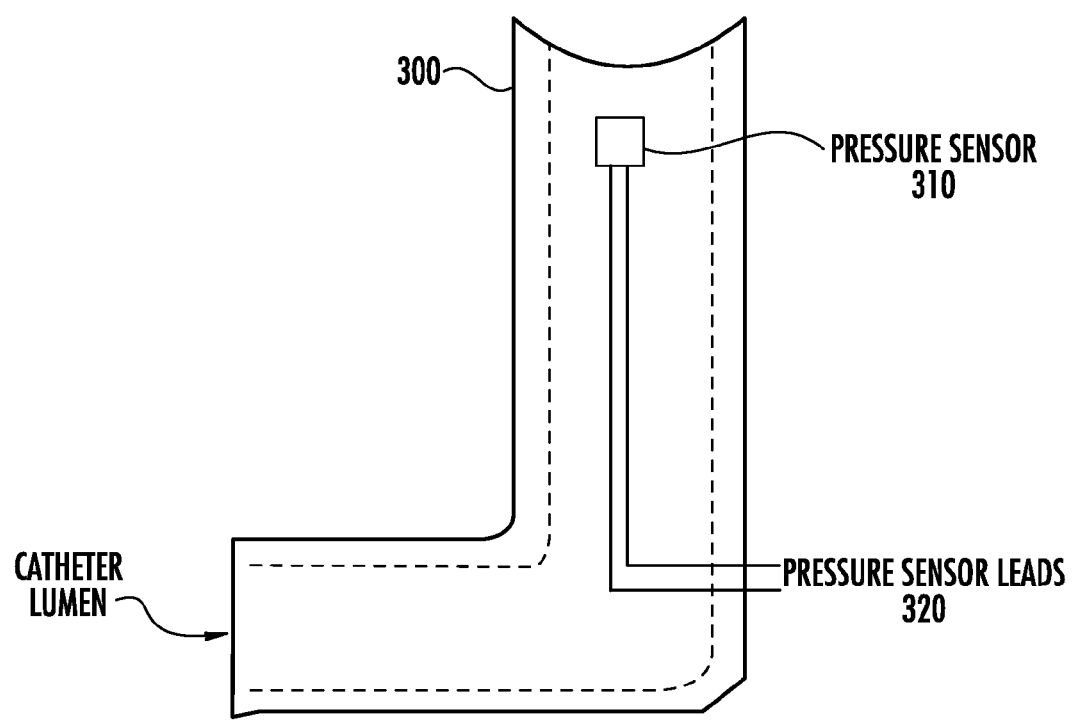
FIG. 3 shows a catheter that can be used for carrying out various aspects of the invention.

FIG. 3 shows a catheter that can be used for carrying out various aspects of the invention. A catheter, 300, includes a pressure sensor 310 and conductive wires or paths which conduct the electrical output of the pressure sensor 310 to external circuitry. The wires or paths are hereinafter called pressure sensor leads 320. The catheter lumen can be utilized to fill or drain the patient's bladder as appropriate. Examples of a catheter usable in accordance with the invention may include a Foley catheter equipped with a pressure sensor.

Figure 4:
FIG. 4 is an illustration of a handheld device that can be used to carry out the invention.

FIG. 4 is an illustration of a handheld processing device that can be used to carry out the invention. As shown on the device display screen, the variation in pressure that occurs as a function of time during a voluntary or involuntary cough is displayed.

Figure 5:
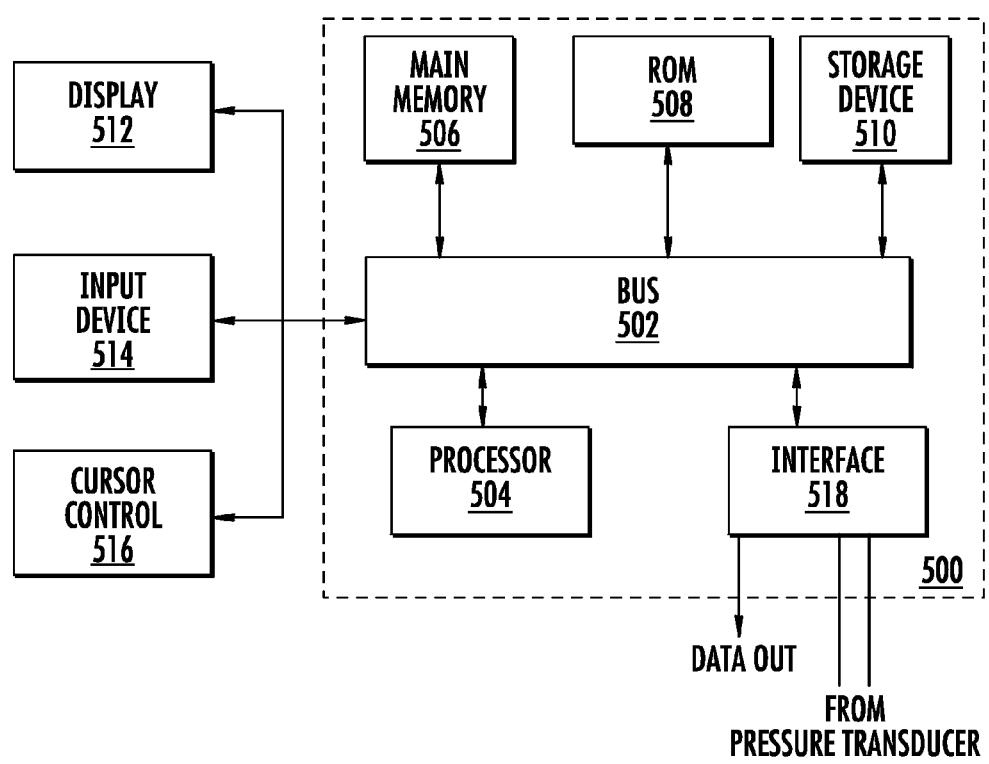
FIG. 5 is a block diagram of an exemplary processing device, such as used in the handheld device, which can be used to carry out aspects of the invention.

FIG. 5 is a block diagram of an exemplary processing device as part of the handheld device that can be utilized to carry out aspects of the invention. FIG. 5 is a block diagram that illustrates a computer system 500 upon which an embodiment of the invention may be implemented. Computer system 500 includes a bus 502 or other communication mechanism for communicating information, and a processor 504 coupled with bus 502 for processing information. Computer system 500 also includes a main memory 506, such as a random access memory (RAM) or other dynamic storage device, coupled to bus 502 for storing information and instructions to be executed by processor 504. Main memory 506 also may be used for storing temporary variables or other intermediate information during execution of instructions to be executed by processor 504. Computer system 500 further includes a read only memory (ROM) 508 or other static storage device coupled to bus 502 for storing static information and instructions for processor 504. A storage device 510, such as a magnetic disk or optical disk, is provided and coupled to bus 502 for storing information and instructions.

The interface 518 receives signals from pressure transducers connected to catheters inserted through the urethra and/or rectum and other signals, for example, EMG (electromyogram) signals such as taken from the paraspinal muscles as explained in greater detail below. EMG signals can be processed alone without catheter processor signals.

Computer system 500 may be coupled via bus 502 to a display 512, such as a cathode ray tube (CRT), for displaying information to a computer user. An input device 514, including alphanumeric and other keys, is coupled to bus 502 for communicating information and command selections to processor 504. Another type of user input device is cursor control 516, such as a mouse, a trackball, or cursor direction keys for communicating direction information and command selections to processor 104 and for controlling cursor movement on display 512. This input device typically has two degrees of freedom in two axes, a first axis (e.g., x) and a second axis (e.g., y), that allows the device to specify positions in a plane.

Computer system 500 operates in response to processor 504 executing one or more sequences of one or more instructions contained in main memory 506. Such instructions may be read into main memory 506 from another computer-readable medium, such as storage device 510. Execution of the sequences of instructions contained in main memory 506 causes processor 504 to perform the process steps described herein. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to processor 504 for execution. Such a medium may take many forms, including but not limited to, non-volatile media, volatile media, and transmission media. Non-volatile media includes, for example, optical or magnetic disks, such as storage device 510. Volatile media includes dynamic memory, such as main memory 506. Transmission media includes coaxial cables, copper wire and fiber optics, including the wires that comprise bus 502. Transmission media can also take the form of acoustic or light waves, such as those generated during radio-wave and infra-red data communications.

Common forms of computer-readable media include, for example, a floppy disk, a flexible disk, hard disk, magnetic tape, or any other magnetic medium, a CD-ROM, any other optical medium, punchcards, papertape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 504 for execution. For example, the instructions may initially be carried on a magnetic disk of a remote computer. The remote computer can load the instructions into its dynamic memory and send the instructions over a telephone line using a modem. A modem local to computer system 500 can receive the data on the telephone line and use an infra-red transmitter to convert the data to an infra-red signal. An infra-red detector can receive the data carried in the infra-red signal and appropriate circuitry can place the data on bus 502. Bus 502 carries the data to main memory 506, from which processor 504 retrieves and executes the instructions. The instructions received by main memory 506 may optionally be stored on storage device 510 either before or after execution by processor 504.

Figure 6:
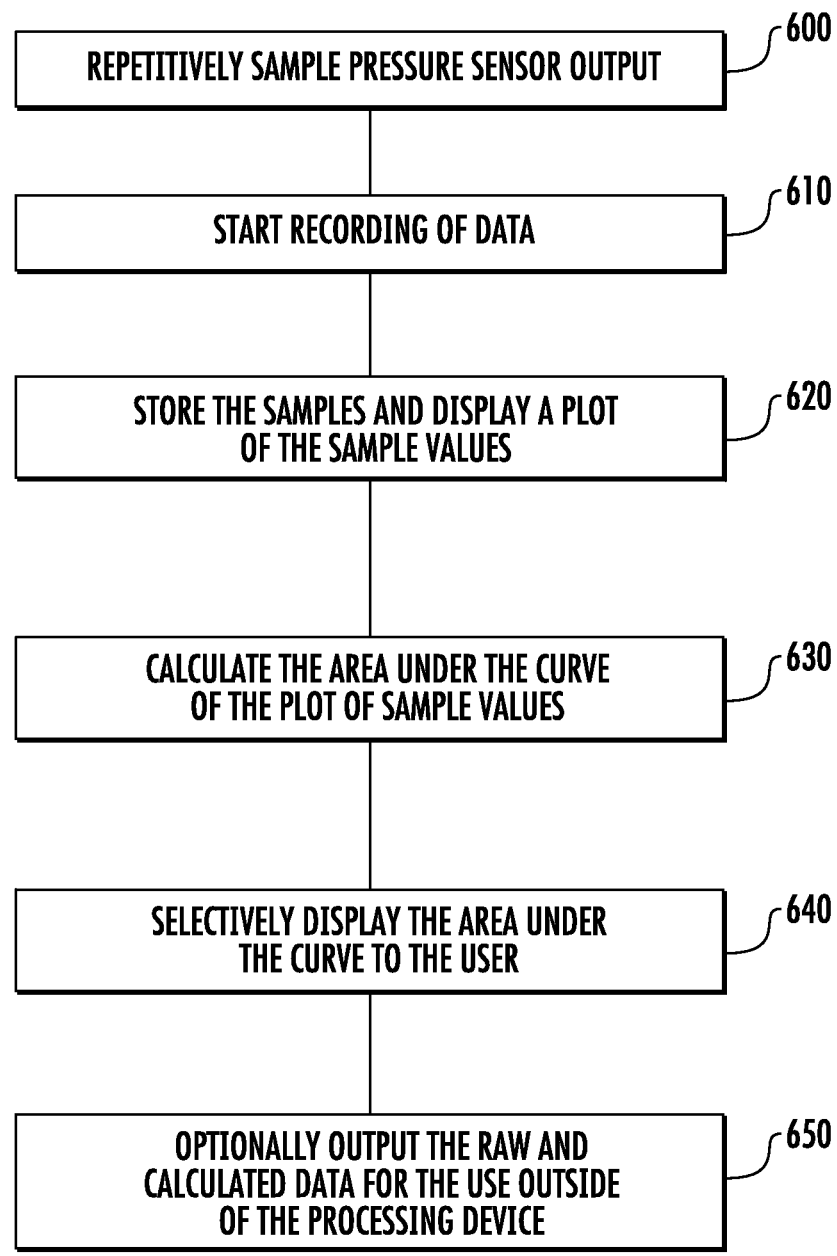
FIG. 6 is a flowchart of software used to program a processing device in accordance with one aspect of the invention.

FIG. 6 is a flowchart of software used to program a processing device in accordance with one aspect of the invention. The processing device is programmed to repetitively sample pressure output from the sensor (600). Upon receipt of an initiation or start signal, the processor can start recording data from the pressure sensor (610). The start signal can be generated by utilizing either a rapid increase in pressure, by detecting a pressure threshold being exceeded, or by receiving a trigger signal initiated by a user. Such a signal was discussed in conjunction with U.S. patent application Ser. No. 10/783,442, filed Feb. 20, 2004, entitled Apparatus For Evaluating A Patient's Laryngeal Cough Reflex And Associated Methods, by W. Robert Addington, Stuart Miller and Robert Stephens, referred to above.

After receipt of the starts signal, the processing unit stores the samples and displays the plot of the pressure sample values (620).

Upon completion of the cough sequence, software is programmed to calculate the area under the curve of a plot of the sample values (630). The areas under the curve (AUC) values are calculated by the numerical integration of intravesical pressure over time with either Simpson's ⅜-rule or Bode (or Boole's) rule. Both Simpson's ⅜-rule and Bode (or Boole's) rule are methods of numerical integration that yield more accurate results for AUC than the trapezoidal method.

Simpson's ⅜ rule:

$$\int_\alpha^\beta f(x)dx \approx \frac{3h}{8} \begin{Bmatrix} \{f_0 + f_n + 3(f_1 + f_4 + \ldots + f_{n-2}) + \\ 3(f_2 + f_5 + \ldots + f_{n-1}) + 2(f_3 + f_6 + \ldots + f_{n-3})\} \end{Bmatrix} =$$

$$\frac{3h}{8}\Biggl\{ f(\alpha) + f(\beta) + 3\sum_{i=1,4,7,\ldots}^{n-2} f(\alpha + ih) + 3\sum_{i=2,5,8,\ldots}^{n-1} f(\alpha + ih) + 2\sum_{i=3,6,9,\ldots}^{n-3} f(\alpha + ih) \Biggr\}$$

Bode's (Boole's) rule:

$$\int_{x_1}^{x_5} f(x)dx = \frac{2}{45}h(7f_1 + 32f_2 + 12f_3 + 32f_4 + 7f_5) - \frac{8}{945}h^7 f^{(6)}(\xi).$$

All AUC values were calculated using Bode's (Boole's) rule, except for that of Patient #1, which was calculated with Simpson's ⅜-rule. Bode's (Boole's) method was not very adept at handling as few data points (3).

The process may selectively display the calculated area under the curve to the user either with or separately from display of the plot of the sample values (640).

Optionally, one may output the raw and calculated data for use outside of the processing device (650). This can be done utilizing interface 518.

FIGS. 7A and 7B illustrate test results comparing voluntary cough and involuntary cough techniques for assessing stress urinary incontinence.

The testing that produced the results shown in FIGS. 7A and 7B are described as follows.

Objective: The objective of this study were to:

1) Evaluate the effectiveness of the reflex cough test (RCT) versus voluntary cough in confirming stress urinary incontinence in female subjects with a history of mild urinary incontinence as determined by the Incontinence Quality of Life Instrument (I-QOL); and 2) Correlate, if indicated, intravesicular pressure measurements with urinary leakage after RCT.

Materials and Methods: Voluntary and involuntary (RCT) cough provocation maneuvers were performed during urodynamic testing in 6 women. Four women had a history of mild stress urinary incontinence and two were normal controls. The order of the cough provocation procedures was randomized.

Prior to urodynamic assessment, subjects were instructed to empty the bladder (confirmed via ultrasound). Using sterile technique, calibrated bladder and rectal catheters were placed and continuous dual-channel pressure recording was performed and the subject's bladder was filled slowly with sterile water until 200 mL had been delivered.

Cough Leak Point Pressure (CLPP) was assessed with a bladder volume of 200 mL. Leakage was determined by visual inspection of the perineum by the Investigator during the coughs, and electronically marked on the print-out. If the subject did not leak with either cough maneuver in the semi-recumbent position, the standing position was used. Urodynamic testing was completed with filling to capacity to observe for detrusor instability.

After instruction, subjects performed a maximal forceful voluntary cough (VC) and an involuntary cough. The involuntary cough was elicited by stimulating the laryngeal cough reflex by performing the RCT with the patient's nose held closed. The RCT involves inhaling a concentration of 20% L-(+)-tartaric acid dissolved in normal, sterile saline (Nephron Pharmaceuticals, Orlando, Fla.) delivered via jet nebulizer.

An independent reviewer used the continuous pressure recording of each subject to determine peak pressures, measure duration of the cough events, count the number of pressure spikes, and derive area under the curve (AUC) numbers.

Results: Peak pressures were similar when comparing voluntary cough with the RCT (FIGS. 7A and 7B). Duration of cough events, AUC, and number of spikes were all increased with RCT relative to voluntary cough. Neither of the 2 normal subjects leaked with either cough maneuver. Of the 4 subjects with mild stress urinary incontinence (diagnosed by I-QOL), 3 leaked with RCT and 2 leaked with VC. A possible carry-over effect was identified when assessing subjects that were randomized to undergo RCT testing prior to VC. There appear to be a relative increase in AUC, peak pressure, duration, and in the number of spikes with VC testing when voluntary cough testing was performed after, rather then prior art to, the RCT (FIGS. 7A and 7B). It is notable that both subjects that leaked with voluntary cough were randomized to have the RCT performed first.

RCT provides considerable "stress" in subjects with stress urinary incontinence and appears to be a useful involuntary maneuver in eliciting leakage in subjects with this condition. No other involuntary maneuver has been studied in evaluating this condition. The data suggests that RCT may be more efficient in provoking leakage in subjects with stress urinary incontinence than voluntary cough.

Figure 8:
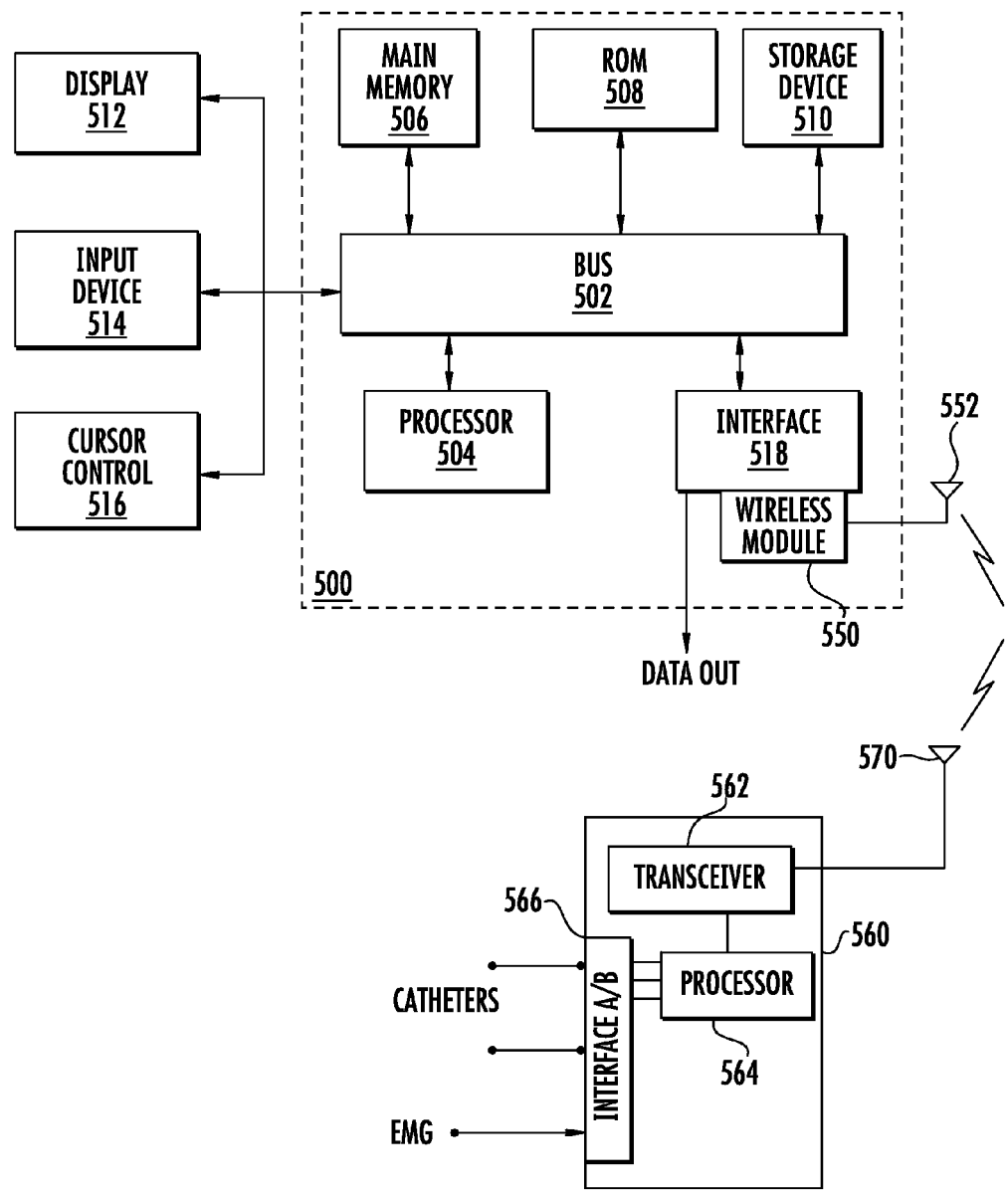
FIG. 8 is a block diagram similar to the block diagram shown in FIG. 5 and showing a wireless interface and a wireless module in the handheld device that communicates wirelessly to a wireless sensing device, which connects to catheters or other inputs, including an EMG signal input in accordance with a non-limiting example.

FIG. 8 is a block diagram of a processing device 500 as part of the handheld device similar to that shown in FIG. 4, but showing a wireless module 550 and antenna 552, which communicate wirelessly to a wireless sensing device 560. The wireless sensing device includes a wireless transceiver 562, processor 564 and interface 566 that connects to catheters or other input devices such as an EMG signal input obtained through EMG pads and associated components located at the paraspinal, for example, in a preferred embodiment. Data is transmitted using wireless communications signals via the transceiver 562 and antenna 570 to the handheld device that incorporates the processing device 500. Data processing is accomplished in the handheld device using appropriate circuitry as described before.

There now follows greater details of the involuntary reflex cough used not only for accessing stress urinary incontinence, but also for use as a medical diagnostic tool in accordance with non-limiting examples.

There now follows a general description of physiology for the involuntary reflex cough test (iRCT), which activates the Nucleus Ambiguus. The iRCT selectively activates the Medial Motor Cell Column (MMCC) of the spinal cord rather than the (Lateral) LMCC to fire muscles embryologically predetermined to be involuntary cough activated muscles in the pelvis. In the past, urologists did not selectively activate MMCC without overtly activating the LMCC. Magnetic stimulation or electrical spinal cord stimulation activate both cell columns and thus it is not possible to sort out pathology with these. Magnetic stimulation or other approaches from CNS activation set off both columns.

The pelvic muscles that typically are activated with MMCC cough activation include the lumbar-sacral L5/S1 paraspinal axial musculature, which facilitates inpatient continence screening. An example is through MMCC iRCT muscle activation, obtaining L5/S1 paraspinal firing but not L5/S1 lateral gastrocnemius activation because the gastroc muscles are limb muscles activated primarily through the LMCC.

The L-S paraspinals are easier to access with a large pad placed above the sacrum on the midline that contains active, reference and ground combined. It is not important to determine lateralization of the activity like needle EMG for radiculopathy, but only if activation occurs reflexively where the onset latency is under the pressure activation of the abdomen such as the Levator Ani. This is a poor muscle for these purposes because people train it to activate and set their pelvis if the person senses any intra-abdominal pressure elevation. Also, it is difficult to get pads to stick to that area with hair, perspiration, fungal infections or bowel/bladder incontinence present, and other factors.

Some examples have been developed and studied, including a normal CNS patient with Lumax bladder and bowel catheters and pads at L5/S1 paraspinals and a separate EMG machine and electrodes at the pelvic floor in a standard 3:00 and 9:00 o'clock set-up to demonstrate simultaneous involuntary activation with iRCT. This sets off the pelvic floor muscles. Thus, normal airway protection data is obtained and normal CNS data to L1 (where spinal cord ends). The set-up includes a complete T12 that cannot void and needs intermittent catheterization with the same set up, thus demonstrating data for normal airway but no L5/S1 EMG activation by MMCC with all the other data necessary to prove an unsafe bladder by the algorithm. A quadriplegic can demonstrate abnormal airway protection and abnormal EMG activation at both paraspinal and pelvic floor muscles with unsafe bladder measurements that follow the algorithm.

It should be understood that iRCT is an involuntary maneuver that activates embryologically predetermined muscles for airway protection and continence that travel primarily through the MMCC in the spinal cord. Different varieties of lesions are captured and determined with summated interval data approach for general screening purposes.

There now follows an initial study of the iRCT test results relative to SUI and followed by detailed examples showing support for iRCT to determine SUI and for neurophysiological analysis and showing progressive understanding of the advantageous use of the iRCT.

It is known that the laryngeal cough reflex (LCR) is a strong brainstem-mediated reflex that protects the upper airway by preventing aspiration, or the entrance of secretions, food, and/or fluid into the airway below the level of the true vocal cords (rima glottidis), through elicitation of an involuntary cough. The LCR is activated through the stimulation of cough receptors in the vestibule of the larynx. One way this is achieved is through the inhalation of chemostimulants, such as tartaric acid. Studies have shown that if the LCR is intact, the subject will involuntarily cough (normal LCR) upon inhaling a solution containing TA.

In one non-limiting example, the iRCT involves the inhalation of a nebulized 20% normal saline solution of L-TA (Tartaric Acid). Subjects are asked to perform 1 to 3 effective, full inhalations (about 15-20 second exposure by mouth for tidal breathing wearing a nose clip) from a standard jet nebulizer with at least 50 psi from an oxygen wall unit or tank that produces an average droplet diameter of 1 to 2 microns or less. The nebulizer output is 0.58 mL/min. The initiation of an involuntary cough reflex after any one of the inhalations is the end point of the procedure.

Nebulized TA is a chemical tussive that stimulates irritant receptors in the mucosa of the laryngeal aditus. Mild irritation of these receptors results in nerve impulses being conveyed by the internal branch of the superior laryngeal nerve (ibSLN) to bulbar centers of the brainstem. This nerve constitutes the afferent sensory component of the LCR arc. The efferent component of the LCR is mediated through the vagus, phrenic, intercostals and thoracoabdominal nerves.

Inhaled TA is selective in stimulating rapidly adapting ("irritant") receptors (RARs), in the supraglottic region. In humans, bilateral anesthesia of the ibSLN abolishes TA-induced cough and permits tidal breathing of the nebulized vapor without coughing, supporting the idea that the RARs are responsible for TA-induced cough.

The physiological response from inhalation of TA in a normal subject is abrupt, forceful coughing of short duration. Using a 20% solution of inhaled nebulized TA is a safe, reliable way to assess the sensation in the supraglottic laryngeal region and subsequently the neurologic circuitry of the LCR. In addition, the ability of the iRCT to predict the integrity of the protective LCR in subjects with stroke has been studied.

A 20% solution of TA as an aerosol causes cough by stimulating sensory nerves in and under the laryngeal epithelium. These nerves have been identified histologically, and the reflexes they cause have been identified. The sensory nerves can be stimulated by both non-isosmolar and acid solutions. Tartaric acid may act in both ways, but the balance between them is uncertain.

The nerves are stimulated by the opening of membrane channels in the nerve terminals. More than 20 categories of channels have now been identified, the opening of which will allow calcium flow into the nerve (and also sodium, with exit of potassium), with the result that an action potential is set up, which travels to the brainstem in the central nervous system (CNS), and reflexively induces cough.

Several different types of sensory nerve ending in the larynx have been identified that may mediate cough and other defensive reflexes. They have been extensively studied, mainly in experimental animals by recording the action potentials in their nerve fibers. The probable candidates for cough are the RARs or 'irritant' receptors. These are highly sensitive to mechanical stimuli, to hyperosmolar solutions, and to acids.

Once stimulated, the sensory nerves will induce a variety of defensive reflexes which protect the lungs from invasion of harmful material. These include cough (an inspiration, followed by a forced expiration against a closed glottis, followed by opening of the glottis with an expiratory blast); the laryngeal cough expiratory reflex (LCER, a powerful expiratory effort with the glottis open); and the glottal closure reflex. In some instances a reflex apnea can be produced. The balance of these reflexes may depend on the nature and the strength of the stimulus. In the case of TA, the LCER seems to be dominant, possibly followed by glottal closure, and the pathophysiological advantage of this response in preventing aspiration is obvious.

There is clinical experience in subjects with stress urinary incontinence. A pilot study was initially designed as a single-center, single-blind study to evaluate the effectiveness of the iRCT in inducing an involuntary cough that would confirm urinary leakage in female subjects with a history of mild SUI. Up to 3 inhalations of a 20% sterile, aqueous solution of TA delivered via an ultrasonic jet nebulizer with oxygen at 50 psi to deliver droplets of ≤1 μm were administered to yield a reflex cough. The primary endpoint was the observation of urinary incontinence in subjects with a history of mild SUI during iRCT and a lack of urinary incontinence in normal subjects. Secondary endpoints were documentation of bladder and abdominal pressures and tolerability of iRCT.

The initial enrollment was 6 women (18-75 years of age), including 4 women with a history of mild SUI as determined by the Incontinence Quality of Life Instrument (IQOL) and 2 healthy controls with no history of SUI. However, the protocol was amended to increase total enrollment from 6 to 9 subjects (7 with SUI and 2 healthy controls).

The study protocol assessed the two cough provocation maneuvers (voluntary cough test and iRCT) for each subject. The order of the cough provocation was randomized but each subject completed both tests. The protocol was subsequently amended to remove blinding and randomization from the study and all subsequently enrolled subjects underwent VCT followed by iRCT followed by a second VCT. Subjects underwent the provocation maneuvers within 30 days of screening and then had two follow-up visits: the first 1 to 5 days after treatment; the second 5 to 7 days after treatment.

Urodynamic evaluation was done during each cough maneuver. The parameters determined during this evaluation included maximal urethral pressure (MUP), maximal abdominal pressure (MAPF), maximal detrussor pressure (MDPP), maximal abdominal leak point pressure (MDLPP), maximal detrussor leak point pressure (MDLPP), and CLPP.

A total of 9 subjects were evaluated, 2 without SUI and 7 with a history of mild SUI. All subjects enrolled in this study were white and not of Hispanic or Latino background. Subject age ranged from 31 to 71 years. The mean subject age was 48.4 years: 51.0 years for healthy controls and 47.7 years for subjects with SUI. Two (22%) subjects were smokers: 1 (50%) healthy control and 1 (14%) subject with SUI. The remaining 7 (78%) subjects were non-smokers.

Individual subject responses to the cough provocation tests are summarized in Table 1. The two control subjects (#2 and #3) did not leak with either VCT or iRCT. Of the remaining 7 subjects with mild SUI, only 2 subjects (#8 and #4) did not produce leak with either VCT or iRCT. Two other subjects (#5 and #6) produced leak with both VCT and iRCT. The remaining 3 subjects (#1, #7, and #9) did not produce leakage with VCT but did with the iRCT.

TABLE 1

Individual Subject Responses to iRCT and VCT: Protocol PNEU-01-002

| | | Urine Leakage? | | |
|---|---|---|---|---|
| Subject | Status | VCT | iRCT | VCT |
| 2 | Normal | No | No | — |
| 3 | Normal | No | No | — |
| 1 | SUI | No | Yes | — |
| 4 | SUI | No | No | — |
| 5 | SUI | Yes | Yes | — |
| 6 | SUI | Yes | Yes | — |
| 7 | SUI | No | Yes | No |
| 8 | SUI | No | No | No |
| 9 | SUI | No | Yes | No |

VCT, voluntary cough test; iRCT, induced cough reflex test; SUI, stress urinary incontinence.

The performance of the cough provocation procedures is presented in Table 2. Sensitivity of the cough provocation maneuvers was 71.4% during iRCT and 28.6% during VCT. Specificity was 100% during iRCT and VCT. The positive predictive value (PPV) was 100% for iRCT and VCT; the negative predictive value (NPV) was 50% for iRCT and 28.6% for voluntary cough.

TABLE 2

Performance Statistics of the Cough Procedures: Evaluable Population

| | Voluntary Cough N = 9 | Reflex Cough N = 9 |
|---|---|---|
| Sensitivity[1], n/N (%) | 28.6 | 71.4 |
| Specificity[2], n/N (%) | 100 | 100 |
| PPV[3], n/N (%) | 100 | 100 |
| NPV[4], n/N (%) | 28.6 | 50 |

PPV, positive predictive value; NPV, negative predictive value; TP, true positive; FN, false negative; TN, true negative; FP, false positive.
[1]Sensitivity = TP/(TP + FN)
[2]Specificity = TN/(TN + FP)
[3]PPV = TP/(TP + FP)
[4]NPV = TN/(TN + FN)
The evaluable population was defined as all subjects who met study entry criteria and completed all cough maneuvers.
For subjects enrolled after Protocol Amendment 1, data from the first voluntary cough was used.

The urodynamic parameters were summarized and there was a trend for increased mean abdominal pressure (cm $H_2O$) and mean detrussor pressure when the subjects were administered the iRCT compared with the VCT. The CLPP was not consistently higher after iRCT compared with after VCT.

The trend for an increase in abdominal and intravesicular pressures after the iRCT compared with the VCT in those subjects who experienced leakage suggests that the iRCT causes significant stress on the sphincter, resulting in urinary leakage.

Analysis compared a digitized area under the pressure curve (AUC) after the iRCT, and after VCT was also conducted. Digitization of the pressure-time curve from the recordings allowed quantification of the stress generated during the cough procedures. Using the average intravesicular pressure ($P_{ves}$) values, AUC values were calculated by the numerical integration of $P_{ves}$ over time with either Simpson's ⅜-rule or Bode (or Boole's) rule. There was a trend for higher peak $P_{ves}$ and greater AUCs in subjects after iRCT compared with VCT. The results show that the iRCT provides a larger and more robust stress than VCT. The relatively increased value of AUC measurements with iRCT are a good numerical representation of the magnitude of stress placed on the urethral sphincter and offers an explanation for the increased number of subjects with mild SUI that leaked with iRCT when compared to VCT.

These results, combined with the urinary leakage observed after the iRCT, show that the iRCT has clinical utility in producing a standardized cough that allows for a definitive diagnosis of SUI as later explained in greater detail with further results.

No AE's occurred during this study and no clinically significant laboratory abnormalities were noted. No subjects discontinued from the study for any reason. The iRCT procedure was safe and tolerable to the subjects in this study.

In summary, three out of five women (60%) with SUI experienced urinary leakage only after the iRCT while two of the SUI subjects (40%) experienced urinary leakage after both the iRCT and VCT. Neither of the two healthy control subjects experienced urinary leakage after either the iRCT or VCT. Based on these initial results, the iRCT is more specific and sensitive than the VCT, indicating that iRCT is advantageous in the diagnosis of SUI.

There now follows an analysis and test results in greater detail that explain the advantageous use of the involuntary reflex cough test (iRCT) for investigating and diagnosing not only SUI but also physiological abnormalities such as neurologic deficiencies. It should be understood that there are differences between normal and neurological patients.

As noted before, there are ranges and boundaries with parameters that are now used to establish a normal neurological range. Some of the graphs representative of urodynamic testing as explained below show a delay between the EMG muscle activity and actual occurrence of a leak. In one non-limiting example, it is no more than a few milliseconds (six) in some examples between when the patient coughs and the leak occurs. The EMG corresponds to the electromyogram test and detects muscle electrical activity. It can be displayed visually on an oscilloscope and detected with signal peaks in a non-limiting example.

It is possible to conduct a Nerve Conduction Velocity (NCV) test as verification, and if there is a large delay, for example, six milliseconds, in one aspect, it could correspond to a neuropathological problem. In accordance with a non-limiting example, the involuntary reflex cough test (iRCT) is useful as a medical diagnostic tool and permits analysis of neuropathological problems. The involuntary reflex cough test also is used for analyzing stress urinary incontinence. A data processing methodology based on urodynamic testing and useful with the handheld device as described above is later set forth. A methodology for stress urinary incontinence analysis using the handheld device for example, is explained relative to the flowcharts of FIGS. 23-26. The involuntary reflex cough test as explained can be used as a standardized test in conjunction with the data processing as described. This is distinctive from an analysis using a voluntary cough in which a patient has time to set their pelvis. Processing EMG data also is accomplished in some examples in which the EMG is taken from the paraspinal instead of the perineal.

The EMG from the perineal muscles respond almost simultaneously to the onset of the voluntary cough because the patient does not want to leak. With the involuntary reflex cough test, on the other hand, the fast fibers that are set off reach the abdominal muscles quickly, such as in 17 milliseconds as an example. The patient is not able to set their pelvis. In some of the graphs reflecting urodynamic testing as will be described, it is evident that the onset of the EMG activity does not happen at the same time the pressure rises. Some people that have neuropathy, for example, spinal stenosis or nerve injury (even if it is mild), have a situation that prevents the reflexes from closing before the pressure has changed to push on the bladder. It is not possible to obtain this diagnostic tool methodology unless the involuntary cough reflex test is accomplished. When the involuntary reflex cough test is accomplished, it is possible to demonstrate a latency delay and show that the pathophysiology is a neuropathic problem rather than a structural problem. It is possible to separate the pathophysiology using the involuntary reflex cough test and methodology as described.

In one example, a female patient could have a weak spinal cord and her physiology is normal. This patient may not leak during the test, but the patient cannot protect her airway. Thus, using the methodology apparatus and system associated with the involuntary reflex cough test, in accordance with non-limiting examples, it is possible not only to diagnose an unprotected airway, but also to diagnose normal bladder physiology, including the neurophysiology to the patient's sphincter closure process. This is advantageous because it is then possible to determine when someone cannot protect their airway, even though they may have a normal bladder. Conversely, there are patients with a normal airway, but cannot control their bladder. This process and system as described is able to make that diagnosis and thus the involuntary reflex cough test is an advantageous medical diagnostic tool. For example, it is possible to have a patient with a poorly functioning bladder and normal airway and use of the test allows a doctor to find lower urinary tract symptoms and neuropathology. It becomes possible to diagnose a level of lesion in a patient with a full comprehensive neurologic examination using the involuntary reflex cough test, methodology and apparatus as described.

As will be described in detail later, the various components such as the nebulizer, one or more catheters, any pads for the paraspinal muscles when EMG is used, and drug as part of the nebulizer are inserted in a kit for use at the clinic, hospital or in-patient setting. Those components can be discarded after use. The handheld device, of course, will be used again. Use of the kit provides a clinician, doctor or other medical professional the readily available diagnostic tool to determine if a patient has a questionable airway and determine bladder physiology at the same time, all with the use of the one kit.

The EMG component of the waveform is typically important for analysis as explained. Two catheters are used in some analysis, one for the rectum or vagina and one for bladder. In another example one catheter is used. In yet another example, no catheter is used. EMG is taken from the paraspinals. In examples, the intravesicular pressure is important in combination with EMG taken at paraspinals. The EMG is correlated with pressure (e.g., intravesicular pressure) and a delay component. In the preferred method, the EMG is taken from the paraspinal muscles to obtain a clean signal where EMG sensors are placed on the back at the spine. In conjunction with the clean EMG signal obtained from the paraspinal muscles, it is possible to obtain the representation of where the involuntary cough event "take-off" starts and where it ends. The handheld device includes a processing device such as a microprocessor and appropriate software that correlates the data. It is possible to obtain a diagnosis for the level of lesion in a patient, while also obtaining a full comprehensive neurophysiological examination as noted before. Data is obtained from the involuntary reflex cough test and from the EMG. In one aspect depending on the type of desired analysis, a catheter is used in a non-limiting example to obtain the intravesicular pressure ($P_{VES}$).

Figure 9:
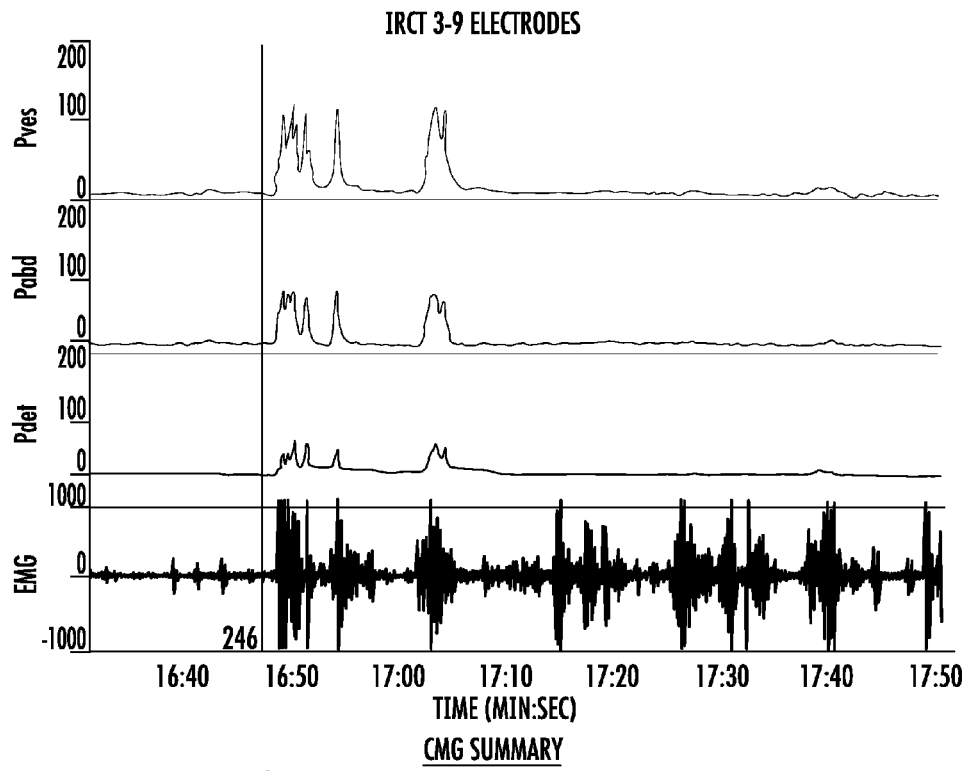
FIGS. 9 and 10 are graphs of urodynamic tracings showing results for the EMG, detrusor, abdominal and vesicular pressures for the involuntary cough reflex test (iRct) when the EMG is taken from the perineal (FIG. 9) and when the EMG is taken from the L5/S1 (FIG. 10) in accordance with a non-limiting example.
Figure 10:
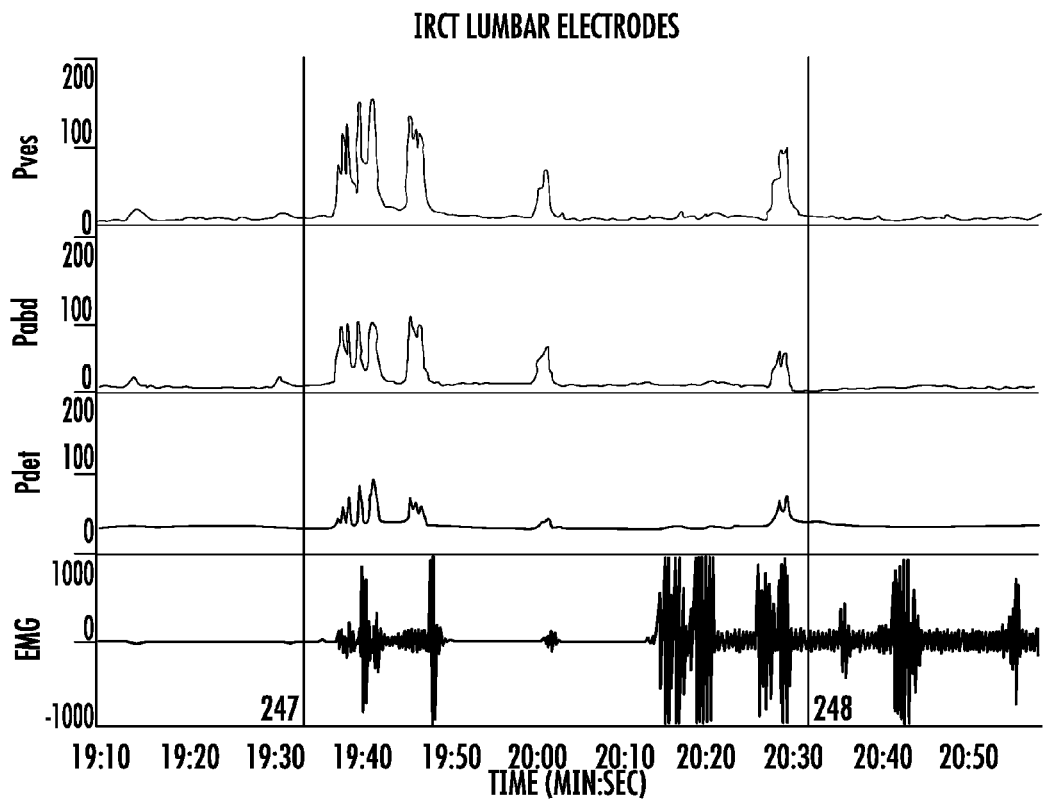

Referring now to the graphs for the urodynamic testing shown in FIGS. 9 and 10, there is illustrated time in seconds (horizontal axis) for the involuntary cough reflex test event and the various components corresponding to the vesicular pressure, abdominal pressure ($P_{VES}$), detrusor pressure, and the EMG on the vertical axis. FIG. 9 shows results for involuntary reflex cough tests when the EMG signal is taken from the perineal. Electrodes were placed at the 3:00 and 9:00 o'clock positions near the anus for the EMG taken from the perineal. FIG. 10 shows the involuntary reflex cough test using lumbar electrodes at the L5/S1 for EMG. In these examples, the EMG's were taken from a patient that cannot void following an L-S laminectomy and fusion. This patient tolerated filling the 200 millimeters and had a stress urinary incontinence history and stress urinary incontinence on the involuntary reflex cough test. The patient could not void despite the stress urinary incontinence and had low voiding pressures after filling to 350 ml, hypotonic bladder. This was a unique mix of hypotonic bladder and SUI, but otherwise no overflow incontinence. These graphs show that a better determination is made for the iRCT (involuntary reflex cough test) and EMG signal results from the L5/S1 paraspinal with a current Lumax EMG baseline. L5 corresponds to the last vertebrae in the lumbar spine and S1 corresponds to the first vertebrae in the sacral spine.

It should be understood that a Foley catheter could block the urethra. A smaller catheter is preferred to measure such as described relative to the catheter of FIGS. 31 and 32 in one non-limiting example. Some studies indicate that a poorly sized catheter could otherwise block those patients that would leak using the involuntary reflex cough test, but otherwise would not leak because of the larger catheter placement and its concomitant blocking. A smaller catheter as will be discussed later is desirable in these instances to measure pressure and serve other functions. In one example, a catheter is used for bladder screen and airway protection diagnosis, while for stress incontinence determination, a catheter may not always be necessary and a pad for determining when leakage occurs is used.

A kit that is marketed for the iRCT diagnostic tool could include the nebulizer and its drug as TA in one example and one or more pads for the electrodes at the paraspinal and use with EMG. The pad may only be necessary for stress incontinence determinations. A catheter is included in another kit example for use in measuring airway and intra-abdominal pressure. In one non-limiting example, a pad can be placed on a catheter to determine urine leakage and aid in determining stress incontinence. Pressure data is sent to the handheld device in some examples. Obtaining any EMG values from the paraspinal in conjunction with the urology analysis is advantageous. It is possible in one example to measure pressure from a bladder catheter and determine at the same time EMG signals using the EMG electrodes at the L5/S1 in conjunction with the measured involuntary reflex cough test and urology catheter sensing. This is advantageous compared to placing electrodes at the perineal muscles on each side of the anal sphincter. The graphs in FIGS. 9 and 10 show the disadvantage of the perineal EMG where interference is obtained as shown in FIG. 9 for the perineal as compared to FIG. 10 for the L5/S1 as described above.

It has been found that EMG signals obtained from the perineal muscles have EMG activity from the non-involuntary muscles, i.e., the voluntary muscles blacking out and making analysis difficult because of the signal interference. When the electrodes are placed at the back at the L5/S1 junction, on the other hand, there is nothing else but the paraspinal muscles. It is bone below on each side at the L5/S1 junction. The electrical impulses can be obtained that determine the number of cough impulses coming down through the patient. This is accomplished even if a person has much adipose. The electrode pad used at the L5/S1 junction, in one non-limiting example, typically has an active reference and ground. A pad holds this active reference and ground and the leads as the active reference and ground are plugged into the handheld device (or wireless sensing device in another example) and transmit data to the processor. At least one catheter is also plugged into the handheld device (or wireless sensing device) and measures bladder pressures. A rectal catheter can also be used in some examples. The processor receives EMG signals and determines when the cough event is over.

The involuntary coughs are not hidden by interference when measured from the lower back at the paraspinals as described. This allows a clinician to determine coughs from the bladder when the EMG is located at the L5/S1. In one aspect, the area under curve and the average pressure is determined for the cough event corresponding to the involuntary reflex cough test. When this involuntary component of the cough ends, in one example, it becomes silent EMG activity for a period of time. The pressures are at baseline for a period of time, which corresponds in one example to an inhalation. The involuntary component is over.

Sometimes with the involuntary reflex cough test, the cough occurs six times without breathing, but when the patient stops to breathe, the event is over. Using the programming applied with the processor in the handheld device, it is possible to calculate the variables inside the wave as to the involuntary cough and determine airway protection capability. Thus, it is possible to determine and measure cough by defining through appropriate data processing the involuntary cough event compared to the whole cough epoch. For example, a patient could cough ten times, but only the first four are part of the involuntary cough event. The coughs after that event are not part of the epoch.

The graphs for urologic testing in FIGS. 9 and 10 show the EMG signal component (EMG), detrusor pressure ($P_{DET}$), abdominal pressure ($P_{ABD}$) and vesicular pressure ($P_{VES}$). Obtaining the detrusor pressure is not always necessary, thus the set up may not require the rectal and urethral catheters. The analysis can be accomplished with the EMG signal component and vesicular pressure component such that apparatus used for obtaining the vesicular pressure are used. The intra-vesicular is often used to determine the intra-abdominal since both track closely. Data from the pressure measurements and EMG in conjunction with the involuntary cough reflex test are capable together with appropriate processing to assess for an unsafe bladder. There could be more continuous EMG activity in an unsafe bladder because that corresponds to an uninhibited muscle from a spinal cord injury or upper motor neuron injury.

As will be explained, the programming includes algorithm branches resulting in a conclusion of unsafe bladder based on the data analysis. It is possible to calculate from the waveforms information necessary for assessing airway protection ability. It should be understood that taking the EMG from the L5/S1 is also a better situation for the doctor or clinician, and the patient, since it is more acceptable in a hospital, outpatient or inpatient setting. The doctor or clinician does not have to bend down or stoop and look near the crotch area and place pads since the EMG can now be taken from the paraspinals. Also, the placement of pads and electrodes at the paraspinals is advantageous when patients are standing. If pads are placed at the perineal area, sweat and other problems could cause those pads to become loose and good signals may not be obtained. Also, it should be understood that the perineal muscles do not fire involuntarily. The sphincter may fire involuntarily, but that would create more noise as noted before. Electrodes are not placed at the anus, but are placed at the paraspinal area instead.

This information obtained from iRct and the EMG taken at the paraspinals allows the doctor or clinician to obtain data leading directly to a diagnosis. For example, some patients that have urinary stress incontinence may have a normal airway in this analysis. It has been found by experimentation that the normal airway is about 50 centimeters water average intra-abdominal pressure. It should be understood that the vesicular pressure (bladder pressure) can track intra-abdominal pressure and terms are often similar and used together. "Bladder" or intravesicular pressure is often used to determine and equate with intra-abdominal pressure. The two are sometimes used interchangeably. Stress urinary incontinence and/or bladder physiology can be diagnosed. The system and method as described leads directly to diagnosis. Fifty centimeters average intra-abdominal pressure over time has been found to correspond to an involuntary reflex cough test normal airway. Thus, the standard deviations or other percentages from that value are used in one non-limiting example to determine an abnormal airway. In a conducted study, the actual value is determined to be about 50.6 centimeters water as compared to voluntary cough values of about 48 centimeters of water. In an outpatient setting, it is possible to have the nebulizer (and drug) and only a pad and test SUI. In hospitalized patients or inpatient settings, this combination is used to measure airway and bladder physiology and the test combination includes a catheter.

It should be understood that the involuntary cough reflex test (iRCT) gives a higher pressure average than obtained using a voluntary cough test. The involuntary cough reflex test is thus a valuable medical diagnostic tool. In one example, four variables are significant in this analysis. These variables include: (1) duration of the event; (2) average intra-abdominal pressure of the event; (3) peak intra-abdominal pressure (max) of the event; and (4) area under the curve. Using these four variables, it is possible to process the received data and obtain a specific diagnosis that could not otherwise be obtained without the use of the involuntary reflex cough test. Individual deficits in a specific variable or combination of variables are used to characterize specific diseases and problems and useful as a medical diagnostic tool.

Some specific examples obtained through experimentation follow. For example, FIG. 11 shows paired sample statistics, paired sample correlations, and paired sample tests for a neurologically normal group of 168 patients and showing the average intra-abdominal pressure (AIAP) for the voluntary cough versus the involuntary reflex cough test. FIG. 12 shows the results for the peak intra-abdominal pressure (PIAP) and FIG. 13 shows the results for the area under the curve (AUC).

Figure 14:
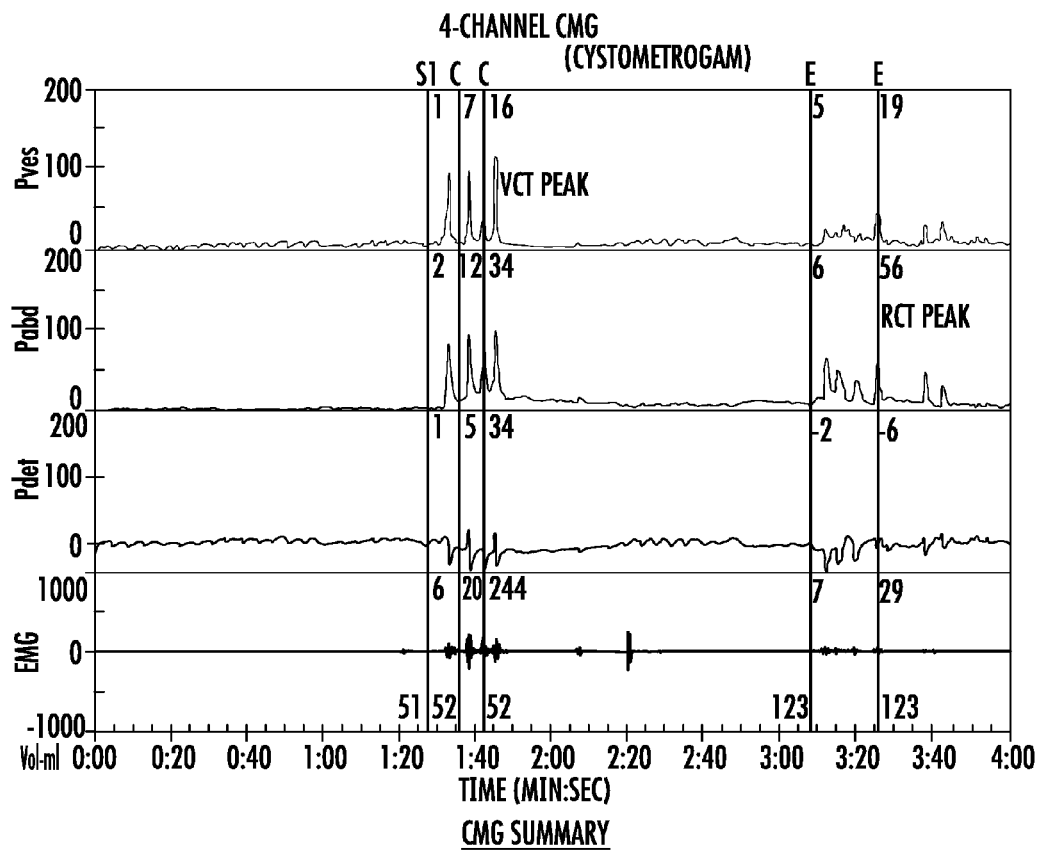
FIGS. 14-16 are graphs showing urodynamic tracings similar to those shown in FIGS. 9 and 10, for a patient with a tracheal tube removed and showing the results for the voluntary cough test (FIGS. 14 and 15) and the involuntary reflex cough test (FIG. 16).
Figure 15:
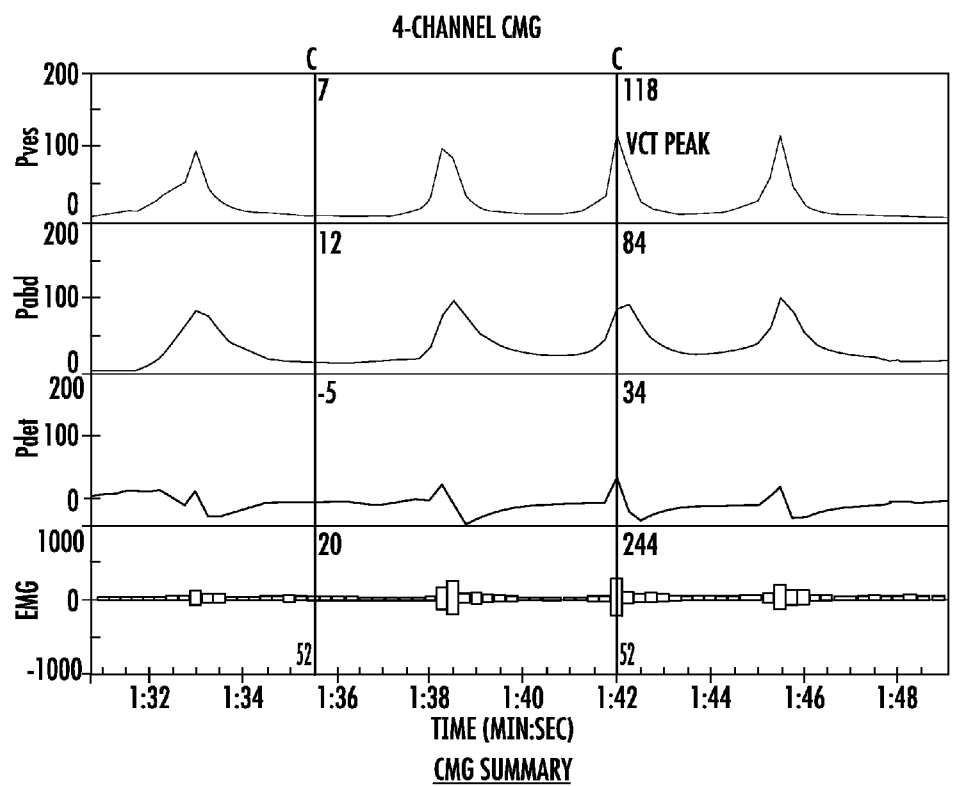
Figure 16:
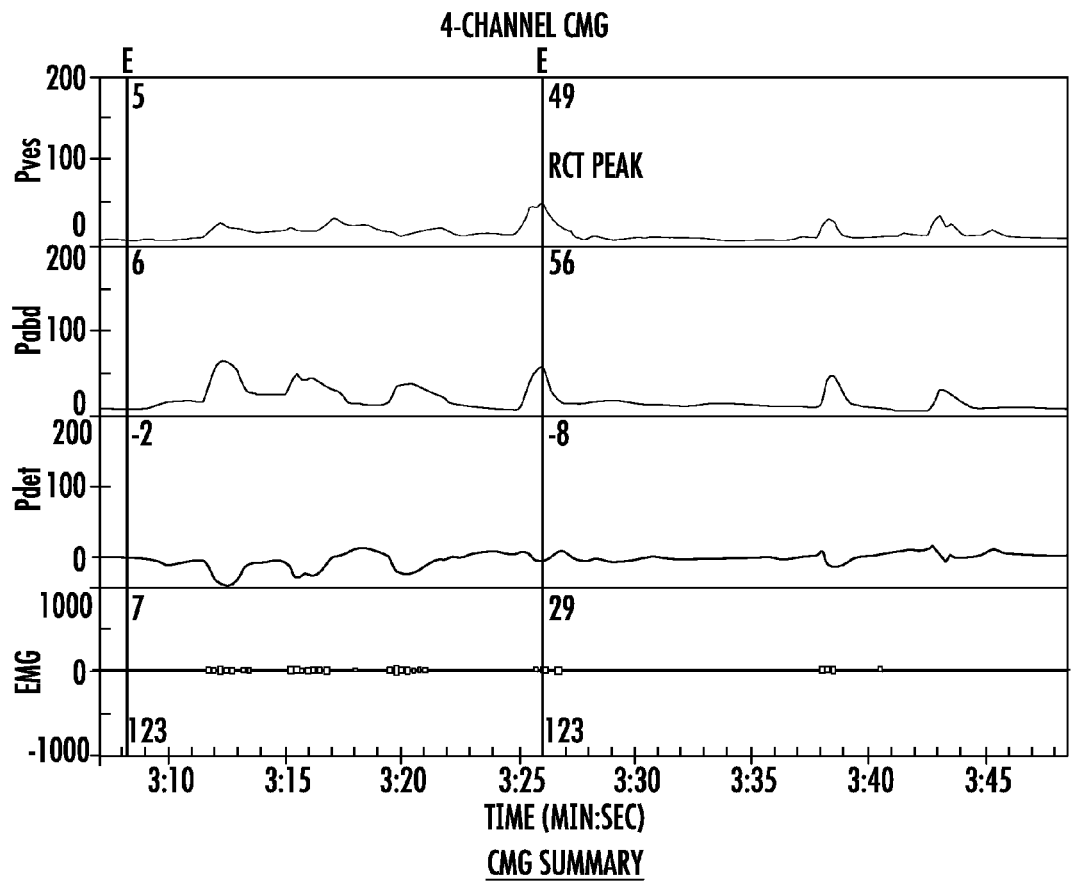

FIGS. 14-16 are graphs showing a four-channel CMG with the voluntary cough test (VCT) and the involuntary reflex cough test (iRCT) and showing the signal peaks and showing the EMG signal clarity better with the RCT than with the VCT. In the voluntary cough test, the NIF was −40, indicating the difficulty with the voluntary cough test and the advantageous use of the involuntary reflex cough test. This patient initially had a tracheal tube, which is later removed. The tracheal tube was out for the testing that was accomplished when the values shown in FIGS. 14-16 were obtained. The NIF as a negative inspiratory force of −40 (VCT) indicates a typical normal pulmonary parameter. This patient's motor reflexes, however, do not work adequately and functions shut down. During testing, this patient could be sitting for 12 seconds and have difficulty breathing and could in some cases develop acute respiratory stress syndrome or aspiration syndrome. This may require reintubation in a possible emergency situation. Otherwise, the patient could end up anoxic. It is evident that this process using the involuntary reflex cough test will help determine neurological processes (or deficits).

An analysis of the results in the tables of FIGS. 17A-17C allows a better understanding of the differences between the voluntary cough test and the involuntary reflex cough test. This provocation of cough using the involuntary reflex cough test causes urinary incontinence in subjects with SUI who do not experience urinary incontinence with voluntary cough. Alternatively, the involuntary reflex cough test does not produce urinary incontinence in healthy women without SUI. The incremental portion of subjects with a history of SUI identified in this matter are clinically useful in the diagnosis and management of SUI. This allows a determination of the Positive Predictive Value (PPV) and Negative Predictive Value (NPV) of the involuntary reflex cough test administered with urodynamic testing (some data shown in FIGS. 17A-17C). Thus, it is possible to compare urodynamic parameters obtained during a voluntary cough and during the involuntary reflex cough test.

Figure 18:
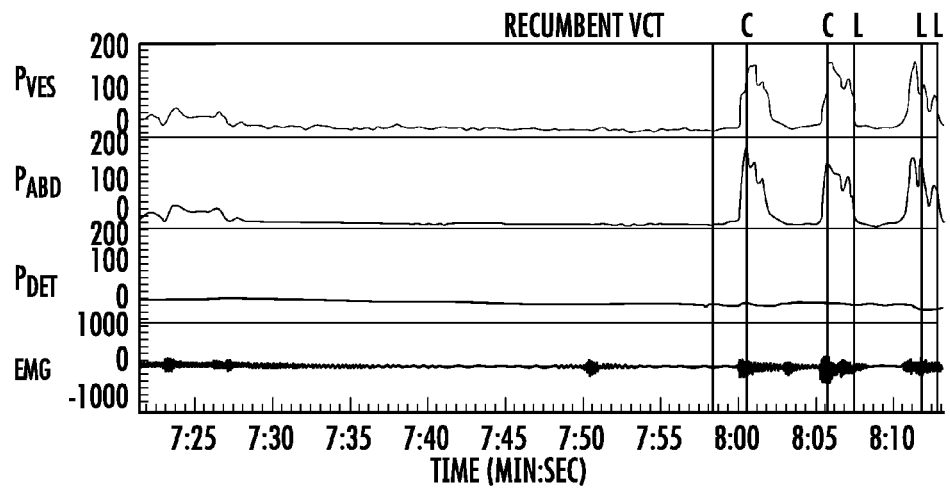
FIGS. 18 and 19 are graphs for urodynamic tests similar to those shown in FIGS. 9 and 10 and 14-16 and showing results for a recumbent patient and a voluntary cough test (FIG. 18) and an involuntary reflex cough test (FIG. 19).
Figure 19:
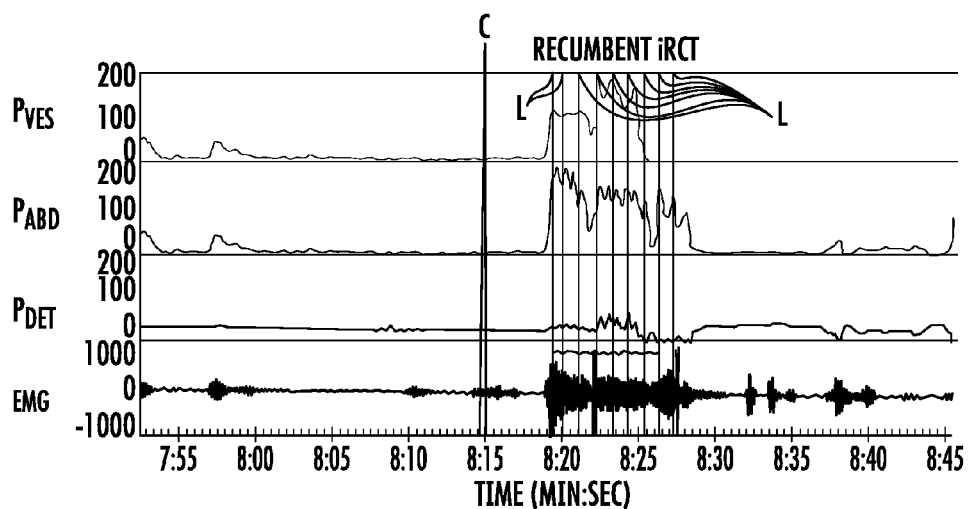

FIGS. 18 and 19 are graphs for urodynamic testing results showing data for the involuntary reflex cough as a diagnostic tool in which the involuntary reflex cough test (iRCT) visualizes or quantifies sphincter deficiencies with contrast of other quantification means. FIG. 18 shows the test results when a voluntary cough test is administered for a recumbent patient and FIG. 19 shows the test results when the involuntary reflex cough test is administered for the recumbent patient. Various lines are indicated and described below.

FIGS. 18 and 19 are graphs that show a urodynamics event in this study. The Onset to Leak (OtL) in the graph is real time (Marks under L lines below L marks). The lines with a C at the top are retrospectively placed to identify peak pressure. The subject below was classified as mild SUI (M) by the investigator after exam and entry. The OtL is recorded as seconds from pressure take-off until the observer manually pushes a button to indicate a leak is seen. The observer was blinded from the machine with a screen waist high, and the type of cough test being administered, VC vs iRCT, with noise cancelling headphones on. The observer was positioned below the waist and screen with headphones on to watch the urethral outlet and pushed the indicator line button when an observed leak was seen, which marked the timeline.

The study did not have complete uniformity among sites. One site did not mark the leaks live during the event only if there was any leak at all with one mark at the end outside the event. This site was not included in the OtL Data Tables. Another nine sites marked the events the same, during the event when leakage was seen. These are relatively accurate and come only from pushing the button and cannot be marked as a leak (L) retrospectively by the sites. The number of times the button is pushed represents the individual urine leaks seen by the observer and may vary among sites, but gives added information separating voluntary cough test and involuntary reflex cough test regarding the severity of SUI. The line and pressure take off are live and if the marks are during the event they are reasonably accurate with time lapse error from manually pushing the button. This can be repeated in a small group with automatic sensors that would mark leakage more precisely. Regardless, the evidence on the graphs shows significant differences in SUI between the voluntary cough test and involuntary reflex cough test (iRCT) for severity and mechanisms of action (MOA).

In FIG. 19, for example, iRCT, the test made the subject void, except the Detrusor Line (Pdet) is not significantly elevating during the event, which would be seen with voiding if the detrusor muscle is contracting. It appears to be stress from outside the bladder and reflects the bowel catheter symmetrically for most of the event. If the number of leaks marked and the OtL represents pathophysiology, this patient typically has at least Intrinsic Sphincter Deficiency (ISD), and thus, cannot be concluded from the leak marked on the VC event above where the OtL is 7 seconds. Inhalation probably increases resting tonic closure of the sphincters. This raises an issue whether the voluntary cough demonstrates that this inhalation activated tonic closure system works, by delaying the leak 7 seconds, while the iRCT points immediately to severe ISD (Intrinsic Sphincter Deficiency).

This is an example of why regardless if a person leaks on both voluntary cough and iRCT, it is not possible always to determine MOA or severity of SUI with voluntary cough. It is evidence of one reason overall improvement in patient outcomes and quality of life have not significantly improved despite incontinence care, especially at the general practice (GP) level. Thus, iRCT is a screening health tool useful by the GP for early identification when conservative treatment could proactively help. iRCT is also a diagnostic tool useful by the urologists to assess severity, MOA and possibly intra-operatively and assist with sling or TVT tensioning.

This same approach may work in other sphincter deficiency situations such as Lower Esophageal Sphincter (LES) and reflux. It is possible reflux laryngitis is initiated by an involuntary event, which combined with insufficiency of the closure system, leads to acid reflux which with laryngeal acid receptor activation continue the involuntary event activation and further unopposed reflux of acid. Visualization with contrast may show significant reflux differences between voluntary cough, with inhalation tonic closure reinforcement, and iRCT activated intra-abdominal pressure onset to reflux differences.

Further description concerning the involuntary reflex cough test as a diagnostic tool is now set forth. This is important not only for lower esophageal sphincter, but also for the urinary sphincter function analysis. The analysis as the chi-squared test can be accomplished by a statistician. This OtL data outcome for the voluntary cough test versus the involuntary reflex cough test is in conjunction with lunch inflation with tonic urethral and lower esophageal sphincters closure principle. This is an advantageous finding and is conclusive of why the involuntary reflex cough test is an appropriate involuntary diagnostic maneuver as a health screen tool to improve outcomes, quality of life and decrease neurological, urological and gastroenterological pathophysiology disease by improved diagnostic and measurable capabilities.

FIG. 20 shows tables for the statistical analysis (chi-squared) of the data and information. This evidence shows that leak with iRCT occurs earlier than with voluntary cough. There is some evidence that inflation of the lungs increases bladder sphincter closure and therefore might inhibit leak. Lung inflation increases abdominal pressure that tends towards leaks, which might be prevented by the additional bladder sphincter tone. Voluntary cough, unlike the iRCT, starts with an inspiration, and therefore there might be inhibition of leak in the first phase of voluntary cough. If this is so, leak should occur more frequently in the first phase (initial expiratory effort) of iRCT than in the first phase (inspiration) of voluntary cough.

Records of patients were checked in this process. Patients were located who had a leak with either voluntary cough or iRCT or both, and who had a clear indication of the timing of the leak. Each leak was labeled either as 'early' when it occurred during or immediately after the first expiratory phase of voluntary cough or iRCT, and as 'late' when it occurred during or after the second expiratory phase of voluntary cough or iRCT.

The hypothesis was that if early leak occurred more frequently with iRCT than with voluntary cough, this might be due to the leak-inhibiting mechanism in the inspiratory phase of voluntary cough, and could be a factor in explaining why time to leak (OtL) was greater with voluntary cough than with iRCT.

Records from 123 patients were analyzed. All leaked with voluntary cough or iRCT or both. Records were rejected when the leak time was not clearly identified. The distinction between early and late leak was occasionally difficult, and a 'balanced judgment' was made. Elimination of these rather uncertain timings do not change the general pattern of the analysis.

Summary analysis:
1) 8 pts leaked early with both VC and iRCT;
2) 20 pts leaked early with iRCT and late with VC;
3) 5 pts leaked early with VC and late with iRCT;
4) 14 pts leaked early with iRCT and not at all with VC.
5) 0 pts leaked early with VC and not at all with iRCT -continued 123 pts leaked. 42 pts leaked early with iRCT. 13 leaked early with VC.
Detailed analysis: Patients who leaked with both VC and iRCT and had late leak times for both:
612-2, 567-1, 605-1, 701-1, 519-1, 520-1, 522-1, 518-1, 539-1, 543-1, 551-1, 553-1, 562-1, 208-1, 303-1, 311-1, 315-1, 509-1, 511-1, 513-1, 1202-2, 1207-1, 1112-1, 823-1, 927-1, 812-1, 917-1, 1202-1, 716-1, 711-2, 1045-1, 1027-1
N = 33
Patients who leaked with both VC and iRCT and had early leak times for both:
569-1, 616-1, 1114-1, 802-1, 1035-1, 554-1, 1014-1, 1038-1
N = 8
Patients who leaked with both VC and iRCT and had late leak times for VC and early leak times for iRCT:
568-1, 516-1, 544-1, 548-1, 555-1, 556-1, 560,1, 565-1, 313-1, 1017.1, 1011-1, 1025-1, 314-1, 1204-1, 1205-1, 1117-1, 1108-1, 805-1, 809-1, 1038-1
N = 20
Patients who leaked with both VC and iRCT and had early leak times for VC and late leak times for iRCT:
1104-1, 1206-1, 934-1, 1001-2, 707-2
N = 5
Patients who did not leak with VC and had early leak times with iRCT:
540-1, 564-1, 567-1, 1203-2. 1102-1, 1106-1, 926-1, 921-1, 1021-1, 1043-1, 1029-1, 1019-1, 1012-1, 713-1
N = 14
Patients who did not leak with VC and had late leak times with iRCT:
549-1, 559-1, 517-2, 606-1, 531-1, 535-1, 536-1, 537-1, 547-1, 550-1, 552-1, 561-1, 510-1, 1208-1, 1119-1, 1120-1, 1107-1, 1111-1, 930-1, 823-1, 804-1, 702-1, 1003-1, 712-1, 717-1, 718-1, 719-1, 708-1, 701-1, 1040-1, 1041-1, 1046-1, 1036-1, 1015-1, 1008-1, 1009-1, 1006-1, 1048-2
N = 38
Patients who did not leak with iRCT but who had late leak times with VC:
611-2, 530-1, 310-1, 505-1, 820-1
N = 5
Patients who did not leak with iRCT but who had early leak times with VC:
N = 0
Summary:
    1) 123 pts were assessed. They all leaked with either VC or iRCT or both. Thus potentially there could be 246 leaks. In fact there were 189 since some pts did not leak on both tests.
    2) 118 pts leaked with iRCT (96%); 71 leaked with VC (58%); 66 (54%) leaked with both.
    3) 66 pts leaked with both VC and iRCT. 28 of them (42%) had early leak times for iRCT. 13 (20%) had early leak times for VC. (8, 12%, had both.) 33 pts (50%) had only late leak times.
    4) 52 pts leaked only with iRCT; 14 (27%) had early leak times.
    5) 5 pts leaked only with VC; none (0%) had an early leak.

FIGS. 21 and 22 are graphs showing urodynamic tracings of a test series with a forceful voluntary cough in a female subject. FIG. 21 shows the results with the female subject who does not have a history of SUI. FIG. 22 shows the results with the female subject who has moderate/severe SUI. The voluntary cough and involuntary cough reflex test are shown. The urinary bladder is filled with 200 milliliters of saline and intravesicle and rectal pressure catheters are used in this example. In FIG. 22, it shows that the voluntary cough did not elicit SUI despite a series of vigorous individual consecutive inhalation voluntary cough efforts.

As noted before, voluntary cough (VC) and the laryngeal expiratory reflex (LER) as elicited by an involuntary reflex cough test (iRCT), using a nebulized 206 tartaric acid solution, have distinctly different neurophysiological mechanisms. Voluntary cough is classically defined as an event that starts with an inspiration that leads to lung inflation. As the lungs inflate during inspiration, there is a corresponding increase in the tonicity of both the urethral sphincter (US) and lower esophageal sphincter (LES) (as shown in FIG. 21).

There is increased tonicity of the US and LES with lung inflation. Increased sphincter tonicity is a patterned motor event, which facilitates US and LES closure during increases in intra-abdominal pressure (IAA) that commonly occurs following lung inflation, i.e., the inspiratory phase of voluntary cough. The LER does not have a significant lung inflation phase prior to the series of expiratory coughs. As such, increased IAA can cause stress urinary incontinence (SUI) or gastroesophageal reflux (GER) to occur due to inadequate closure of these sphincters in subjects who have Intrinsic Sphincter Deficiency (ISD) (as shown in FIG. 22).

There now follows a description of what occurs as part of as part of normal lung inflation with inhalation as it relates to sphincter increased tonicity and closure for both urethral (US) and lower esophageal sphincter (LES) before Voluntary Cough. The Hering-Breuer inflation reflex (H-B Reflex) cannot be activated with iRCT because lung inflation does not occur. Airway protection from a perceived stimulus that could be perceived as life threatening by the body short circuits all the reflexes that are connected to the H-B Reflex system by causing vocal cord closure in 14 msecs, and in about 20 msecs IAP elevation occurs without the additional sphincter tonicity closure that would occur reflexively with inhalation lung inflation.

The involuntary reflex cough test causes significant diaphragm elevation with iRCT that does not occur with voluntary cough because the H-B Reflex, in part, holds the diaphragm down with the closed LES, despite quite highly elevated intra-abdominal pressure. The diaphragm is not held down with the iRCT, the diaphragm elevation actually pulls the LES up with it causing partial gastric content reflux. The reflux causes a vicious cough/reflux cycle to occur that leads to insidious diseases like GERD, COPD, laryngitis, Barret's Esophagitis, heartburn and similar problems. The same involuntary maneuver using the involuntary reflex cough test will diagnose SUI by blocking the inhalation tonicity that would possibly come from lung inflation via H-B Reflex.

The Hering-Breuer inflation reflex is a reflex triggered to prevent overinflation of the lungs. Pulmonary stretch receptors present in the smooth muscle of the airways respond to excessive stretching of the lung during large inspirations. Once activated, they send action potentials through large myelinated fibers of the paired vagus nerves to the inspiratory area in the medulla and apneustic area of the pans. In response, the inspiratory area is inhibited directly and the apneustic area is inhibited from activating the inspiratory area. This inhibits inspiration, allowing expiration to occur.

Josef Breuer and Ewald Hering reported in 1868 that a maintained distention of the lungs of anesthetized animals decreased the frequency of the inspiratory effort or caused a transient apnea. The stimulus was therefore pulmonary inflation.

The neural circuit that controls the Hering-Breuer inflation reflex involves several regions of the central nervous system, and both sensory and motor components of the vagus nerve. Increased sensory activity of the pulmonary-stretch lung afferents (via the vagus nerve) results in inhibition of the central inspiratory drive and thus inhibition of inspiration and initiation of expiration. The lung afferents also send inhibitory projections to the cardiac vagal motor neurones (CVM) in the nucleus ambiguus (NA) and dorsal motor vagal nucleus (DMVN). The CVMs, which send motor fibers to the heart via the vagus nerve, are responsible for tonic inhibitory control of heart rate. Thus, an increase in pulmonary stretch receptor activity leads to inhibition of the CVMs and an elevation of heart rate (tachycardia). This is a normal occurrence in healthy individuals and is known as sinus arrhythmia.

Early physiologists believed the reflex played a major role in establishing the rate and depth of breathing in humans. While this may be true for most animals, it is not the case for most adult humans at rest. However, the reflex may determine breathing rate and depth in newborns and in adult humans when tidal volume is more than 1 L, as when exercising.

The Hering-Breuer deflation reflex serves to shorten exhalation when the lung is deflated. It is initiated either by stimulation of stretch receptors or stimulation of propriocetors activated by lung deflation. Like the inflation reflex, impulses from these receptors travel afferently via the vagus. Unlike the inflation reflex, the afferents terminate on inspiratory centers rather than the pontine apneustic center. These reflexes appear to play a more minor role in humans than in non-human mammals.

FIG. 21 shows a graph for an urodynamic tracing of a series of tests and a forceful voluntary cough in a normal female subject with a urinary bladder filled with 200 ml of saline. There is no evidence of SUI, i.e., urine leakage, during the series of voluntary cough or the five-cough (C5) iRCT stimulus. With the iRCT the episode can have an average duration of 14.8 seconds and consists of an average of 5 expiratory coughs, during which there is no significant inhalation or lung inflation to activate US and LES tonicity. This subject is continent without the facilitatory effect of increased tonicity associated with lung inflation.

FIG. 22 is a graph for an urodynamic tracing of a series of tests and a forceful voluntary cough in a female subject, who has moderate/severe SUI. Voluntary cough did not elicit urinary incontinence despite the series of vigorous individual consecutive inhalation voluntary cough efforts. The iRCT caused immediate SUI with multiple leakages (lines indicated at 22*a*) during the 26-second involuntary event.

The discrepancy between the voluntary cough and iRCT in demonstrating SUI is due to the facilitatory effect of increased tonicity associated with lung inflation in voluntary cough. The voluntary cough in FIG. 22 had a similar robust peak IAP and much greater average IAP than the iRCT in this subject. The SUI was not a result from any differences in IAP or cough duration, but was secondary to the absence of the facilitatory effect of increased tonicity associated with lung inflation.

The laryngeal expiratory reflex (LER) is normally triggered when food, fluid or secretions enter the larynx during swallowing or inspiration. Reflex cough can be triggered by aspiration of food or fluid during inspiration acid reflux stimulation of laryngeal receptors or post-nasal drip into the larynx, laryngeal inflammation or infection. Although the studies on gastroesophageal reflux (GER) claim that cough is a result of gastric acid reflux, it is believed that involuntary cough is the direct cause of GER and this may lead to a previously unrecognized cycle where cough causes reflux that produces the cough associated with GER. This infers that instead of treating the cough, steps should be clinically taken to reduce the reflux. SUI is primarily caused by cough. The type of cough that causes SUI is an involuntary cough and not voluntary cough, thus, by decreasing stimuli exposure, i.e., reflux that can trigger involuntary cough, SUI could be reduced. The more comprehensive clinical approach using the involuntary maneuver, i.e., iRCT, will improve the identification of both SUI and GER when they can still be effectively and conservatively treated before the development of significant comorbidities.

Intrinsic sphincter deficiency (ISD) may be clinically present as SUI and GER. The iRCT is clinically useful in improved evaluation of LES function and a more realistic assessment of SUI.

There now follows a description of a method that can be used for processing urodynamic data obtained during the iRCT and processed in the handheld device in accordance with non-limiting examples. FIGS. 23-26 are more detailed flowcharts showing this example of various steps that can be used for obtaining and processing data received from the involuntary reflex cough text (iRTC) for stress urinary incontinence.

Figure 23:
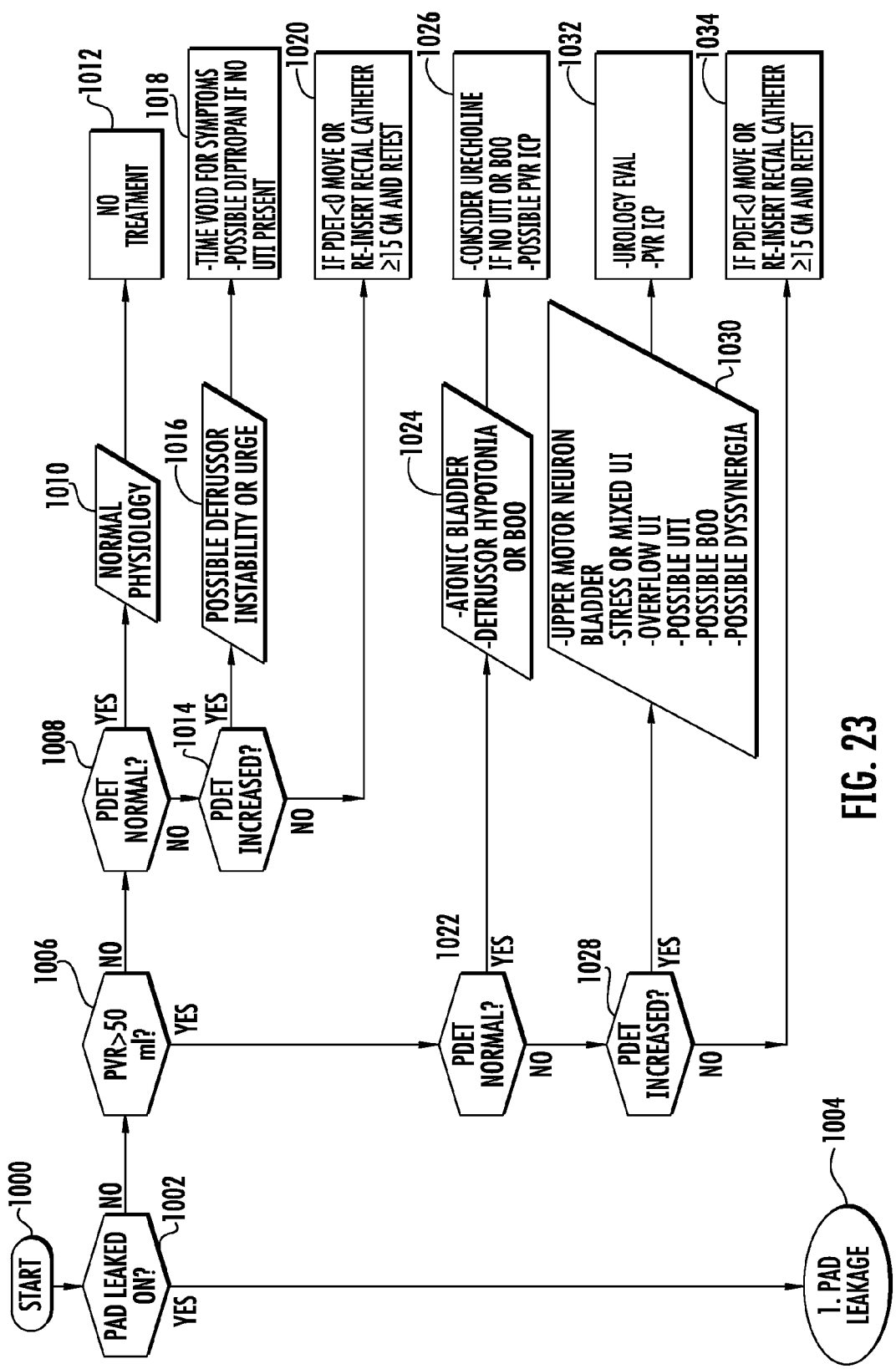
FIGS. 23 and 24 are flowcharts showing an example of a method for processing data obtained during the involuntary reflex cough test for a patient in an outpatient setting.
Figure 24:
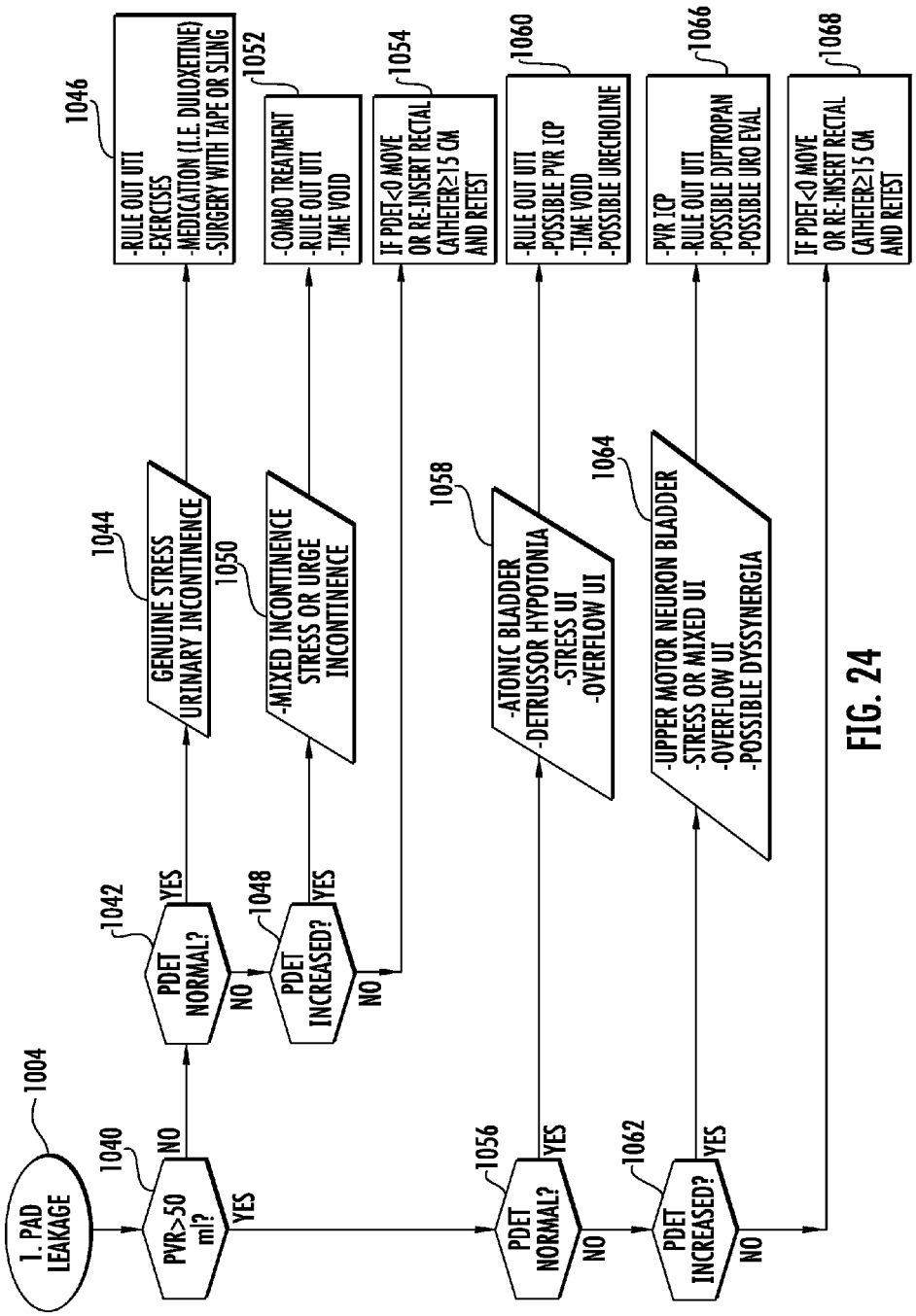

The process starts (1000) with the involuntary reflex cough test and proceeds from this test. One activity that may be pre-involuntary reflex cough test is an ultrasound to determine the starting bladder volume. It should be understood that FIGS. 23 and 24 are representative for an outpatient setting. In this outpatient example shown in FIGS. 23 and 24, it typically is about at least 200 ml starting. With the inpatient example shown in FIGS. 25 and 26, the doctor or technician waits until the patient feels the urge to void and then performs the ultrasound to measure the starting volume. There are some reasons for the differences, but neither requires bladder filling initially.

As shown in FIGS. 23 and 24 for the outpatient example, the process starts (1000) with the involuntary reflex cough test, also termed the induced reflex cough test. A determination is made if the pad is leaked on (1002) and if yes, then the sequence shown in FIG. 24 for pad leakage is followed (1004). If not, a determination is made if the post-void residual is greater than 50 ml (1006). If not, a determination is made if the detrusor pressure is normal (or elevated) (1008). Detrusor pressure is a difference between bladder and abdominal pressure and also uses a catheter in the rectum. If yes, then there is normal physiology (1010) and no treatment (1012). If not, then a determination is made whether the detrusor pressure is increased (1014) and if yes, then there is possible detrusor instability or urge (1016). This could be contractions. A course of action is a time void for symptoms and possible Diptropan if no urinary tract infection (UTI) is present (1018). If the detrusor pressure was not increased, and the detrusor pressure is less than zero, then any rectal catheter as used can be moved or reinserted an amount greater than or equal to 15 centimeters and then retest (1020). For example, the abdominal pressure is reading higher than the bladder pressure, obtaining a negative detrusor value. This could indicate that something is wrong and the catheter is not placed correctly.

If the post-void residual is greater than 50 ml, then a determination is made if the detrusor pressure is normal (1022). If yes, this could signify atonic bladder, detrusor hypotonia, or bladder outlet obstruction (BOO) (1024). Urecholine can be considered and possible post-void residual (PVR) intermittent catheterization procedure (ICP) in which the catheter is placed in the patient to drain the bladder (1026).

If the detrusor pressure was not normal, then a determination is made whether the detrusor pressure was increased (1028). If yes, this could signify an upper motor neuron bladder, stress or mixed urinary incontinence, overflow urinary incontinence, possible urinary tract infection, possible bladder outlet obstruction, and possible dyssynergia (1030). This can be followed by a urology evaluation and PVR/ICP corresponding to a post-void residual and intermittent catheterization procedure (1032). The possible dyssynergia (1030) corresponds to bladder sphincter dyssynergia also termed detrusor sphincter dyssynergia (DSD) in some non-limiting examples as a neurological condition with a contraction of the bladder musculature as not coordinated with the relaxation of the sphincter. In some of these instances, instead of the urethra completely relaxing during voiding, it may dyssynergically contract causing the flow to be interrupted and the detrusor pressure to rise. On systography, there is typically an irregular appearance of a bladder outline because of musculature contraction against the unrelaxed bladder sphincter. Usually individuals with this type of condition may have daytime and night-time wetting and a history of urinary tract infections (UTI).

If the detrusor pressure is not increased, then recatheterization can occur if the detrusor pressure is less than zero and a rectal catheter can be moved or reinserted greater or equal to about 15 centimeters and retested in this non-limiting example (1034).

In one of these outcomes, the atonic bladder typically corresponds to a large dilated urinary bladder that does not empty, usually because of the disturbance of innervation or chronic obstruction. This could require a primary caregiver or other medical professional to consider urecholine if there is no urinary tract infection (UTI) or BOO (such as in 1026). A possible PVR ICP could be considered. Urecholine, of course, is also termed bethanechol as a parasympathetomimetic choline ester that stimulates the muscarinic receptors with further selectivity for M3 receptors without any effect on nicotinic receptors.

Diptropan as a generic oxybutynin is typically used to reduce muscle spasms of the bladder and urinary tract and treat symptoms of the overactive bladder causing frequent or urgent urination, incontinence as urine leakage and increased night-time urination.

FIG. 24 shows the pad leakage (1004) sequence. A determination is made if the post-void residual is greater than 50 ml if there was pad leakage (1004). If not, a determination is made if the detrusor pressure was normal (1042) and if yes, this indicates genuine stress urinary incontinence (1044). As an outcome, urinary tract infection is ruled out and exercises can be described and medication such as Duloxetine and possible surgery with tape or sling (1046). If the detrusor pressure is not normal, a determination is made if the detrusor pressure was increased (1048) and if yes, this could indicate mixed incontinence and stress or urge incontinence (1050). As an outcome, there could be a combination treatment. Urinary tract infection is ruled-out and possible time void (1052). If the detrusor pressure is not increased and the outcome of testing is such that the detrusor pressure is less than zero, the rectal catheter can be reinserted greater than or equal to about 15 centimeters and retesting occurs (1054).

If in these steps the post-void residual is greater than 50 ml, a determination is made if the detrusor pressure is normal (1056). If yes, this could be a sign of atonic bladder, detrusor hypotonia, stress urinary incontinence or overflow urinary incontinence (1058). Again, urinary tract infection is ruled out and a possible PVR/ICP with a time void and possible urecholine (1060).

If the detrusor pressure was not normal, a determination is made if the detrusor pressure was increased (1062), and if yes, this could signify upper motor neuron bladder, stress or mixed urinary incontinence, overflow urinary incontinence, or possible dyssynergia (1064). The outcome is a PVR/ICP, the rule-out of UTI, possible diptropan, and possible urological evaluation (1066). If the detrusor pressure was not increased and is less than zero, an outcome is to move or reinsert the rectal catheter, greater than or equal to about 15 centimeters and retest in a non-limiting example (1068).

Figure 25:
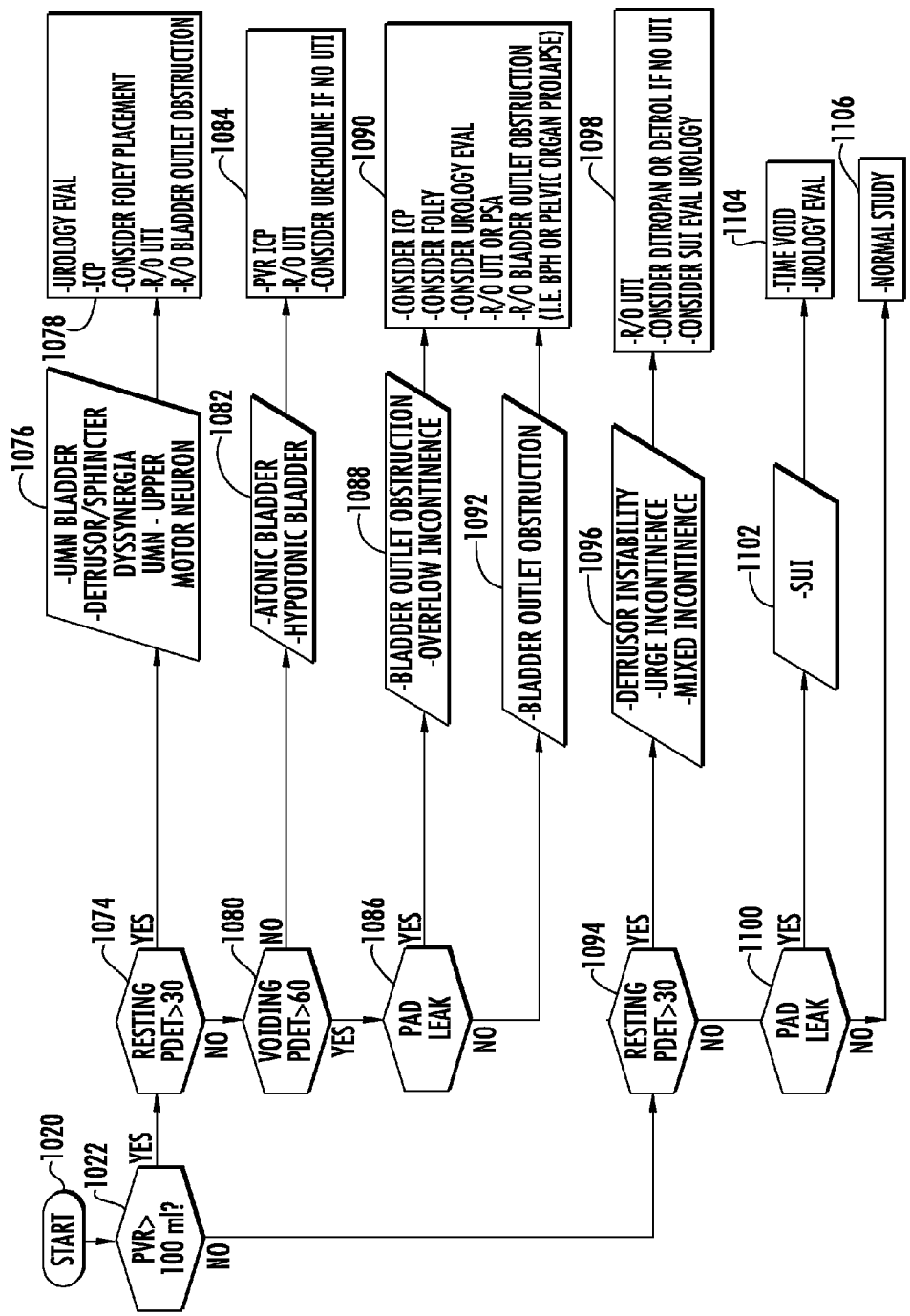
FIGS. 25 and 26 are flowcharts showing examples of a method for processing data obtained during the involuntary reflex cough test for a patient in an inpatient setting.
Figure 26:
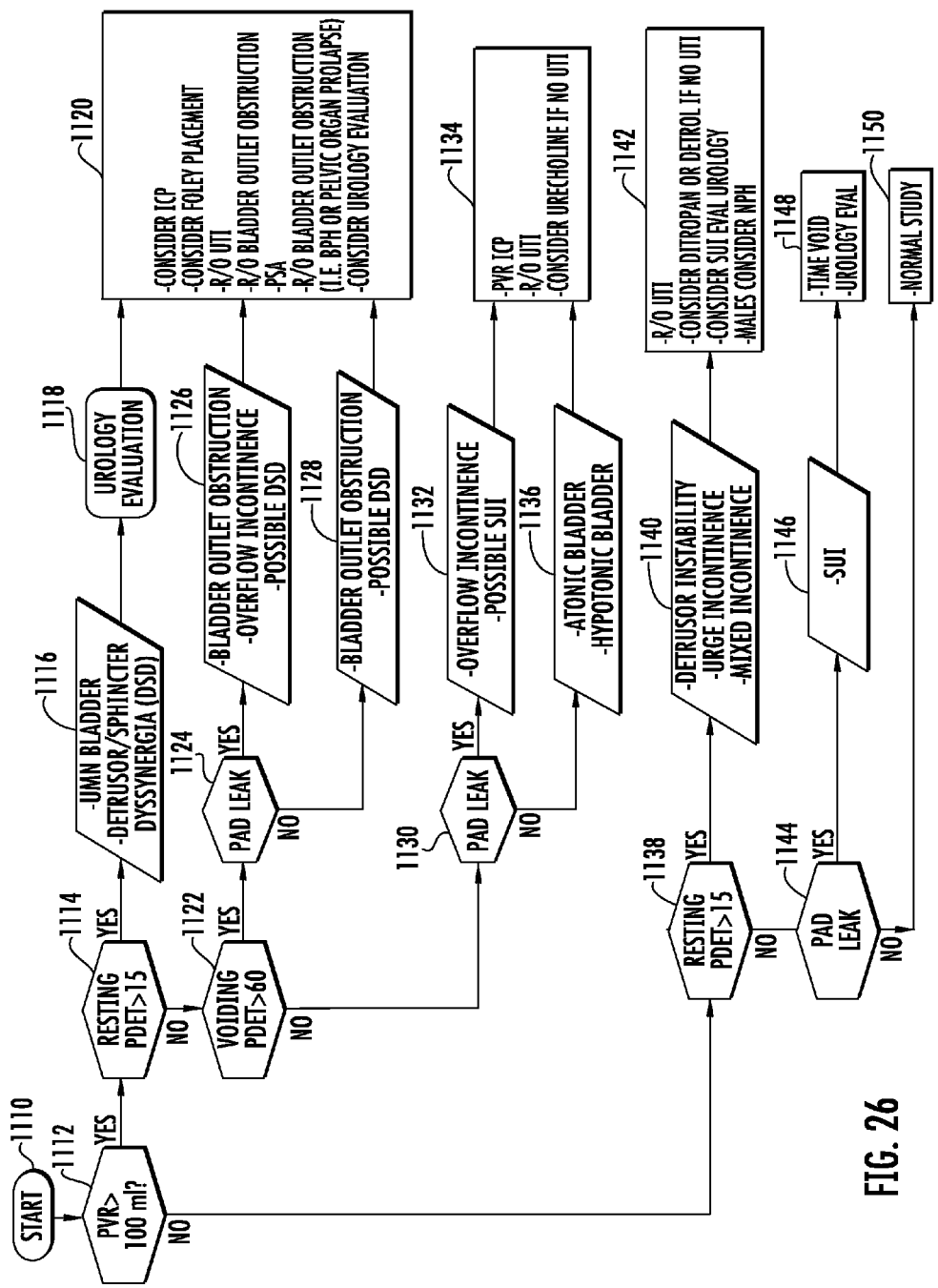

FIGS. 25 and 26 show a flow sequence similar to that shown in FIGS. 24 and 25, but in this example, the sequence is for inpatient testing. The process starts (1070) and a determination is made whether the post-void residual is greater than 100 ml (1072). If yes, then a determination is made whether the resting destrusor pressure is greater than 30 centimeters of water (1074). If yes, this could correspond to the upper motor neuron (UMN) bladder and detrusor/sphincter dyssynergia (1076). At this time, a urology evaluation can occur and ICP (intermittent catheterization procedure). The clinician can consider a Foley catheter placement. Urinary tract infection is ruled out and bladder outlet obstruction (BOO) is ruled out (1078). If the detrusor pressure was not greater than 30 centimeters of water at resting, then a determination is made whether voiding and detrusor pressure was greater than 60 (1080. If not, this can signify the atonic bladder or hypotonic bladder (1082) and the outcome can be PVR/ICP and the UTI ruled out. If there is no UTI, then urecholine is considered (1084).

If the voiding and detrusor pressure is greater than 60, then a determination is made whether the pad leaked (1086). If yes, this can correspond to bladder outlet obstruction and overflow incontinence (1088). Possible considerations can be the ICP, a Foley catheter, a urology evaluation. UTI is ruled out or prostate (PSA). The clinician also rules out bladder outlet obstruction, i.e., BPH or pelvic organ prolapse (10%). If there is no pad leak, this could possibly correspond to bladder outlet obstruction (1092) and the same outcome processing occurs (1090).

If the initial PVR was not greater than 100 ml, a determination is made if the detrusor pressure was greater than 30 centimeters of water at rest (1094). If yes, this can correspond to detrusor instability, urge incontinence and mixed incontinence (1096). UTI is ruled out and possible Ditropan or Detrol is considered if there is no UTI. A stress urinary incontinence evaluation in urology is considered at this time (1098). If the detrusor pressure was not greater than 30 centimeters of water, then a determination is made whether the pad leaked (1100), and if yes, this step corresponds to stress urinary incontinence (1102) and a time void or urology evaluation considered (1104). If there is no pad leakage, then a normal study is considered (1106).

FIG. 26 shows a preferred sequence of steps for inpatient processing as compared to that sequence shown in FIG. 25. Some of the sequence steps are similar as shown in FIG. 25. The process starts (1110) and a determination is made if the post void residual is greater than 100 ml (1112). If yes, a determination is made if the resting detrusor pressure is greater than 15 centimeters of water (1114). In this example, if yes, it could signify UMN Bladder or DSD (1116). A urology evaluation occurs (1118) and an outcome considers ICP, Foley catheter placement, ruling out UTI, ruling out bladder outlet obstruction, possible PSA, ruling out bladder outlet obstruction as BPH or pelvic organ prolapse, and considering urology evaluation as indicated (1120). If the voiding detrusor pressure was greater than 60 (1122), a determination is made if there was a pad leak (1124) and if yes, this could correspond to bladder outlet obstruction, overflow incontinence or possible DSD (1126) and the outcome is similar as before (1120). If there is no pad leakage, this can correspond to bladder outlet obstruction and possible DSD (1128) and the same outcome (1120).

If the detrusor pressure was greater than 60 ml at voiding, a determination is made if there is a pad leak (1130) and if yes, this can correspond to overflow incontinence and possible SUI (1132). The outcome can be PVR/ICP, the rule out of UTI, and urecholine if no UTI (1134). If there is no pad leakage, this can correspond to atonic bladder followed by hypotonic bladder consideration (1136). The outcome is as before (1134).

If the PVR was not greater than 100 ml (1112), a determination is made if the detrusor pressure is greater than 15 centimeters of water at resting (1138) and if yes, this can correspond to detrusor instability, urge incontinence and mixed incontinence (1140). UTI is ruled out. Ditropan or detrol is considered if there is no UTI. An SUI evaluation for urology is considered. Males can consider normal pressure hydrocephalus (NPH) (1142).

If the detrusor pressure was not greater than 15 centimeters of water at resting (1138), a determination is made whether there was a pad leak (1144) and if yes, this can correspond to SUI (1146) and the outcome can be a time void and urology evaluation with the time void indicating how much time it takes to void (1148). If not, then a normal study occurs (1150).

As shown by the different considerations and outcomes in FIGS. 23-26, many different possible tests and diagnoses with potential outcomes are possible and the sequence of steps takes the clinician through what is possible. Typically, the data is input into the handheld device and processed with the different scenarios and outcome and an evaluation displayed on the handheld device.

Figure 27:
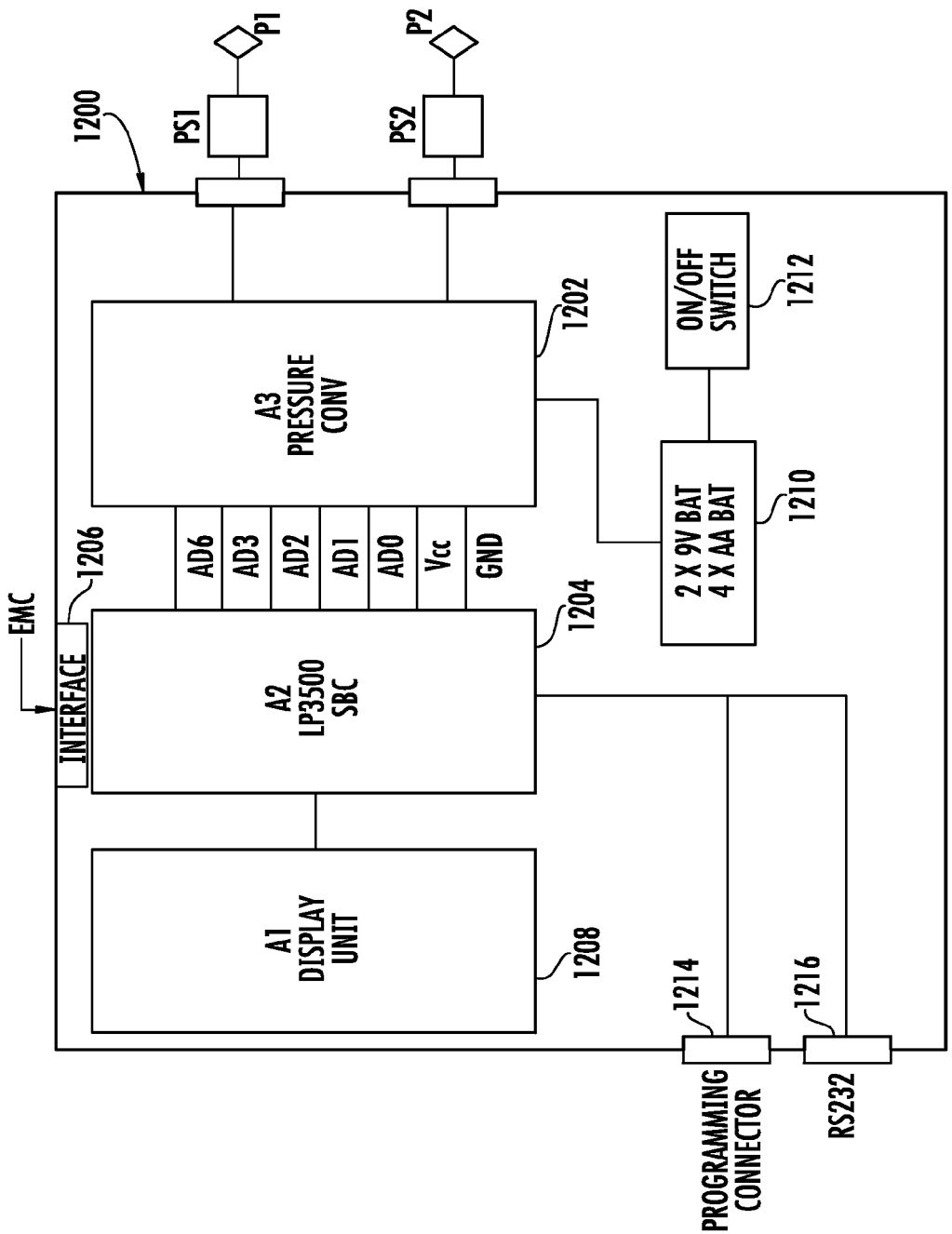
FIG. 27 is a block diagram showing various components that can be used in an embodiment of the handheld device such as described before relative to FIG. 5.

FIG. 27 is a high-level block diagram of basic components for the handheld device illustrated generally in this example at 1200, which in one non-limiting example, uses wireless technology to receive pressure readings such as shown in FIG. 8. This example relative to FIG. 27 shows a wired connection. In this example for the handheld device 1200, the device includes two pressure inputs, for example, to receive Viking connector receptacles and connect to TDOC pressure sensors. As illustrated, the inputs at pressure 1 and pressure 2 correspond to the two respective catheters as inputs through the pressure sensors PS1 and PS2 into a pressure converter circuit 1202, which transmits the pressure signals to the onboard processor 1204 through various AD signal lines as indicated. The pressure converter circuit 1202 includes pressure measurement electronics such as shown in the schematic circuit diagram of FIG. 30 and described in greater detail below. The pressure measurements obtained through the pressure sensors PS1 and PS2 are converted and forwarded to the processor 1204, which in one non-limiting example, is a single board computer such as a Rabbit LP3500. The pressure sensors PS1 and PS2 are in one non-limiting example TDOC-4030 pressure sensors. The catheters used at inputs P1 and P2 correspond in one non-limiting example to TDOC-6F catheters. It should be understood that EMC signals are input through interface circuit 1206 into the processor 1204. Data that is processed is displayed using a display unit 1208 such a display/keyboard/LED, for example a rabbit KDU.

It should be understood that the improved catheter as described below FIG. 31 can be used. In one non-limiting example, the pressure converter circuit 1202 is powered by two nine-volt batteries or in an alternative embodiment by four AA batteries 1210. The batteries are connected to an on/off switch 1212. A programming connector 1214 and RS232 connector 1216 are connected into the processor 1204 to allow programming of the processor with appropriate software and code as described before and for processing data related to the involuntary reflex cough test. Data can be retrieved or input. This device 1200 accomplishes both SUI and neuroanalysis using the appropriate data analysis.

FIGS. 28A-28D are respective plan, front elevation and side elevation views of a housing 1220 that can incorporate the various system components such as shown in FIG. 27 and form the handheld device as described before. The left side elevation view in FIG. 20C shows openings 1222 for receiving Viking connector receptacles that connect to TDOC pressure sensors for the two catheters in this non-limiting example. Of course, during handheld device use, only one catheter has to be used as noted before and is some instances only EMC.

FIG. 28B shows the front elevation view with a programming connector opening 1224 for a nine pin D male connection and the RS232 connector opening 1226 for a nine pin D female in one non-limiting example. The plan view shows enough space and volume to include switch and pressure sensor wiring 1228 and a single board computer 1230 and custom pressure sensor card as described below. The side elevation view and plan view show various battery holder areas 1232 for either a 2.9 volt or a four AA battery holder.

Figure 29:
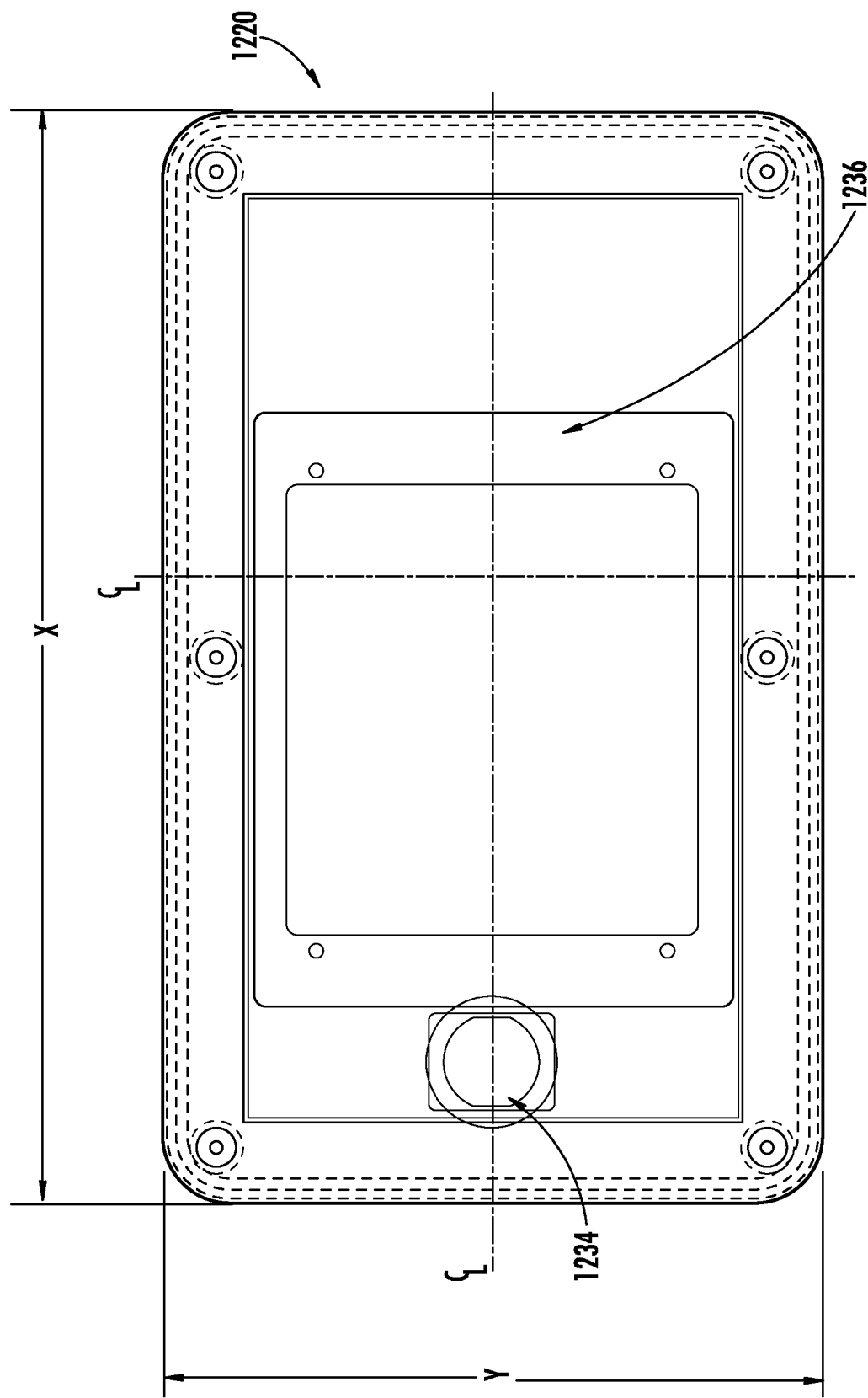
FIG. 29 is a top plan view of a housing cover of the handheld device in accordance with a non-limiting example.

FIG. 29 is a top plan view of the housing 1220 for the handheld device and showing a location for a power on/off toggle switch 1234 and a display with a keyboard and light emitting diodes (LED's) 1236. Non-limiting examples for possible dimensions for the handheld device are about 8 inches (x) and 5 inches (y).

Figure 30:
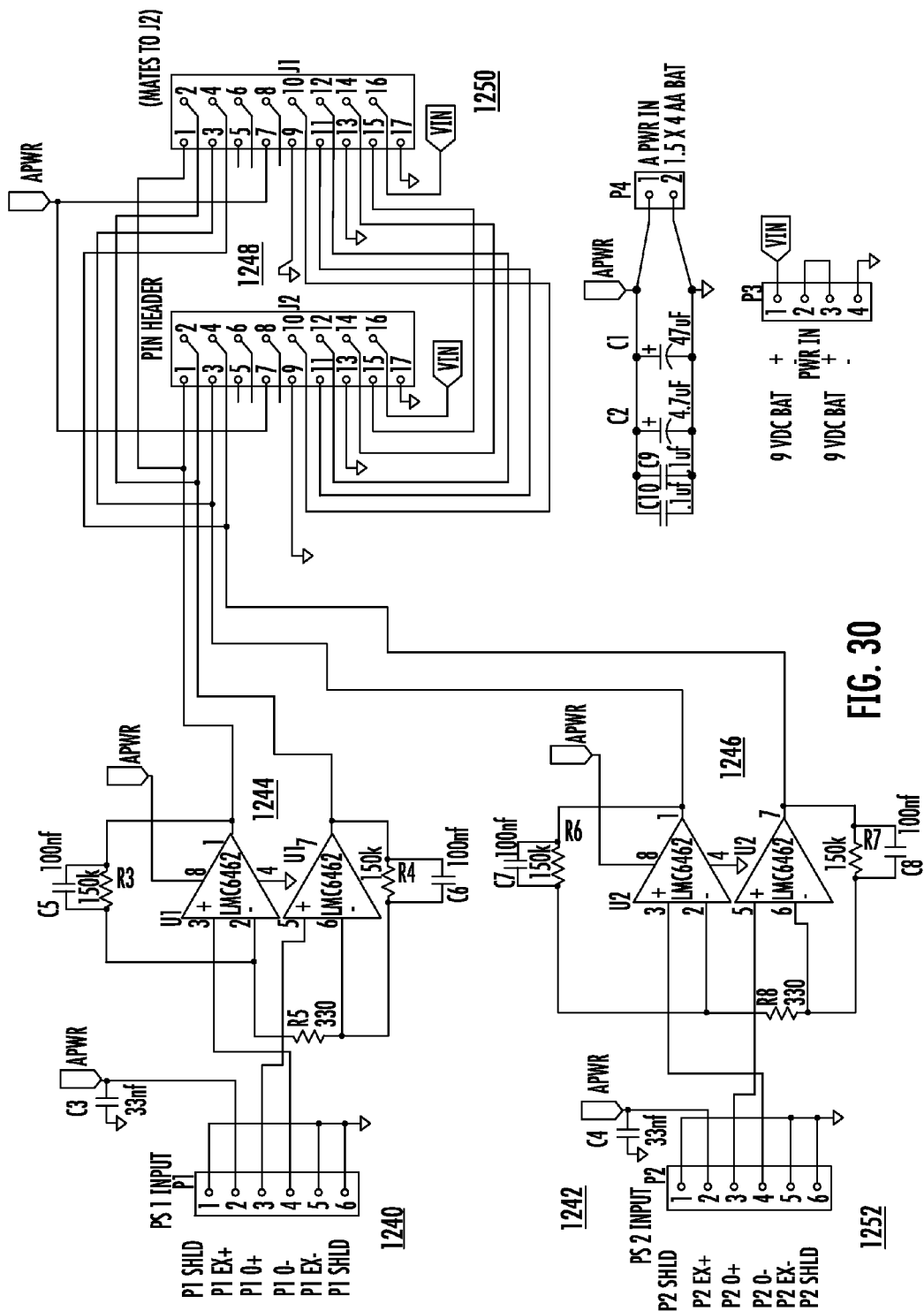
FIG. 30 is a schematic circuit diagram of a representative example of the pressure converter circuit as shown in FIG. 27 that can be used in accordance with a non-limiting example.

FIG. 30 is a schematic circuit diagram of the pressure converter 1252 in accordance with a non-limiting example and showing the various pressure sensor 1 input 1240 and pressure sensor 2 input 1242. These are independent channels each with comparators and operational amplifiers illustrated generally at 1244 and 1246 respectively. These components and circuits connect into appropriate pin headers 1248 and 1250 that output to a single board computer in this non-limiting example.

These examples show use of the pressure sensor as a TDOC-4030 pressure sensor and a catheter as a TDOC-7F (7 French) catheter. The catheter as described below relative to FIG. 31 can be used in a non-limiting example for the measurement.

Different processors 1204 as a single board computer can be used in a non-limiting example. The described Rabbit microprocessor is a low-power, single-board computer and is especially operable with portable handheld, battery-powered, remote monitoring systems. It includes built-in analog and digital input/output and typically consumes less than 20 milliamperes when operational and less than 100 microamps in a power-save mode. In this non-limiting example, it includes flash memory and SRAM and various inputs/outputs and in one non-limiting example eight analog/digital converter inputs with programmable gain and six serial ports. It has pulse width modulation (PWM) outputs. It can be programmed using C software in a non-limiting example.

It should be understood that the display unit 1208 as illustrated in FIG. 27 is a separate display unit that includes the display, keyboard and light emitting diodes and supported on the housing, but could be incorporated integral with the single board computer in a non-limiting example.

Figure 31:
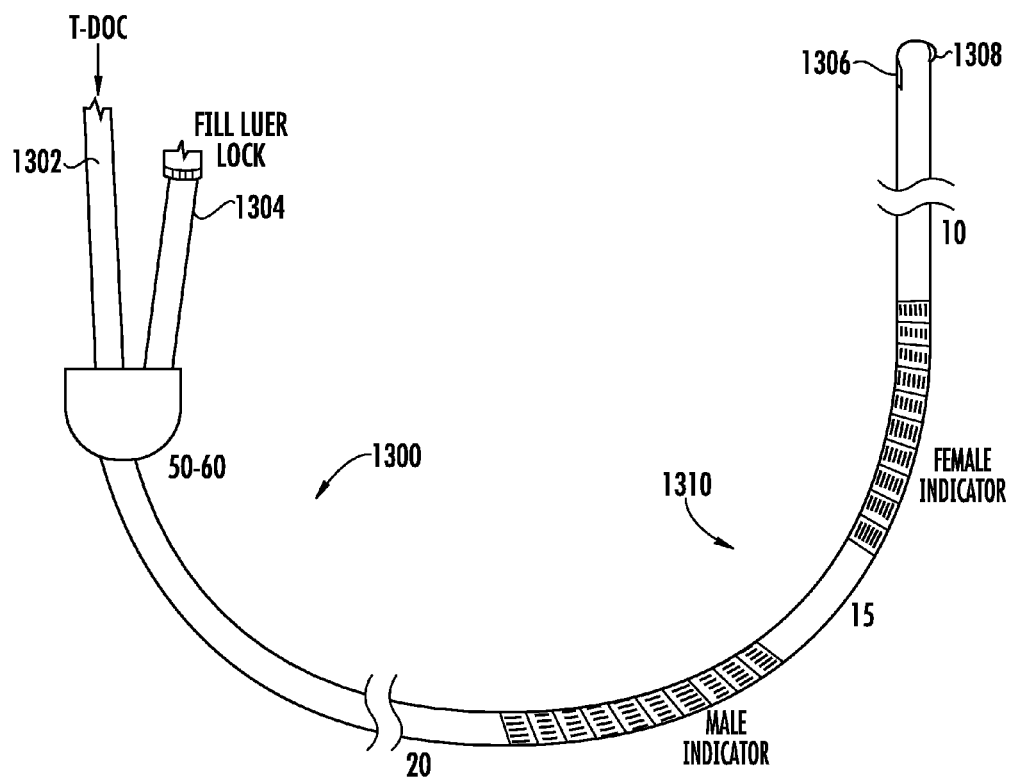
FIG. 31 is a simplified plan view of a catheter that can be used for the urodynamic and medical diagnostic testing in accordance with a non-limiting example.

FIG. 31 is an example catheter 1300 that can be used in accordance with a non-limiting example. It is a urodynamic dual lumen catheter formed from a catheter body as an elongated tube with proximal and distal ends and preferably has a smallest external diameter that can contain two lumens within it. It is typically approximately 50 to about 60 centimeters in length. A first lumen 1302 is used for monitoring bladder activity. In one non-limiting example, it contains a stylet/wire sensor that can be left within the lumen or used alone. A second lumen 1304 permits the filling port to instill fluid into the urinary bladder. The second lumen output is shown at 1306 and a sensor 1308 is positioned at the distal end. This catheter includes a luer lock end for rapid connection to infusion tubing or a syringe, and can accommodate rates of infusion up to 1,200 ml/hr via gravity flow or 15 ml/sec via manual installation. The external surface of the catheter has a surface area that contains areas of indicators along its length shown generally at 1310 that operate as a urine leak detect device. These indicators 1310 change color when exposed to two components in combination in accordance with a non-limiting example. This color change can occur with a temperature about 30 degrees Celsius and the presence of urea in a non-limiting example.

The catheter 1300 is used to evaluate bladder pressures at rest, empty or with urine, filling with fluid during voiding. It is used to evaluate for urinary incontinence by detecting a minimal amount of urine loss during voluntary and involuntary maneuvers of the type as described before. The stylet sensor in one non-limiting example is used alone for pressure monitoring while presenting the least amount of disruption/distortion of the urethra and urinary sphincters. The stylet in another non-limiting example is packaged separately and inserted into an existing Foley catheter to measure pressure and function in one non-limiting example.

In one non-limiting example, the catheter is a dual lumen six French catheter of about 50 centimeters and includes the sensor 1308 and fill port at the second lumen 1304. It is inserted in a non-limiting example about 10 centimeters for a female bladder and 15 centimeters for a male bladder. The location of color change indicators 1310 for a female could be about 11-14 centimeters, and for a male, about 16-19 centimeters. In one non-limiting example, the urine pH range is about 4.6 to about 8.

It should be understood that the catheter is preferably a smaller diameter catheter and includes those down to 3 (three) and 4 (four) French. The smallest catheter possible is used as a urethra catheter and somewhat smaller than a standard ten (10) French catheter. It has been found that some patients have a tendency to leak with the larger catheter in place because of the size of the catheter or they become obstructed with that catheter in place. Smaller urinary bladder catheters are typically about 6 (six) French and used for neonatal infants. There are some PICC catheters (Peripherally Inserted Central Catheters) that are three (3) and four (4) French. These smaller catheters should be double lumen in this example. This system is not limited in size, but the smaller is advantageous.

The double lumen catheter, in accordance with a non-limiting example as described, has the first lumen 1302 for a sensor probe 1308 and a second lumen 1304 for the filling with liquid. The sensor probe is a "T-doc" as used with an air-charged catheter for pressure sensing and air-charged pressure recording in one non-limiting example. It should be understood that this catheter can be used with or without filling the bladder, and advantageously used in urodynamic testing. The doctor, nurse or clinician does not have to personally bend down and view the urethra area to determine if there is leakage, which is an advantage in a clinical test. Different types of indicators 1310 as chemical indicators can be used.

Figure 32:
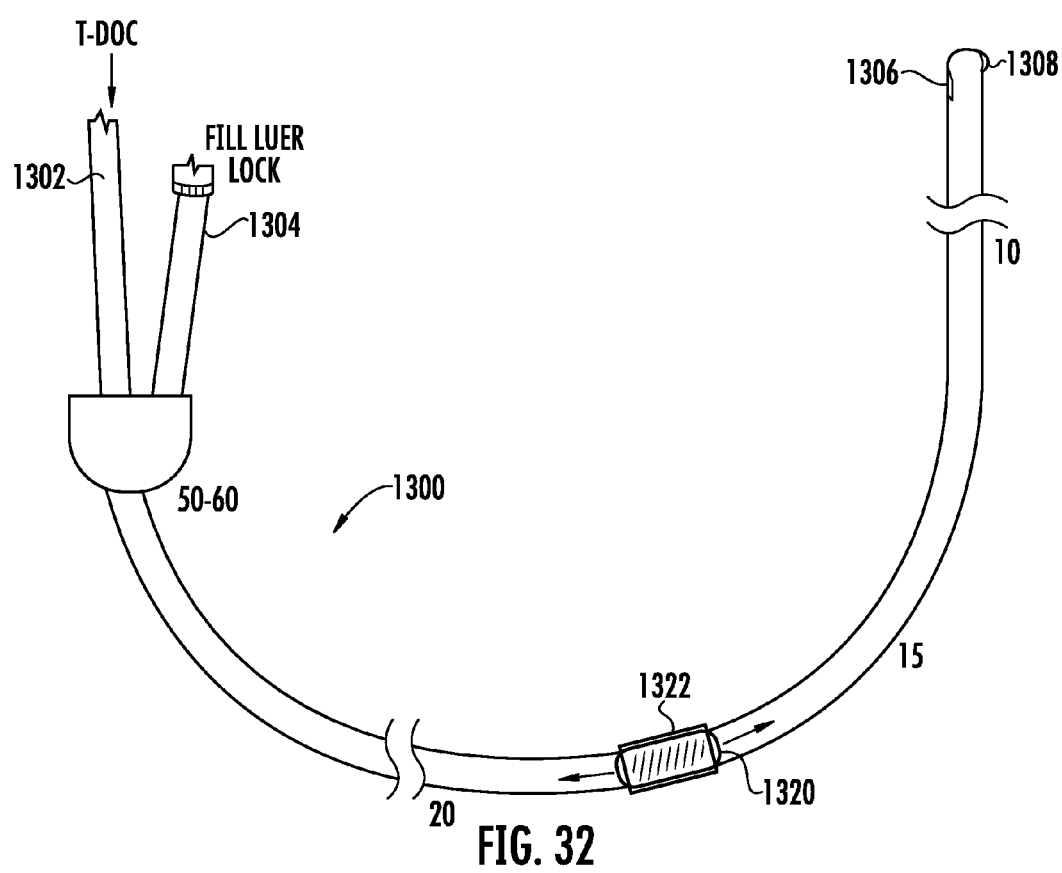
FIG. 32 is another simplified plain view of another example of a catheter similar to that shown in FIG. 31 that can be used for the urodynamic and medical diagnostic testing in accordance with a non-limiting example.

In another non-limiting example such as shown in FIG. 32, the catheter includes a support ring 1320 such as a silastic ring that holds a urine-indicating pad or other enzymatic pad 1322 and is affixed to the catheter as a single unit wherein the catheter that measures the intravesicular pressure. The silastic ring 1320 carries a color changing pad in this example instead of using color indicators 1310 positioned along the catheter surface as in the example of FIG. 31. This also provides for a urinary leakage indicator. The support ring 1320 slides on the catheter in one example. It is permanently affixed to the catheter, but adjustable in this example. A moisture indicating dye is used in an example on the pad 1322 positioned on the ring 1320. An example of a dye is disclosed in U.S. Pat. No. 4,327,731 as a moisture indicator, and in one aspect could be an enzyme catalyst.

Different types of pads or substrates could be used in combination with the support ring 1320 and moveable along the catheter. This combination catheter and the urine indicating sensor, in one example, are specific for use to determine an instance of stress urinary incontinence. It is possible, however, to add a balloon to this catheter similar to a Foley catheter such that the catheter remains in place. Two catheters are thus possible. For example, a specific catheter and urine indicator are used for stress urinary incontinence. It is also possible to add a balloon with the larger 14, 16, 18 or 20 French catheters as a larger size. A sensing system is included in this example. Added to this catheter is a channel for urine drainage, the sensor, and an indwelling balloon to keep it in place. The catheter, in one example, is used to determine whether the patient can protect their airway in conjunction with the involuntary reflex cough test (iRCT).

The cloth or pad 1322 is attached to the support ring 1320 and includes on the pad a regent that is permanently attached. It can be a single use catheter for stress urinary incontinence (SUI) testing. It is included within the test kit to be described in one example and includes the nebulizer (and the drug) for involuntary reflex cough testing as described before.

In one example, it is possible to have a catheter of about three (3), four (4), or five (5) or somewhat larger French that thread inside a regular Foley catheter with pressure measurement capability. The catheter that goes inside the urethra, such as a seven (7) French catheter, can go inside a Foley catheter. In one example, the balloon is part of the smaller catheter and measures or tests for airway protection in the technique as described before.

An enzymatic moisture detector can be used. Initially, any indicators or pad and ring could be covered before catheter use. When needed, the catheter is uncovered and moved into the proper position against the meatus. A first catheter is used with stress urinary incontinence and testing. Another catheter as a second or larger diameter catheter is balloon specific for reflex cough testing to measure intra-abdominal pressure in determination of airway protection.

In an example, temperature is used with the sensor and changes the sensor as an indicator. It is possible to use the presence of urea for sensing urine. One problem is in bladder testing. The bladder is often filled with saline water or other fluid that is not urine. If the indicator is specific to ammonia or urea, then it would not indicate adequately. Temperature is one advantageous solution and a material that is sensitive to temperature change of about 90 degrees is adequate. The fluid is inserted into the bladder and becomes warmer than room temperature. If there is leakage, it changes the color of the catheter even without the presence of urea.

The tip of the catheter can be placed into the urethra and the outside of the catheter includes the indicator. It changes color if there is leakage whether there is urine inside the bladder or just fill. It could change the color of liquid after it leaks. This could be an assurance against false positives such as would occur with perspiration from the doctor's or nurse's hands. If there is a second testing such as in surgery (and the patient hopefully fixed), a different color could be used. In SUI testing, the liquid is placed in the bladder in one example, but would come out a different color when it reacts with the sensor on the bladder near the meatus. This assures that one is viewing a leakage and not a false positive.

There is a possibility for measuring airway using the port in combination. The catheter can be small enough to go into a side port of a Foley catheter similar to a guide wire. Thus it is possible to take the catheter out if it is obstructing in some way and leave a guide wire. It is possible to remove the catheter and still have a guide wire or small catheter that has a sensor probe on the end. Instead of having a dual channel and having a tube inside a tube that you could do a fill around, it is possible to remove the outside tube that is blocking the urethra. It should be understood that the catheter (depending on size and pathophysiology of a patient) can either block the urethra or hold the urethra open, causing additional leakage. Specific catheter designs as described alleviate these problems. With the larger catheters, the larger catheter size is used to fill and is taken out. The inside tube (catheter) stays. A smaller four (4) French catheter has a dual channel, one for the pressure sensor and the other to fill 1200 millimeters an hour and is adequate to cover different possibilities.

Figure 33:
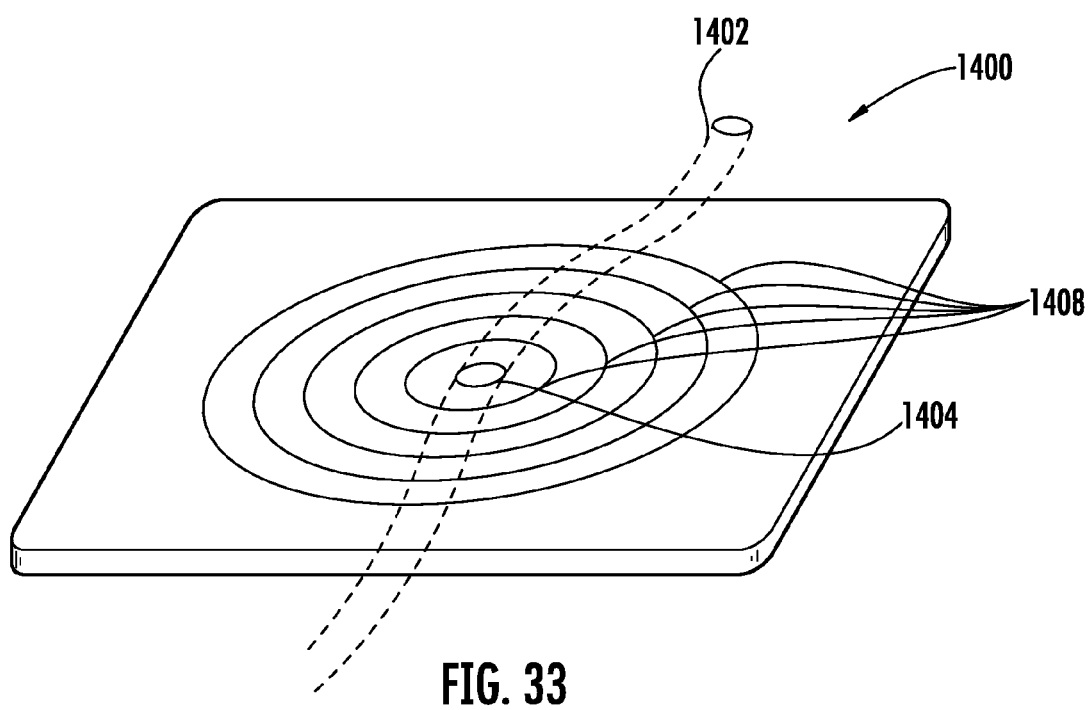
FIG. 33 is an example of a urinary incontinence pad that can be used with a urodynamic catheter and showing pad areas that indicate color change for leakage.

FIG. 33 shows an embodiment of a color changing urinary pad 1204 that can be used with a catheter such as described before. The color changing urinary incontinence pad 1400 is used in conjunction with a catheter 1402 and has a small relief cut-out (hole) 1404 in the middle of the pad where the catheter enters. The pad is placed against the underside near the urethra of a female typically and the catheter enters the urethra and extends through the hole in the center of the urinary incontinence pad for fluid flow and testing purposes. The pad could be taped to the underside in the crotch area. For example, when the involuntary reflex cough test is given and the catheter is inserted through the urethra, the patient is prone to leak urine in some examples. This pad includes concentric rings 1408 around the center catheter cut-out at preferred 10 millimeter intervals for a target area of 50 millimeters. In one non-limiting example, a nitrogen-ammonia (NH3) region is used to identify positively the presence of urine on the pad. The target intervals of 10 millimeters each are used to determine how much leakage and incontinence occurs during, for example, a reflex or involuntary cough test as described before. The different concentric areas have different amounts of reagent in a non-limiting example or different reagents to allow different color changes at the spaced intervals depending on the amount of urine leakage.

Figure 34:
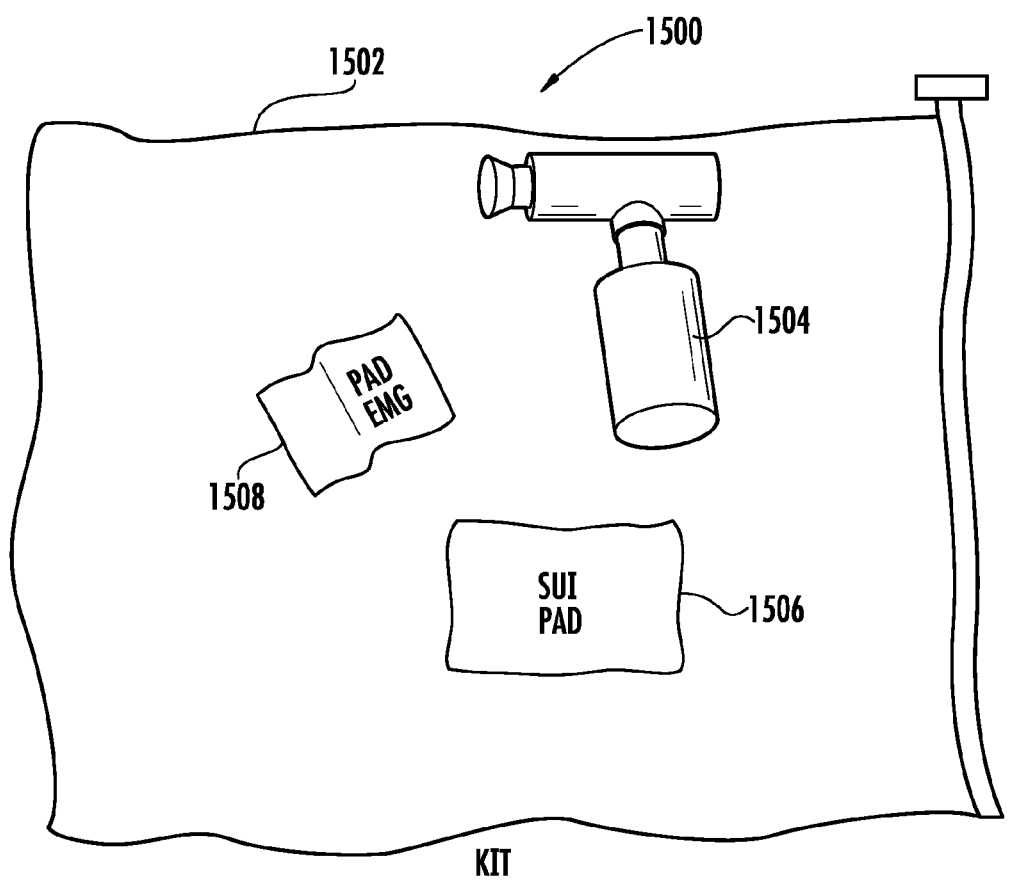
FIGS. 34 and 35 are fragmental drawing views showing examples of kits that can be used in accordance with a non-limiting example.
Figure 35:
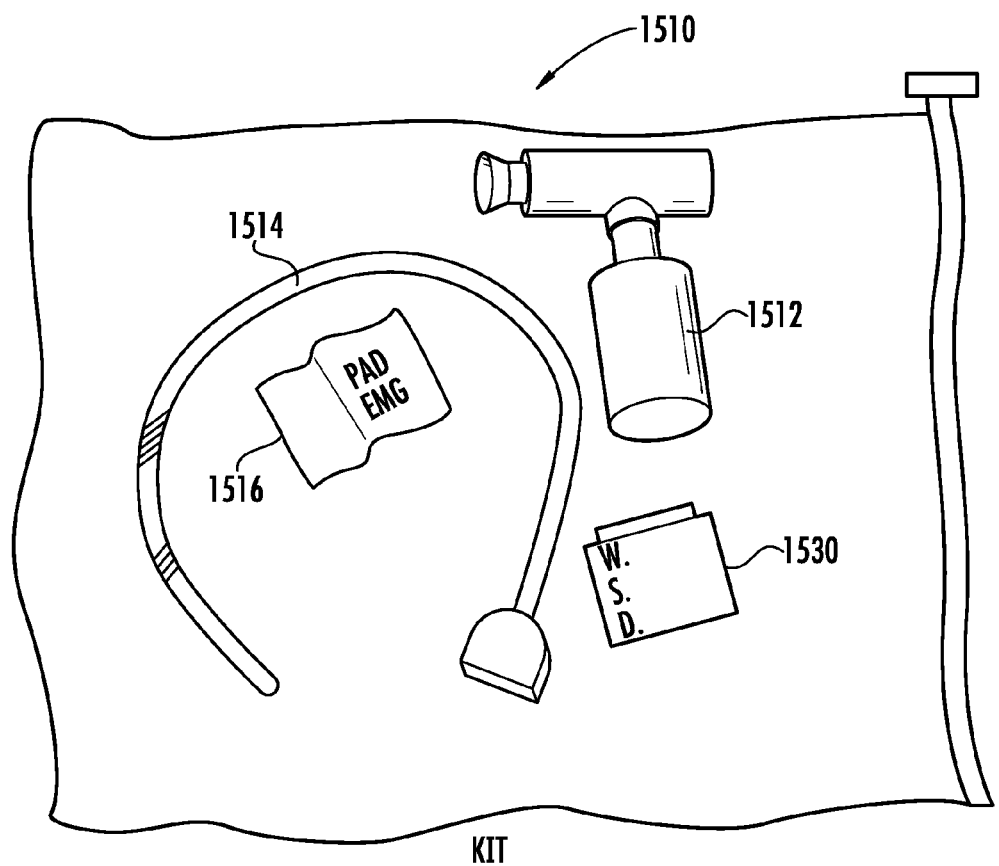

FIGS. 34 and 35 show example kits that can be used in accordance with a non-limiting example. A first kit 1500 shown in FIG. 34 includes a package or housing 1502 or other housing that holds the kit component. A nebulizer 1504 includes the drug for the tartaric acid and a urinary incontinence pad 1506 and an EMG pad 1508 to be placed at paraspinal. A second kit 1510 is shown in FIG. 35 and includes the nebulizer 1512 and a catheter 1514 such as described relative to FIG. 31, although different types of catheters can be used. An EMG pad 1516 is illustrated. The kits are contained in self-contained housings or packages 1502 with a quick-release. The various components as described are throw away components, except the processing device. The kit could include any necessary connector leads that connect into the handheld device.

Any catheter could include a wireless sensing device 1530 that is included in the kit in case wireless technology is used. Although a wireless sensing device could be separately connected to the catheter after the kit is opened, in one aspect, it is possible to include the wireless sensing device connected to any appropriate catheter such that the kit is open, the nebulizer removed, any pad and the catheter with wireless sensing device. The handheld device can be a separate device and the catheter used and wireless signals sent to the handheld device. After analysis and testing on a patient, the kit components such as the catheter and wireless sensing device, pads and nebulizer could be disposed of in the proper manner. It is possible that the EMG pads could connect into the wireless sensing device such that wireless signals are transmitted to the handheld device that includes the pressure readings and the EMG signals. Thus, the kit or system when removed would include the pressure sensing device with the attached leads and EMG pad and catheter that may be integrated together or separately removed and then connected to each other.

Figure 36:
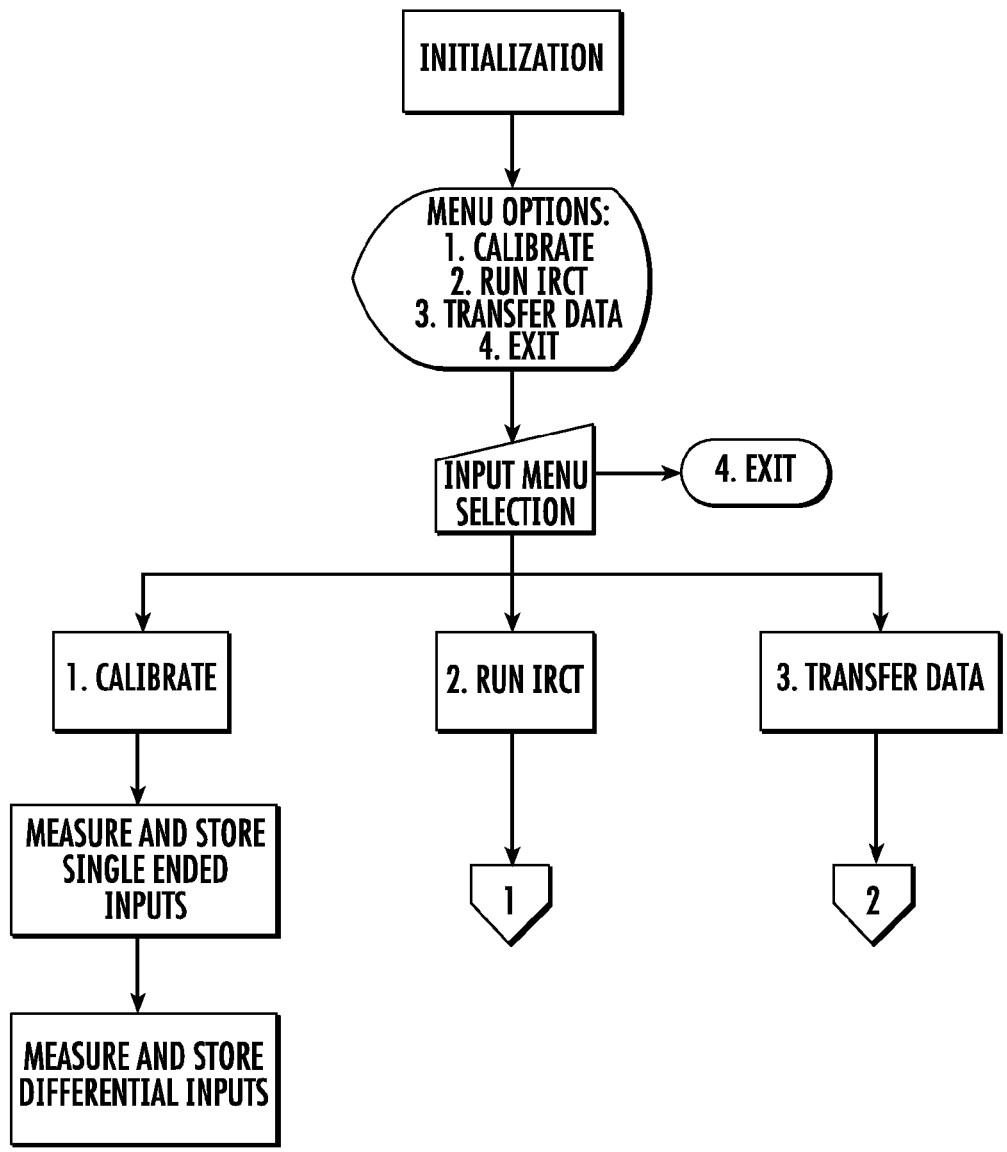
FIGS. 36-38 are a top level functional diagram for the operation of the handheld device in which the analysis algorithm of FIGS. 23-26 are illustrated as a block on FIG. 37.
Figure 37:
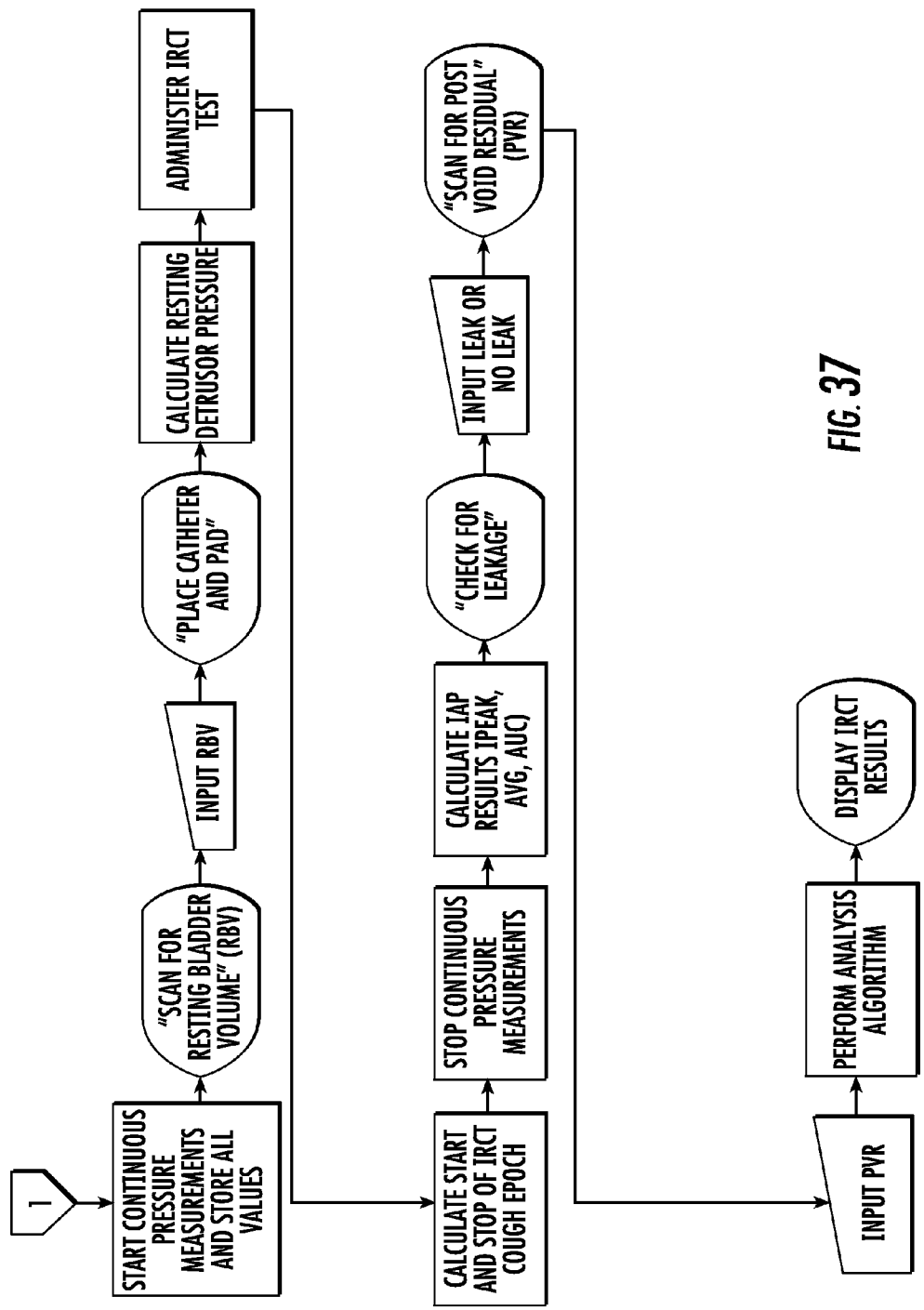
Figure 38:
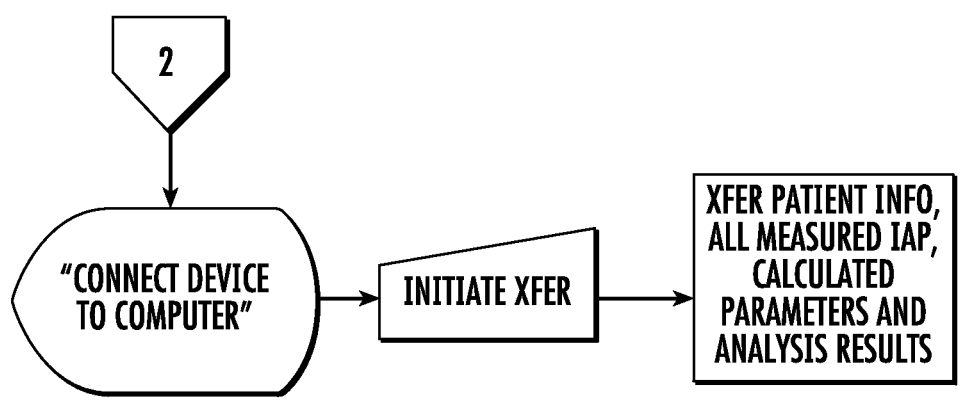

FIGS. 36-38 are flowcharts for the top level functions for processing that can occur in the handheld device as described relative to FIGS. 4-8, 27-30 and 39-42. The different functional menu options in FIG. 36 after initialization include calibrate (1); running the involuntary reflex cough test (2); and transferring data (3) as illustrated with the numbered alternatives that are input as a menu selection, followed by Exit (4). FIG. 37 shows the sequence for the running of the involuntary reflex cough test (iRCT) and the performing of the analysis algorithm corresponding to FIGS. 23-26. FIG. 38 illustrates a sequence that can be used for the transfer of data.

Calibration as shown in FIG. 36 typically includes the measuring and storing of the single ended inputs and the measuring and storing of the differential inputs. Running the involuntary reflex cough test begins as shown in FIG. 37 in which continuous pressure measurements are started and all values stored. The display on the handheld unit typically will show "Scan For Resting Bladder Volume" (RBV). The RBV is input into the device, which then displays "Place Catheter and Pad," indicating that the clinician, nurse or doctor should place the catheter and pad at the proper location such as an EMG pad and urinary or other catheter as described before. The resting detrusor pressure is calculated, and the involuntary reflex cough test is administered. The start and stop of the involuntary reflex cough test cough epoch is calculated, and continuous pressure measurements are stopped. The intra-abdominal pressure (IAP) results, the peak, the average, and the area under the curve (AUC) are calculated. In an example, the display will state "Check for Leakage" to determine if there has been urine leakage. The user of the handheld device would then input "Leak" or "No Leak" as an option at the handheld device and the display would state "Scan For Post Void Residual" (PVR). The PVR is input and the analysis algorithm corresponding to the algorithm described relative to FIGS. 23-26 is run. The iRCT results are then displayed on the handheld device.

At this time, data can be transferred as explained in the sequence of FIG. 38, in which the device display would recite "Connect Device to Computer" as a non-limiting example, indicating that a wireless or wired connection can be made to a computer for further processing. The transfer is initiated and any patient information, such as all measured IAP, calculated parameters and analysis results are transferred.

Figure 39:
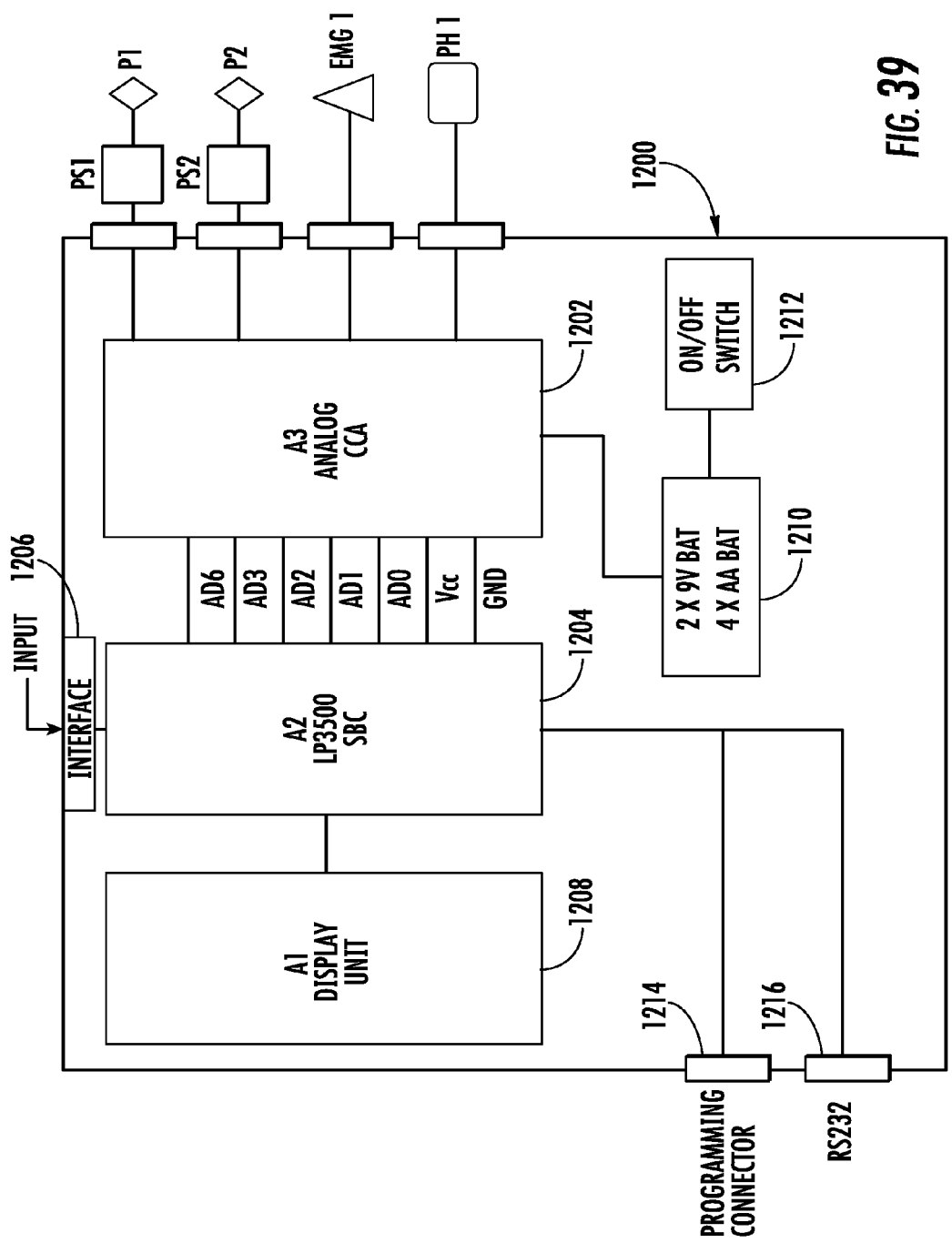
FIG. 39 is a block diagram showing various components that can be used in an embodiment of the handheld device, but showing the four channel system with two pressure inputs, an EMG input, and a pH input, similar to that shown in FIG. 27.
Figure 40:
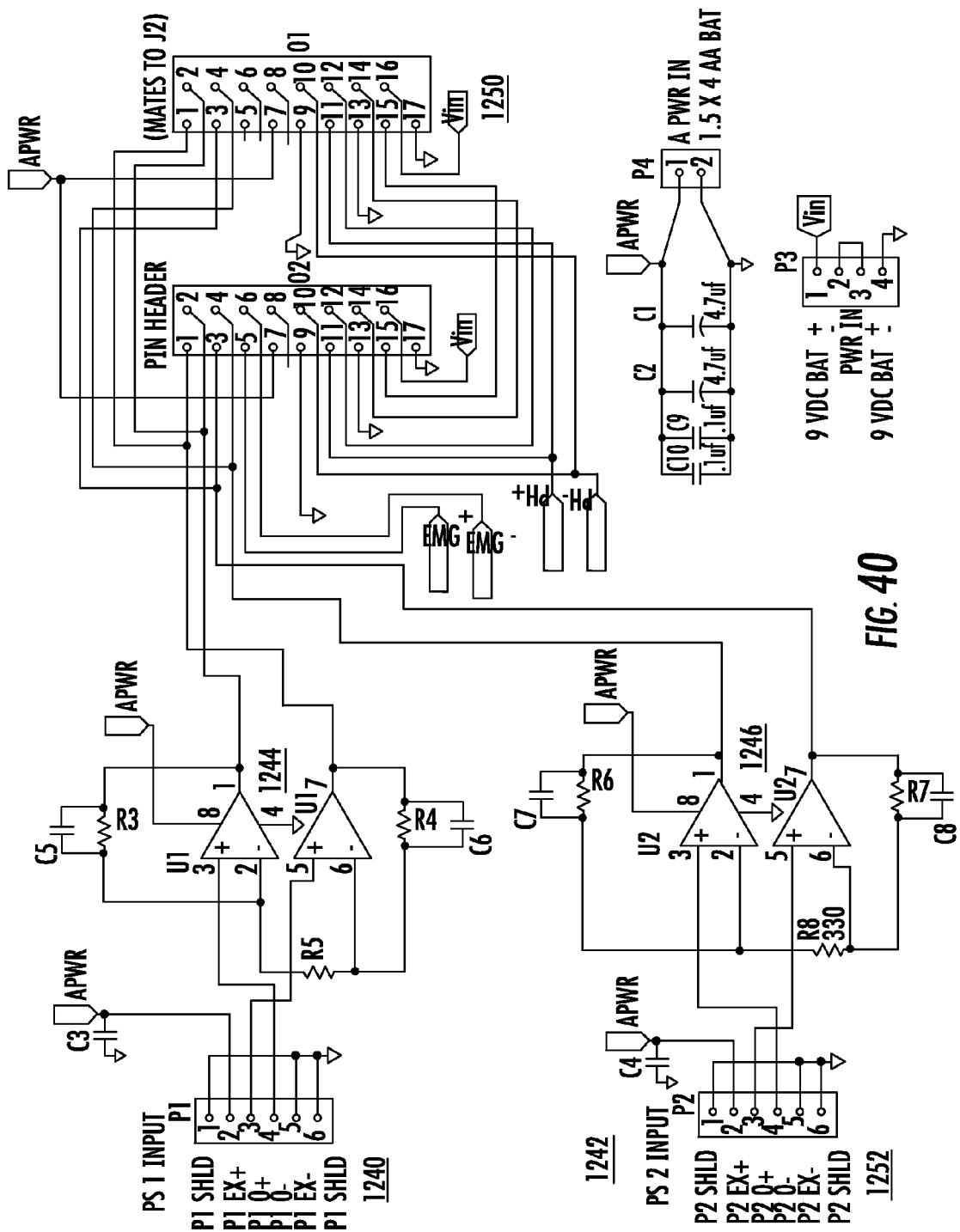
FIG. 40 is a schematic circuit diagram of a representative example of a four-channel circuit similar to that shown in FIG. 30.

Circuit components for the handheld device as an example are now described with further enhancements. The block diagram and schematic circuit diagram of FIGS. 39 and 40 are similar to the block diagram and schematic circuit diagram of FIGS. 27 and 30 for the handheld device, but instead there is now shown a four channel system in which not only pressure for P1 and P2 are measured, but also measurements are taken for EMG (EMG1) and pH (PH1) such as for reflux measurement, using the device and catheters as will be described relative to FIGS. 51-53. Similar reference numerals are used in this description of components in FIGS. 39 and 40 as used with FIGS. 27 and 30, although the interface 120b shows a general input reference, which could be another EMG, pressure, pH, or other similar input, including a spare channel.

Figure 41:
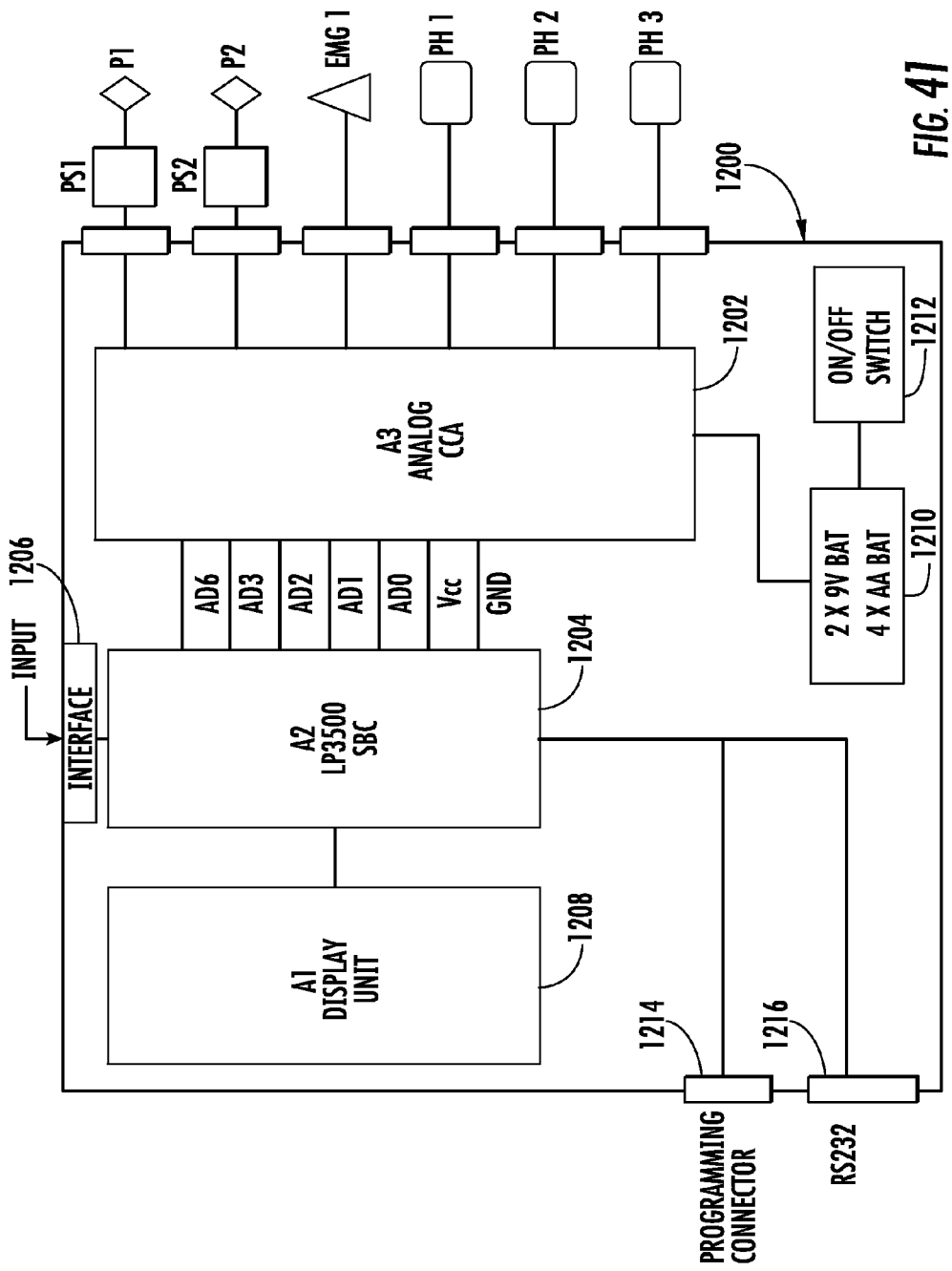
FIGS. 41 and 42 show respective six-channel systems, including a schematic circuit diagram in FIG. 41 and the block diagram in FIG. 40 for a six-channel system.
Figure 42:
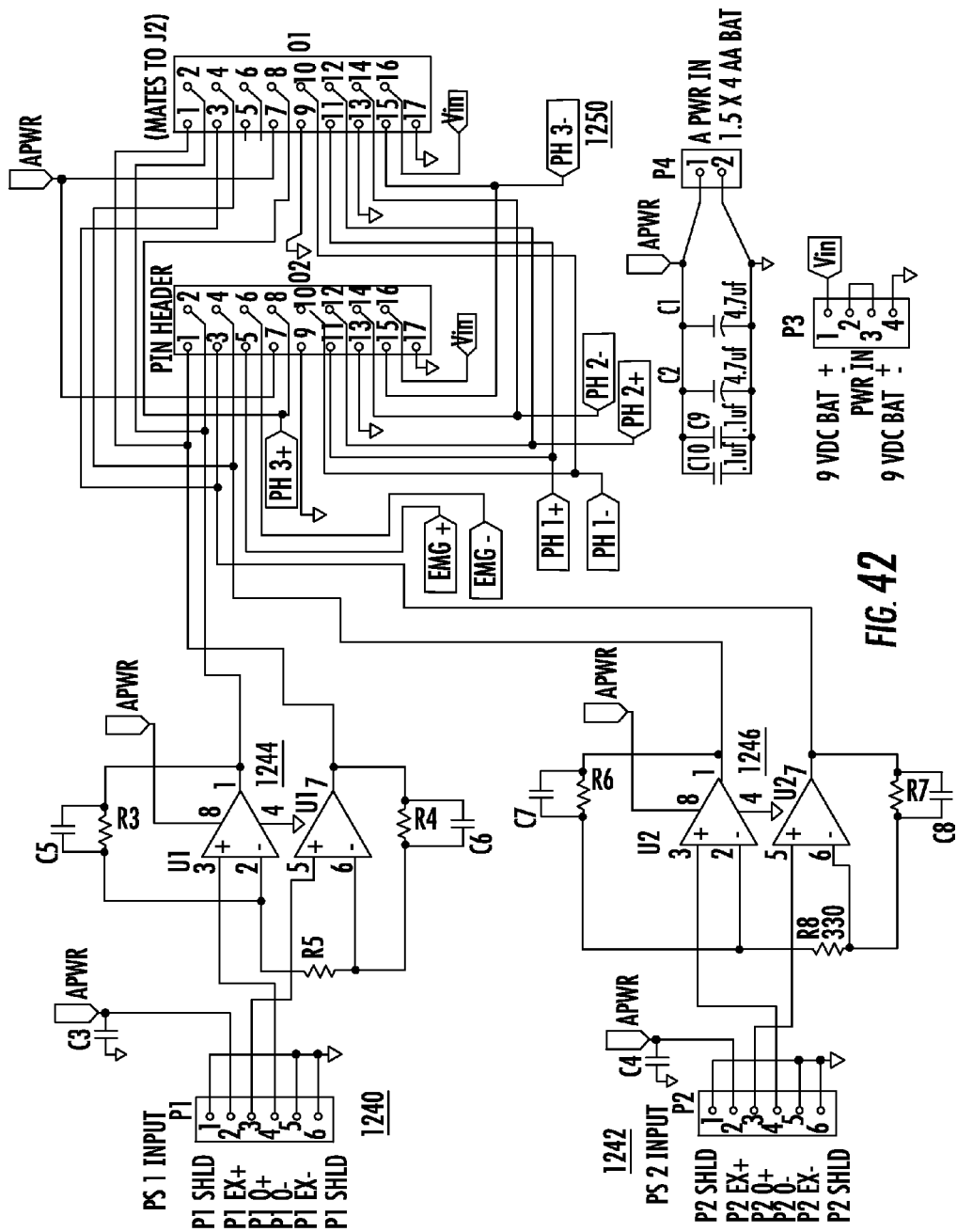

FIGS. 41 and 42 show a six channel system in which three pH inputs are illustrated, for example, for measuring pH, for example, when pH probes are situated on a device (FIGS. 51-53) and pH probes or sensors are located in the stomach, at the lower esophageal sphincter (LES), mid-esophageal area, and/or superior esophageal area. It should be understood that an eight channel system can also be used in which there may be four pH channels for the four locations as described, two pressure channels and two EMG channels. One of the channels, in the alternative, could be a spare channel. The particular choice of channels is a choice of one skilled in the art and what is being analyzed.

In an example, the EMG sensor circuit could incorporate a DELSYS DE-2.1 and the pH measurement probe could incorporate a MediPlus 25100 as non-limiting examples. The pressure sensor could be a TDOC-4030 for PS1 and PS2 and the catheter function as P1 and P2 could be a TDOC-7F.

There now follows an example of a pseudocode, which explains in a more cogent manner the function of the programming code that could be used with the handheld device as described in accordance with a non-limiting example:

```
/****************************************************************************
Function    : Init_Arrays
Description : Initializes all the arrays to predefined values deemed as having no
valid meaning.
****************************************************************************/
Init_Arrays( )
    While (index <NUM_ENTRIES)
        VesicularPressure[index]= UNDEF_PRESSURE
        AbdominalPressure [index]= UNDEF_PRESSURE
        DetrusorPressure [index] = UNDEF_PRESSURE
        index = index + 1
    End While
End    // Init_Arrays
/****************************************************************************
Function    : Calculate_Pdet_Array
Description : Calculates the DetrusorPressure values throughout the cough event and
populates the array accordingly.
****************************************************************************/
Calculate_Pdet_Array( )
    index = CoughStart
    While (index <=CoughStop)
        DetrusorPressure [index]= VesicularPressure [index] – AbdominalPressure [index]
        index = index + 1
    End While
End    // Calculate_Pdet_Array
/****************************************************************************
Function    : Normalize_Event_Array
Description : Normalizes the Pves for the duration of the cough event only, by
subtracting the baseline pressure from every Pves value.
****************************************************************************/
Normalize_Event_Array( )
    index = CoughStart
    While (index <=CoughStop)
        VesicularPressure [index]= VesicularPressure [index] – BaseLinePressure
        index = index + 1
    End while
End    // Normalize_Event_Array
/****************************************************************************
Function    : Average_Pressure
Description : Calculates the average value of an array subset.
****************************************************************************/
Average_Pressure( )
    Sum = 0;
    index = CoughStart
    While (index <=CoughStop)
        Sum = Sum + VesicularPressure [index]
        index = index + 1
    End While
    AveragePressure = Sum/( CoughStop – CoughStart + 1)
End    // Average_Pressure
/****************************************************************************
Function    : Peak_Pressure
Description : Finds the peak value of an array subset.
****************************************************************************/
Peak_Pressure( )
    PeakPressure = UNDEF_PRESSURE
    index = CoughStart
    While (index <=CoughStop)
        If (VesicularPressure [index]>= PeakPressure)
            PeakPressure = VesicularPressure [index]
        End If
        index = index + 1
    End While
End    // Peak_Pressure
/****************************************************************************
Function    : Find_Level_Pressure
Description : Searches a subset of the pressure array for a window where the pressure
is "relatively" level.
****************************************************************************/
Find_Level_Pressure( )
    index = 0
    While (index < NUM_ENTRIES)
        Calculate Slope between VesicularPressure [index] and VesicularPressure
```

```
                [index+1]
                        If (Slope < SlopeTolerance)
                                If (Duration > XTime) )
                                        Stop = index−1
                                        Escape While
                                End If
                        End if
                        index = index + 1
                End While
End   // Find_Level_Pressure
/*********************************************************************
Function      : Event_Start
Description   : Determines the start point for a cough event by examining the slope
between consecutive points.
*********************************************************************/
Event_Start( )
        index = 0
         While (index < NUM_ENTRIES)
                Calculate Slope between VesicularPressure [index] and VesicularPressure
[index+1]
                If (Slope > SlopeTolerance)
                        If (Count > ConsecutiveTimes)
                                                Start = index
                                        Escape While
                                End If
                                Count = Count + 1
                        End if
                index = index + 1
                 End While
End   // Event_Start
/*********************************************************************
Function      : Event_End
Description   : Determines the end point for a cough event by examining the slope and
determining if the pressure has remained relatively unchanged for a certain length of
time.
*********************************************************************/
Event_End( )
                Stop = Find_Level_Pressure( )
End   // Event_End
/*********************************************************************
Function      : Boundarize_Event
Description   : Determines the start and end points for a cough event.
*********************************************************************/
Boundarize_Event( )
        CoughStart = Event_Start( )
        CoughStop = Event_End( )
End   // Boundarize_Event
/*********************************************************************
Function      : Baseline_Pressure
Description   : Determines the baseline pressure for a cough event by looking for a
relatively flat pressure for at least a 2 second window prior to the cough event.
*********************************************************************/
Baseline_Pressure( )
        Start = 0;
        Average = Average_Pressure( )
        Stop = Find_Level_Pressure(Average)
        If (Stop > (Start + 2 seconds))
                Start = Stop − 2 seconds
        End If
        BaseLinePressure = Average_Pressure(Start,Stop)
End   // Baseline_Pressure
/*********************************************************************
Function      : Calibrate
Description   : Allow the user to calibrate the pressure sensors. If voltage levels are
too low the program will exit.
*********************************************************************/
Calibrate( )
        Voltage = ReadAnalogVolts( )
        If (Voltage < 14.0)
                Display("Please replace 9V batteries!")
                Exit Program
        Else If (Voltage >= 14.0)
                Voltage = ReadAnalogVolts( )
                If (Voltage < 6.0) {
                        Display("Please replace AA batteries!")
                        Exit Program
                End If
                Display ("Connect pressure sensors and place in OPEN position.")
                Vp1cal = ReadAnalogDiff(Channel0)
```

-continued

```
                Vp2cal = ReadAnalogDiff (Channel2)
                Display ("Unit calibrated. Close both pressure sensors.")
        End If
End       // Calibrate
/*******************************************************************************
Function    : In_Patient_Physiology
Description : Performs the inpatient physiology algorithm.
*******************************************************************************/
In_Patient_Physiology(void)
    If (PostVoidResidual > 100.00)
        If (RestingDetrusorPressure > 15.00)
            dispLedOut(RED)
                    // UMN Bladder
                    // Detrusor/sphincter dyssynergia (DSD)
                    // UROLOGY EVAL
        Else If (RestingDetrusorPressure <= 15.00)
            If (MaxVoidingDetrusorPressure > 60.00)
                If (PatientLeaked)
                    dispLedOut(YELLOW)
                            // Bladder Outlet Obstruction (BOO)
                            // Overflow incontinence
                            // Possible DSD
                Else
                    dispLedOut(YELLOW)
                            // Bladder Outlet Obstruction (BOO)
                            // Possible DSD
                End If
            Else If (MaxVoidingDetrusorPressure <= 60.00)
                If (PatientLeaked)
                    dispLedOut(YELLOW)
                            // Overflow incontinence
                            // Possible SUI
                    Else
                    dispLedOut(YELLOW)
                            // Atonic bladder
                            // Hypotonic bladder
                    End If
            End If
        End If
    Else If (PostVoidResidual <= 100.00)
        If (RestingDetrusorPressure > 15.00)
            dispLedOut(YELLOW)
                    // Detrusor instability
                    // Urge incontinence
                    // Mixed incontinence
        Else If (RestingDetrusorPressure <= 15.00)
            If (PatientLeaked)
                dispLedOut(YELLOW)
                        // SUI
            Else
                dispLedOut(GREEN)
                // Normal Study
            End If
        End If
    End If
End   // In_Patient_Physiology
/*******************************************************************************
Function    : Run_RCT_Test
Description : Performs the steps to run the RCT test.
*******************************************************************************/
Run_RCT_Test( )
    RestingBladderVolume = SetBladderVolume("Please scan and enter RBV: ")
    Display ("Please place the catheter)
    Display ("Please place the pad")
     Start measuring to establish baseline and DetrusorPressure
    Calculate Resting DetrusorPressure for 30 seconds
    Display ("Please perform iRCT test)
    PostVoidResidual = SetBladderVolume("Please scan and enter PVR: ")
    PatientLeaked = VerifyLeak("Did patient leak (Y/N)?")
    Stop measuring pressures
    Baseline_Pressure( )
    Boundarize_Event( )
    PeakPressure = Peak_Pressure( )
    Average = Average_Pressure( )
    Calculate AreaUnderCurve
```

```
        In_Patient_Physiology( )
        Display ( PeakPressure , Average, AreaUnderCurve)
End    // Run_RCT_Test
//----------------------------------------------------------------------
// Main program runs the display with menu.
//----------------------------------------------------------------------
main ( )
        Initialize all hardware and parameters
        Init_Arrays( );
        while (Not Exit)
                Get MenuOption from the user
                If (MenuOption = 1)
                        Calibrate( )
                Else If (MenuOption = 2)
                        Run_RCT_Test( )
                Else If (MenuOption = 3)
                        Download measured and calculated data
                Else If (MenuOption = 4)
                        Exit Program
                End If
        End While
End    // main
```

Figure 43:
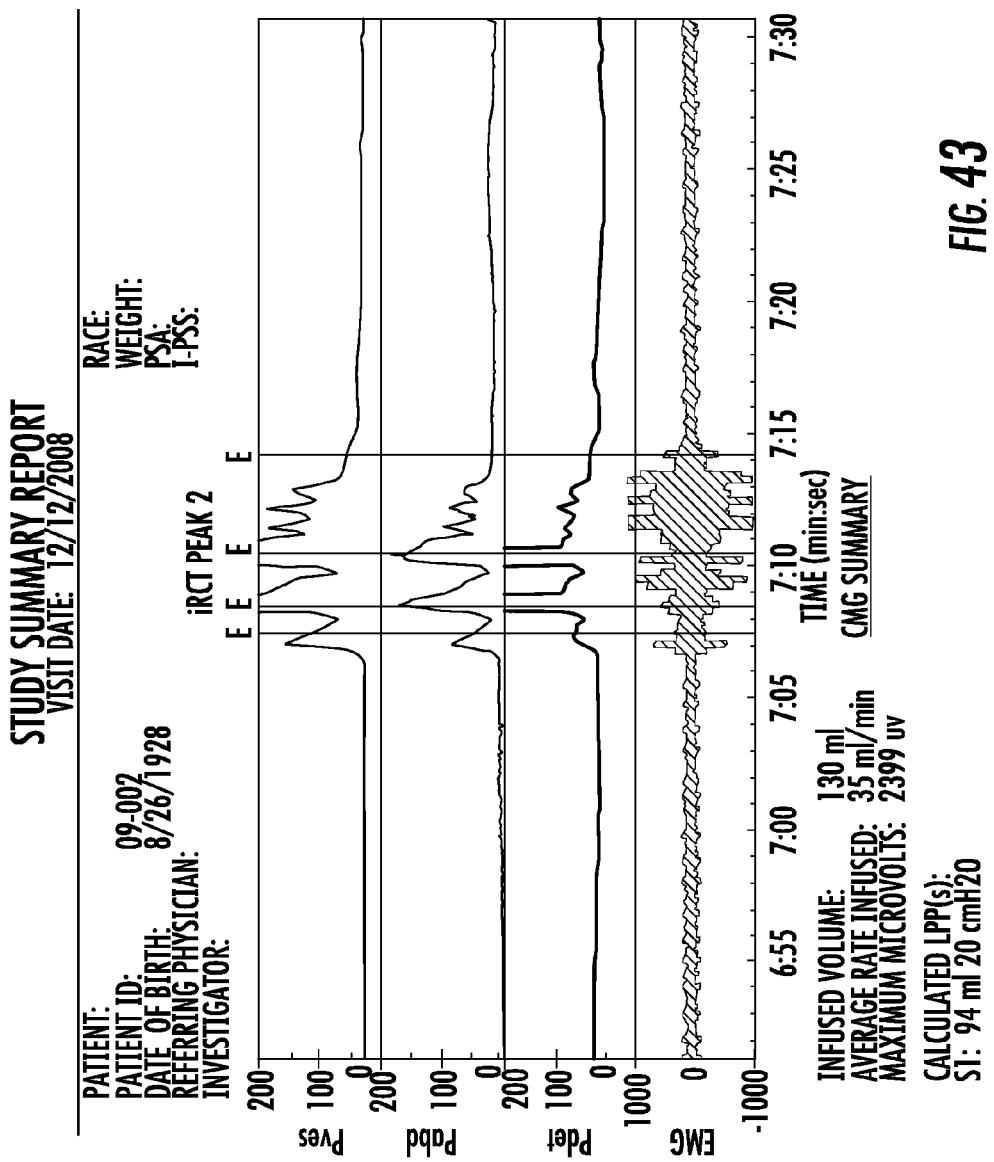
FIGS. 43 and 44 are graphs for the involuntary reflex cough test for a subject demonstrating neuro decline over a 1.5 year period in which the marked decline in iRCT measured variables helps determine medical management.
Figure 44:
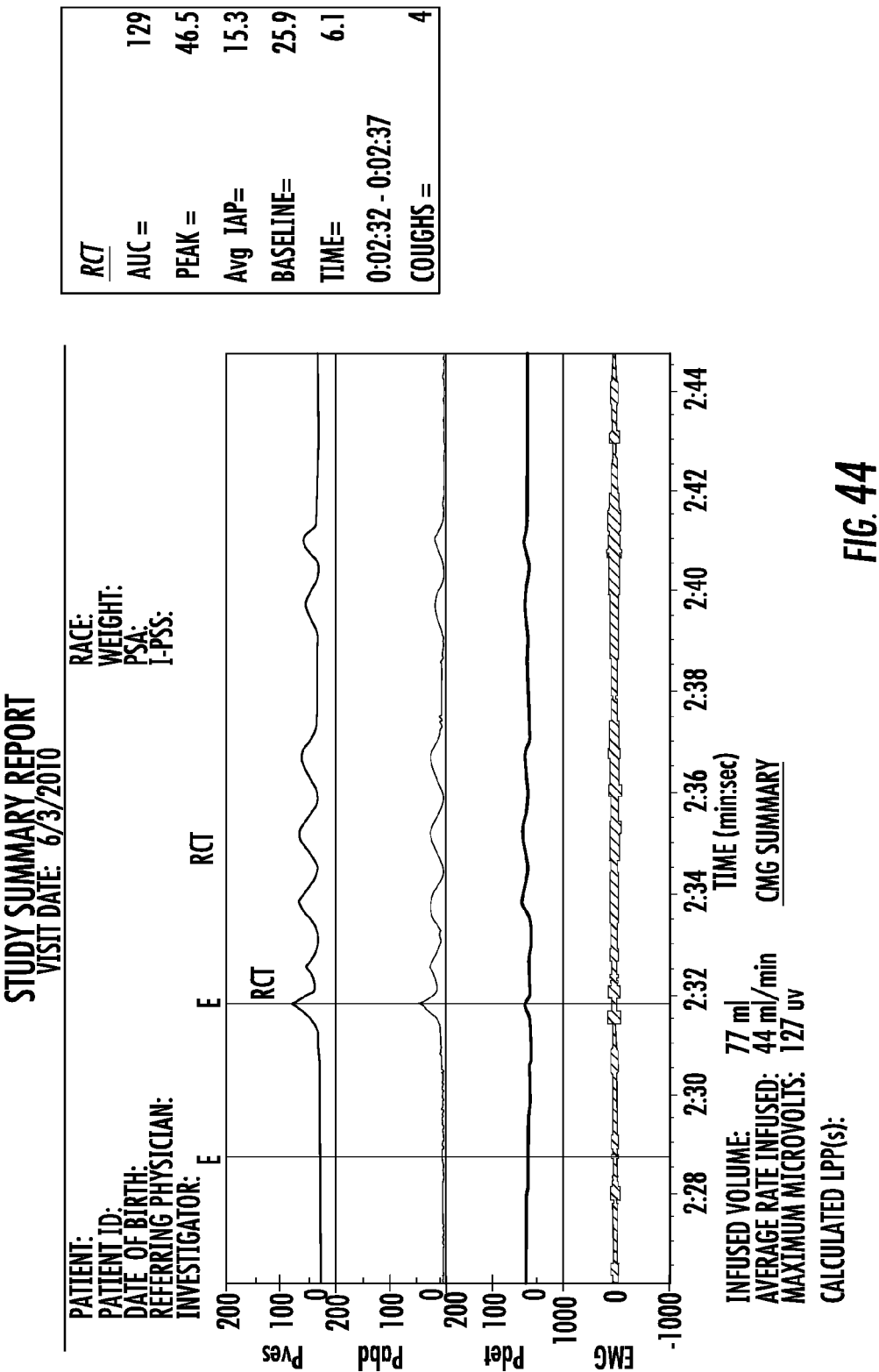

FIGS. 43 and 44 are graphs illustrating a subject that had a neuro decline over about a 1.5 year period. There is a marked decline in the iRCT measured variables and it is used to help determine medical management and demonstrate to the patient objective data to help in explaining the patient's physical condition and neurological status. Both tests are about the same for the costs and duration, but have a drastic decline in variables for airway protection (peak, average TAP and AUC). This patient had been fed by a stomach tube, Percutaneous Endoscopic Gastrostomy (PEG), which he chose in order to try to prolong respiratory health. The patient had been discharged home with a permanent stomach PEG and oral hygiene, but nothing significant by mouth and the patient had agreed. The patient had been diagnosed as having Parkinson's Disease, but it appeared to be Amyotrophic Lateral Sclerosis (ALS) and the patient was completely capacitated and had no other Parkinson's symptoms. Sinemet and Eldapril were not effective. This did not change the recommendations or description of the risk to the patient. The patient was to be followed up with pulmonary analysis with additional oxygen as needed for exertion only.

Figure 45:
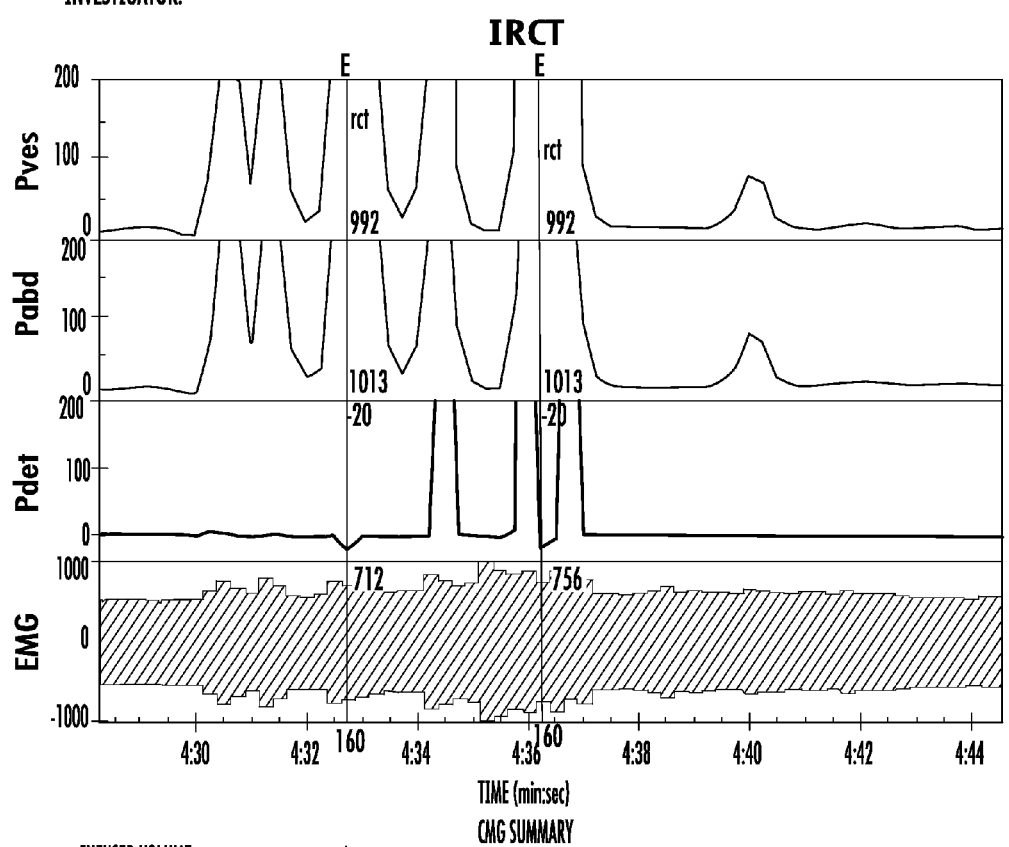
FIGS. 45-47 are graphs for the reflex cough test, CMG with EMG from the L5/S1 midline paraspinal muscles as a normal iRCT/LER test.
Figure 46:
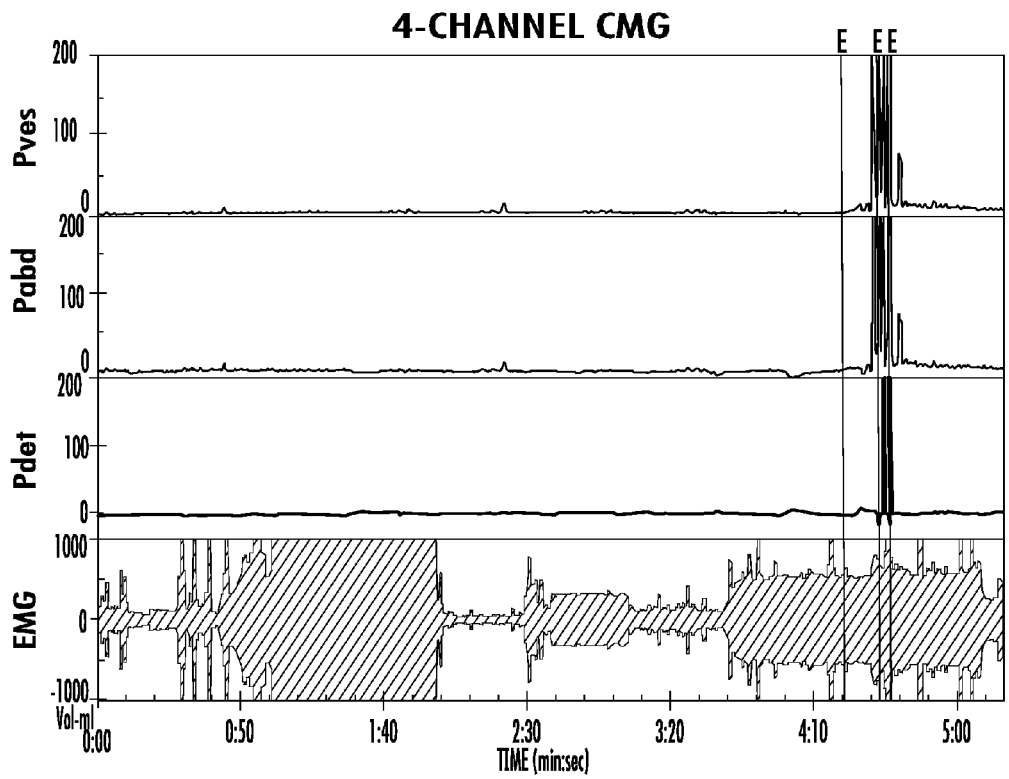
Figure 47:
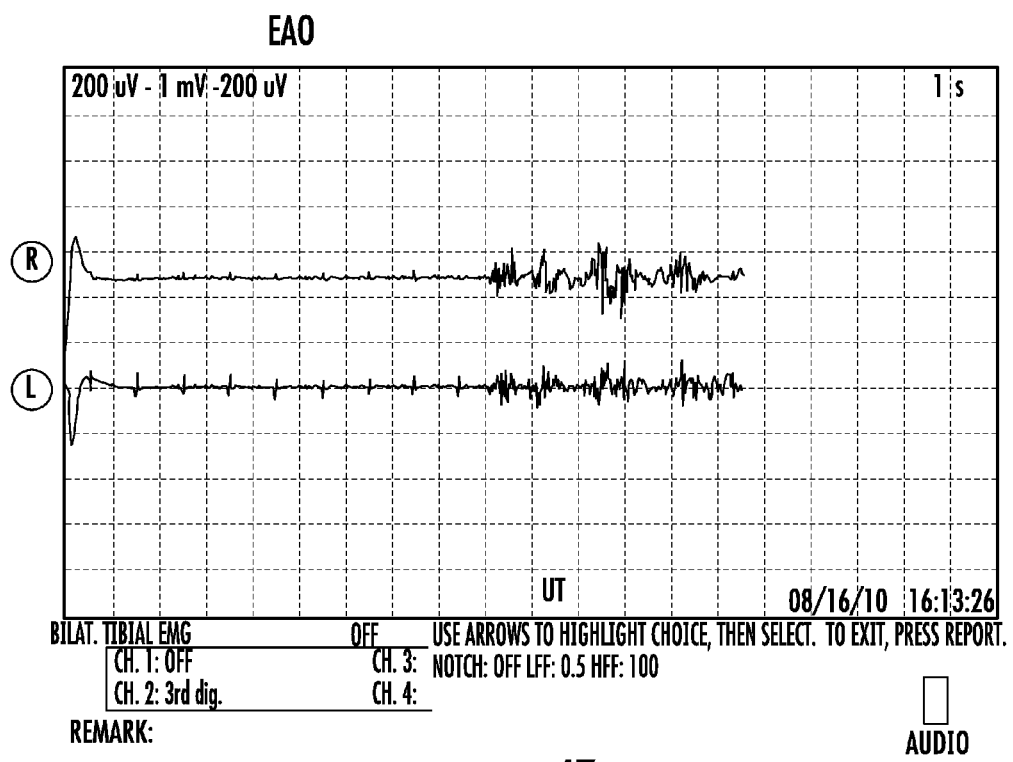

FIGS. 45-47 are graphs showing a CMG summary with the iRCT (FIG. 45) and the four-channel Cystometry (CMG) (FIG. 46) and the Electromyography (EMG) from the L5/S1 midline paraspinal muscles for a subject. The event lasts seven seconds. This is a normal iRCT/LER test. FIG. 47 shows the graph for dual external abdominal oblique (EAO) muscles. The graphs appear symmetrical and synchronous. The left side is apparent by EKG and this artifact could be reduced in later studies by filtering, but it is clear evidence of R (Right) versus L (Left) external abdominal oblique (EAO) muscle activation by LER. This subject is profoundly aphasic, non-agitated, has a PEG tube, Left MCA CVA (middle cerebral artery, cerebrovascular accident) with dense R hemiparesis and neglect. The subject is unable to perform voluntary cough or follow-up commands. There is mild increased R tone and brisk reflexes present. Bilateralism and decussating pathways of LER are at brainstem level in the subject without evidence of brainstem shock. The IAP are truncated, but the machine reads greater than 1,000 cm/H2O pressure. No adverse events were seen and the patient tolerated easily. It is apparent that the EAO EMG is not necessary and the IAP reflects function well. This can be compared easily to another patient as shown in FIG. 48 for an aphasic subject with the absent iRCT.

Figure 48:
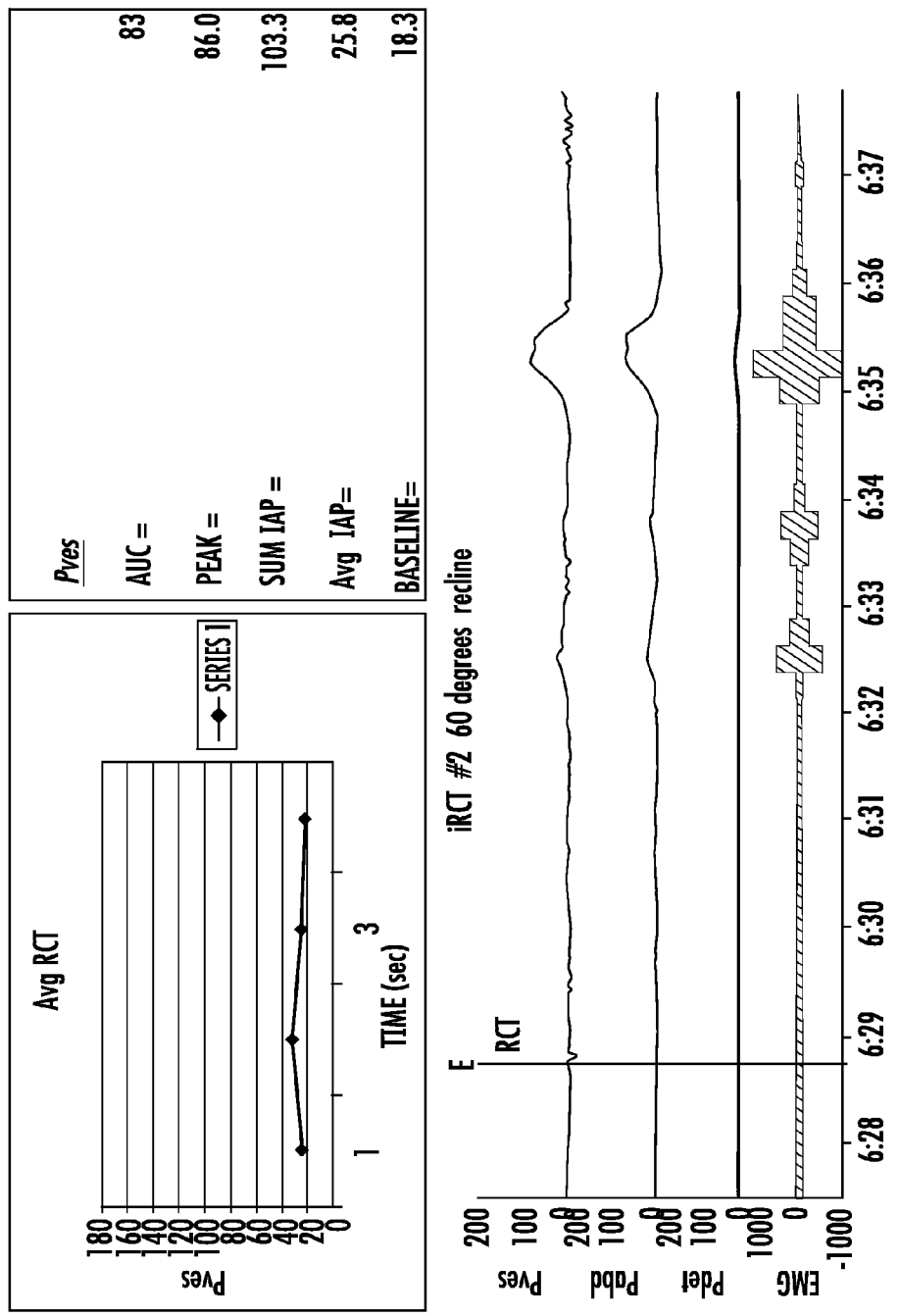
FIG. 48 is a graph showing abnormal test as a comparison to the normal test shown in FIGS. 44-46.

FIG. 48 is a graph showing an abnormal LER iRCT as compared to the normal LER iRCT as shown in the previous graphs of FIGS. 45-47. These demonstrate the differences between normal and abnormal with the measurement. It is evident there is a response present based on EMG from the L5/S1 and small corresponding pressure changes so even though the event is abnormal, it is still defined by the systematic approach as described. This shows that there is a decline or recovery by measurement and how this information is used can determine treatment and management choices.

There now follows details for NG/OG devices in FIGS. 51-53, which can be used to diagnose GERD, treat reflux, protect a patient's airway, and perform analysis as associated with the iRCT as explained below.

Aspiration pneumonia is a leading cause of morbidity and mortality in neurological compromised patients. Stroke associated pneumonia, occurring in 7-22% of patients, is a major complication and thought to be the most common cause of poor outcome and death in stroke patients. The risk for pneumonia is highest in the acute state of stroke and in patients with non-lacunar strokes in the middle cerebral artery (MCA) territory. Several risk factors contribute to the increased susceptibility of stroke patients for infections: aspiration due to drowsiness, impaired bulbar reflexes, dysphagia, hypostasis in bed-ridden patients, and a requirement for invasive medical procedures. Previous studies have found dysphagia is associated with respiratory infections, but those patients who are NPO (nothing by mouth) and tube fed have a higher risk of developing infections due to aspiration of bacteria-laden saliva or refluxed material than stroke patients who are fed orally.

"Nothing by mouth" tube-fed survivors were unlikely to have aspirated anything other than saliva/secretions or reflux, but they had significantly higher rates of respiratory infections than those survivors fed orally. Stringent oral care and measures to prevent reflux are potentially modifiable aspects of stroke management.

It is estimated that up to 38% of patients die one month within the onset of acute stroke. Pneumonia contributes to 34% of all stroke deaths and represents the third cause of mortality in the first month after stroke. After stroke or other neurologic events, the laryngeal cough reflex (LCR) may be weakened or absent. This increases the risk of aspiration of food, medications, fluids or secretions past the vocal cords, leading to the development of pneumonia. Overall mortality associated with large volume gastric aspiration is approximately 30%. It is greater than 50% in patients with shock, secondary infectious pneumonia or ARDS (adult respiratory distress syndrome).

There now follows details of a device that can be used for iRCT diagnosis, prevent reflux, and protect a patient's airway as an NG/OG (Nasogastric/Orogastric) device.

The device shown in FIGS. 51a-51e can be used with the system and method as described above to prevent reflux, protect a patient's airway, and analyze a patient using the iRCT. It is well known that Salem sumps are typically clear-and-blue tubes that are two tubes in one. Salem sumps overcome the disadvantages of the older single lumen nasogastric (NG) tubes where if suction was applied and the stomach drained, but the stomach was empty, the tube would suck up against the stomach wall or suck air out of the stomach and collapse the stomach. Thus, the second lumen as a "blue" tube is typically added such that when the stomach is empty, the second tube allows air to come back into the stomach and prevent the tube from sucking up against the stomach wall and allow venting such as for belching. This is the "sump" as the second lumen and sometimes referred to as the "pigtail" to allow venting.

Figure 49:
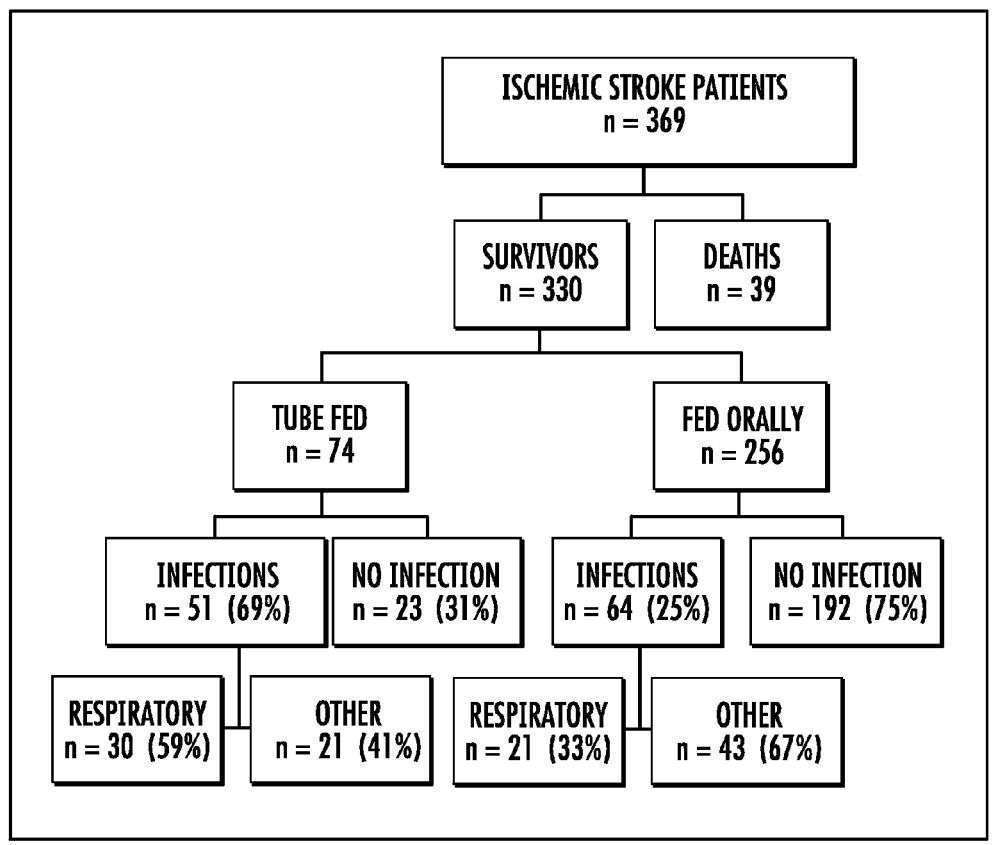
FIG. 49 is a flowchart showing a tube feeding status and subsequent infection rate.
Figure 50:
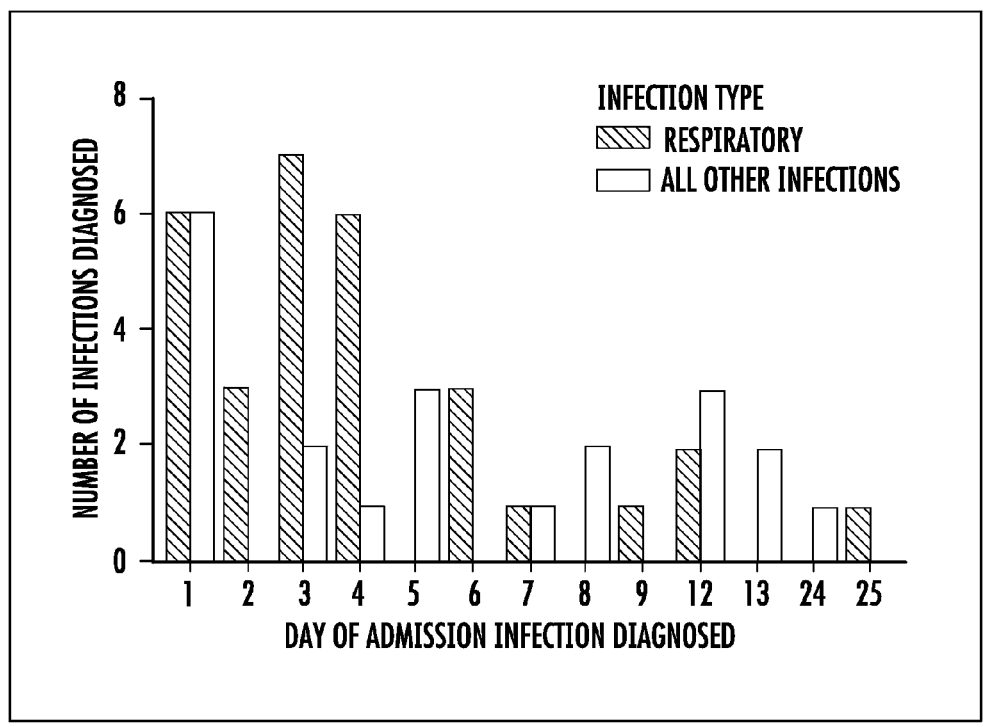
FIG. 50 is a bar chart showing time-to-infection data for survivors who were tube fed and developed infections after stroke.

FIG. 49 shows a flowchart of the various treatment possibilities for ischemic stroke patients. A few deaths occurred, but the survivors had to be either tube fed or fed orally. In this example, the flowchart shows an example of one study and the percentage of infections and no infections and the type of respiratory or other infections that occurred. Other studies would vary of course from those results. FIG. 50 shows time-to-infection data for survivors who are tube fed and develop infections after stroke. FIGS. 49 and 50 thus illustrate the importance of being able to attend to stroke patients.

FIGS. 51a-51e show the NG/OG device in accordance with non-limiting examples. As will be explained in detail below, this device includes a foam or air-filled esophageal cuff that is inflated using a separate lumen that is separate from the main lumen and any sump lumen. The device typically includes a pressure "bubble" at the end of the inflation lumen and could include a manometer connected for measuring pressure, for example, at the esophageal cuff and against the esophageal wall. Another lumen extending through the main body could be included with holes for suction just above the Lower Esophageal Sphincter (LES) to aid in suctioning reflux or emesis. This is advantageous for a surgery patient or acute neural or trauma patient. Details of such device are explained below.

It should be understood that stroke can cause Lower Esophageal Sphincter (LES) weakness. The urology studies discussed above address that determination. The LES is weakened by stroke and other factors, including the initiation of an involuntary cough such as through the iRCT test. The NG/OG device, in accordance with a non-limiting example and described in detail below, acts as an esophageal reflux protection device to protect the patient from the weakness of the Lower Esophageal Sphincter (LES). It is known that cough causes reflux, which causes more cough. This is a vicious cycle. This device allows blocking of emesis and prevents reflux associated with pneumonia and anesthesia or other functions affecting neural patients. The NG/OG device shown in FIGS. 51a-51e can be used when there is microscopic reflux or massive emesis, which both can cause pneumonia. In some instances, it may be possible to use a Foley catheter and a smaller catheter tube and the Foley catheter left in place and a smaller catheter pulled after cough is measured.

It should be understood that the esophagus is about 25 centimeters long. It is a muscular tube with a diameter of about 2 centimeters average. It tracks the vertebral column curve and descends through the neck and posterior mediastinum and passes through the esophageal hiatus in the right crus of the diaphragm to the left of the median plane at the level of the T10 vertebrae.

The esophagus enters the stomach at the cardial orifice to the left of the midline at the level of the 7th left costal cartilage and T11 vertebra. The abdominal part of the esophagus extends from the esophageal hiatusis in the right crus of the diaphragm to the cardial (cardiac) orifice of the stomach. This area is only about 1.25 cm long.

Food passes through the esophagus rapidly because of the peristaltic action and is typically not dependent on gravity. The esophagus is attached to the margins of the esophageal hiatus in the diaphragm by the phrenicoesophageal ligament, an extension of the inferior diaphragmatic fascia. This ligament permits independent movement of the diaphragm and esophagus during respiration and swallowing. The esophagogastric junction lies to the left of the T11 vertebra on the horizontal plane that passes through the tip of the xiphoid process. Immediately superior to the esophagogastric junction, the diaphragmatic musculature forming the esophageal hiatus functions as a physiological inferior (lower) esophageal sphincter (LES) that contracts and relaxes. The sphincter mechanism for the LES is typically efficient in preventing reflux of gastric contents into the esophagus based on radiological studies. The lumen of the esophagus is normally collapsed superior to this level to prevent food or stomach juices from regurgitating into the esophagus when an individual is not eating.

Barium fluoroscopic studies of the esophagus normally show three constrictions of the esophageal lumen due to impressions from adjacent structures. These are possible locations for placing a device reflux analysis and GERD treatment.

A first constriction is the cervical constriction (upper esophageal sphincter). The superior aspect of the esophagus is the pharyngoesophageal junction, and is approximately 15 cm from the incisor teeth. The cricopharyngeus muscle creates this cervical constriction, which is located at approximately the level of the sixth cervical vertebra.

A second constriction is the thoracic (broncho-aortic) constriction. The arch of the aorta and the left main bronchus cross the esophagus and create esophageal constrictions as seen on anteroposterior and lateral views, respectively. The constriction caused by the arch of the aorta is 22.5 cm from the incisor teeth and the constriction formed by the left main bronchus is 27.5 cm from the incisor teeth.

A third constriction is the diaphragmatic constriction. The esophageal hiatus of the diaphragm is approximately 40 cm from the incisor teeth and forms the diaphragmatic constriction. This is at the level of the lower esophageal sphincter.

The presence of these constrictions is important when placing the device as described with the esophageal cuff, which would help prevent the reflux of gastric contents into the upper esophagus and pharynx. The placement of the device in one example is suggested inferior to the broncho-aortic constriction (27.5 cm from the incisor teeth), but superior to the diaphragmatic constriction at 40 cm from the incisor teeth. The device typically should not be placed in regions of the esophagus with pathological involvement of the esophagus.

Figure 51A:
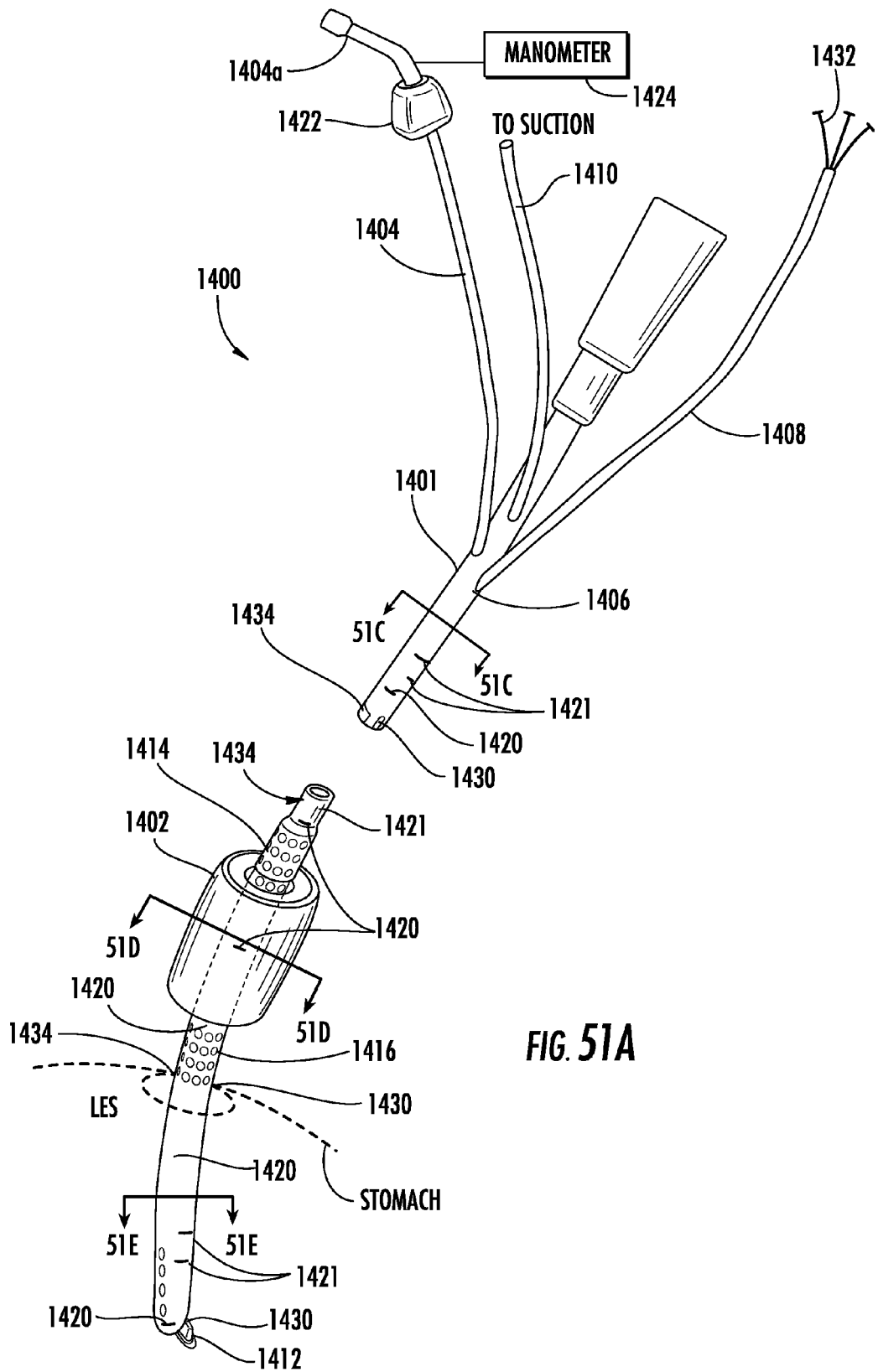
FIGS. 51a through 51e are figures showing an oral-esophageal and gastric catheter (NG/OG device) with an esophageal device to reduce or diminish gastric reflux and/or emesis in surgical, neurological and/or trauma patients in accordance with a non-limiting example.
Figure 51B:
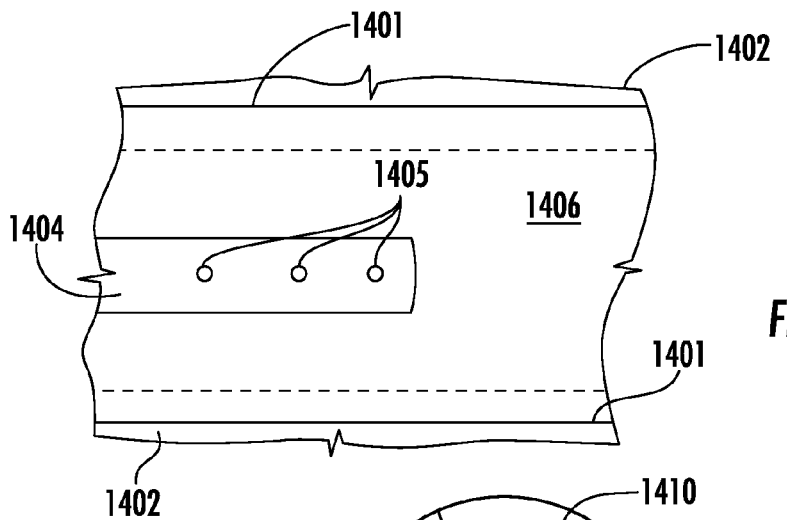
Figure 51C:
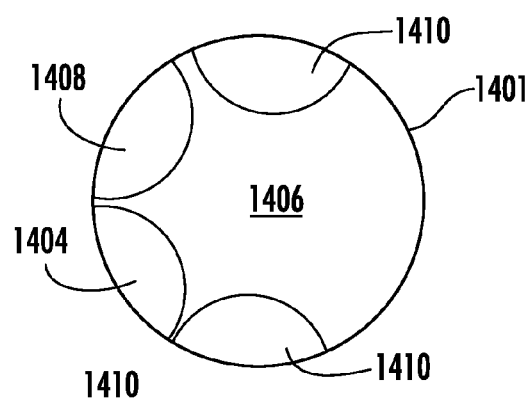
Figure 51D:
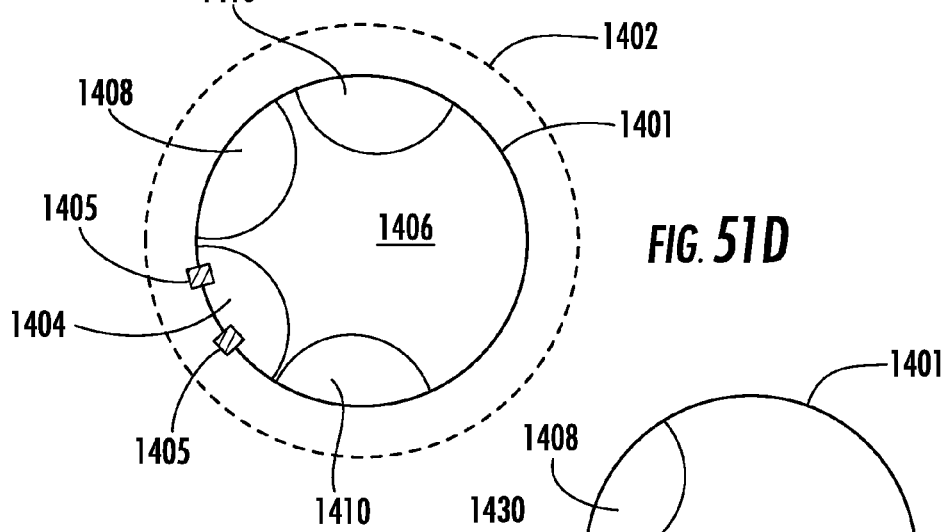

FIGS. 51a-51e show the device in plan and sectional views and indicated generally at 1400, and includes a main device body 1401 and a foam or air-filled esophageal cuff 1402 with a separate inflation lumen 1404 for inflation and deflation as shown in FIGS. 51b-51d. FIG. 51b shows the cuff 1402 in deflated position and FIG. 51d shows the cuff inflated. Air channels 1405 connect the inflation lumen and the cuff as shown in FIGS. 51*b* and 51*d*. The section view in FIG. 51*b* shows the termination of the inflation lumen.

Figure 51E:
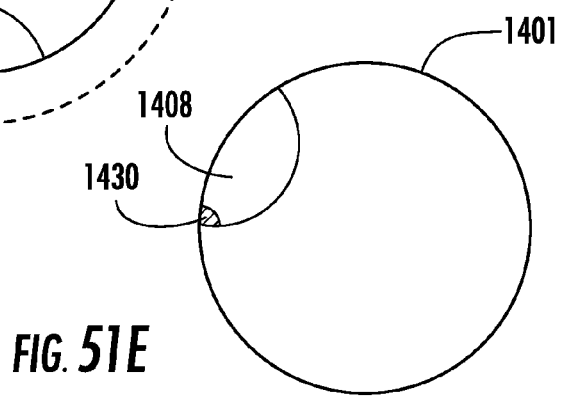

The tip of the device is shown positioned in the stomach, which is shown schematically in FIG. 51*a*. FIG. 51*c* is a cross-section taken along line 51*c*-51*c* of FIG. 51*a*. FIG. 51*d* is a cross-section taken along line 51*d*-51*d* of FIG. 51*a*. FIG. 51*e* is a cross-section taken along line 51*e*-51*e* of FIG. 51*a*. In these cross-sections, the various lumens are shown, including the main lumen 1406, the sump lumen 1408, the inflation lumen used for inflating the cuff, and any suction lumens 1410 that are used for suction above the LES. The sump lumen 1408 is connected to a sump port 1412 (FIG. 51*a*) at the end of the device 1400. Drainage holes 1414 positioned in this example above the cuff 1402 allow secretions to pass into the device. These drainage holes could be formed as suction holes such as in the example device described relative to FIG. 52 and connected to any suction lumens. Suction holes 1416 are positioned below the cuff 1402 and connect to the suction lumens 1410 to permit emesis and reflux to be suctioned. The drainage holes could also connect to the suction lumen 1410 as noted before. In a non-limiting example, the drainage holes and suction holes include one-way valves to allow emesis to enter, but not return.

This device typically forms as a nasogastric or orogastric tube with a Salem sump port 1412 and an additional port 1404*a* for air entry and exit to and from the esophageal cuff, allowing a high volume and low pressure cuff 1402 as illustrated and supplied by the inflation lumen 1404. The device can come in variable sizes and lengths depending on patient needs and requirements and typically a standard size for use depending on patients. The device can be used for gastric enteral feedings or gastric decompression resulting from the use of the Salem sump port 1412. The device typically includes radio-opaque markings 1420 throughout the length of the tube as illustrated for measurement and placement. Measured markings 1421 as indicia can be positioned in one example along the length of the tube together with a color changing material or pit sensitive material and at the bulb/cuff for measuring emesis, etc.

The cuff 1402 that is shown in its inflated position in FIG. 51*a* is high volume and low pressure and can be inflated with air. It could be foam filled or a combination of both air and foam. Inflation and deflation is through the leur lock port 1404*a* that includes the pressure inflation balloon 1422 adjacent thereto. The inflation balloon 1422 allows for a tactile cuff and a gross pressure check such as through a manometer 1424 attached thereto. The leur lock port 1404*a* attaches in one example to a manometer for actual cuff pressure measurement. The cuff 1402 easily collapses for emergency removal or self-extubation without causing damage to surrounding structures of the esophagus, hypopharynx, pharynx, and oral cavity. The cuff is kept inflated below the capillary pressure of the esophageal wall to prevent ischemia that is typically about 7-8 centimeters (cm) water. As indicated before, there are radio-opaque markings 1420 to aid in device placement confirmation. The cuff can be radio-opaque to aid its placement. The upper portion of the esophageal cuff is typically mildly concave to promote secretion to flow towards openings as drainage holes 1414 (or suction holes if formed as such) in the device in this example. An upward force, such as emesis or vomit on the lower portion of the cuff, expands the cuff outwards towards the esophageal wall to control gastric contents from entering the hypopharynx. The inflation/deflation port 1404*a* can be a different color than the openings for the sump lumen, the suction lumen and the main lumen. The inflation/deflation port 1404*a* in one example is fitted with the standard leur lock cap and the inflation/deflation port can be labelled with the term "esophageal cuff" to aid practitioners or identifying.

The NG/OG device is typically inserted through the nasal cavity or through the oral cavity and enters into the stomach. Measurements can be made from the lips or nares to the TMJ (temporomandibular joint) and to about four-finger breadths to sub-xyphoid. When the esophageal cuff 1402 is deflated, a water-soluble lubricant can be applied to the end of the device to aid insertion. This NG/OG device is inserted in a manner similar to an OGT (orogastric tube) or NGT (nasal gastric tube) (NG/OG tube) with the clinician or nurse using the placement radio-opaque markings 1420 to position the device over the lungs and stomach. Once it is in position, it is possible to use auscultate placement by listening to sounds and using an air bolus into the tube and attempt to aspirate gastric contents from the tube. The tube is secured and its placement confirmed by x-ray (using the radio-opaque markings 1420 for help) with the preferred location inferior to the broncho-aortic constriction while superior to the diaphragmatic constriction. The cuff 1402 is inflated through the inflation lumen 1404 and the cuff pressure typically measured with the manometer 1424. The main lumen 1406 as part of the device body 1401 will have low continuous or intermittent suction and may also be used to administer external feedings.

The device 1400 is advantageous for use such as with the neurologically impaired who are at risk for aspiration of gastric contents, including those suffering from a cerebrovascular accident that could be ischemic, thrombotic or hemorrhagic. The device can be advantageously used for non-traumatic brain injury including incephalopathy or intracranial tumor/mass. The device can also be advantageously used when there is traumatic brain injury and general anesthesia, including intra-operative or post-operative, for example, when the patient is neurologically impaired and may not be able to protect their airways. The device is also advantageously used with neurological disorders including Parkinson's Disease, amyotrophic lateral sclerosis and bulbar impairment, myasthenia gravis, and multiple sclerosis. The device is advantageously used with compromised consciousness such as through alcohol intoxication, drug overdose and psychiatric disorders. Indications for use also include gastric decompression because of the use of the sump port and gastric enteral feedings. There are some contraindications for use of the device, including esophageal disruption, esophageal stricture, esophagectomy, esophageal varices, connective tissue disease involving the integrity of the esophagus and cancer of the esophagus.

In accordance with a non-limiting example, the involuntary Reflex Cough Test (iRCT) is used to evaluate the impairment and/or recovery of airway protection. Cuff pressure can also be measured by the manometer 1424. An advantageous pressure for the cuff 1402 is below the esophageal wall capillary pressure. The use of the involuntary reflex cough test is advantageous for people who are neurologically impaired to check to see if they can protect their airway. In this particular device example, pressure sensing is used in conjunction with the device. EMG determination can also be used, as well as pH sensing. Any transceiver inputs for pressure, pH or EMG could input directly into the handheld device. For example, the device could carry pressure sensors as pressure transducers 1430 at various locations on the device to measure pressure when the device is inserted within the esophagus. The transducers 1430 could have transducer leads 1432 that extend through the sump lumen 1408 or be embedded in a wall of the main tube or one of the other lumens. One pressure sensor or transducer 1430 could be in the stomach (such as at the sump lumen), another at the LES, another at mid-esophageal and/or another at the superior esophageal location. It is possible to use an air charged catheter as a pressure sensor with a separate lumen for determining pressure in the stomach, which can be used to determine intra-abdominal pressure. An air charged catheter would require some calibration. Other sensors as non-limiting examples could use fiber optic or other circuit means. The intra-abdominal pressure can be measured but also intra-thoracic pressure. Reflux can be measured by having pH sensors 1434 as inputs along the side with leads also extending through the sump lumen in this example. The handheld device can connect by wired connection or wireless connection to the various pressure, pH and EMG sensors, probes, pads, transducers, etc. It should also be understood that the catheter can be coated with a color changing material, such as for indicating the extent of acid reflux or emesis.

FIG. 51b shows the main device body in an area around the cuff 1402 with the cuff in a deflated position. FIG. 51c shows the different lumens that extend through the device to the cuff area which is shown at FIG. 51d. The lower portion of the device is shown in FIG. 51e showing the main lumen and the sump lumen.

FIGS. 52a-52f disclose an NG/OG device 1400 similar to that shown in FIGS. 51a-51e with similar components that are common between both devices having common reference numerals. In this particular example, however, the device includes a nebulizer lumen 1450 that is extralumenal to the main device body 1401 and provides a nebulizer function using a separate nebulizer port 1452 from the main lumen. This nebulizer port 1452 connects to an oxygen or air source for delivering medication such as for the involuntary reflex cough test at the esopheryngeal area for inhalation into the pulmonary tree or medicine for treating a patient. As illustrated, the nebulizer lumen 1450 terminates at a nebulizer structure or nebulizer/medication delivery mechanism having a built-in venturi 1454 to allow delivery of medication for the iRCT around a portion or all the main device body 1401 forming the tube.

Figure 52A:
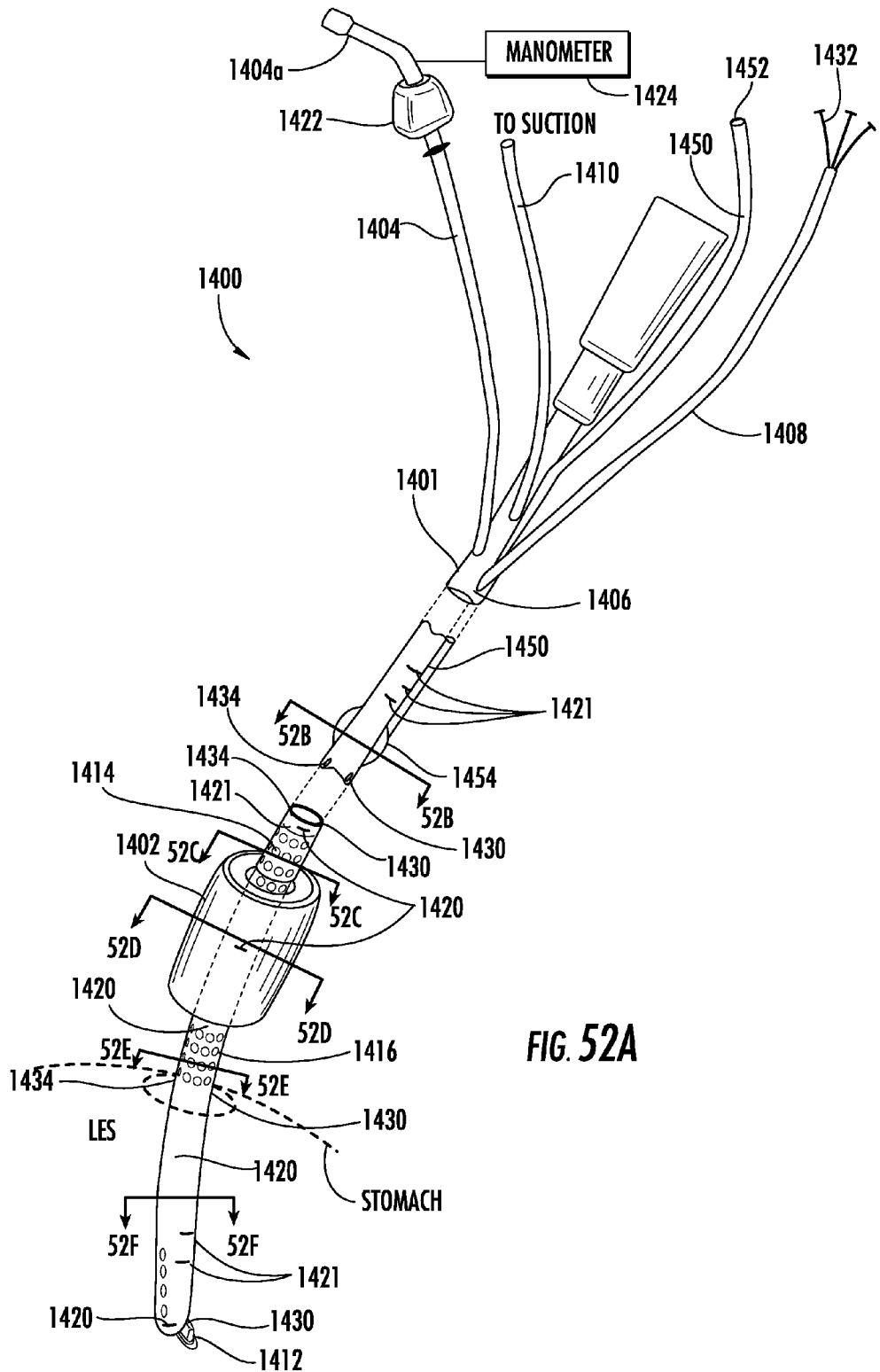
FIGS. 52a through 52g are figures showing another embodiment of the oral-esophageal gastric device similar to that shown in FIGS. 51a-51c but having a nebulizer function, pH sensing and pressure sensing.
Figure 52B:
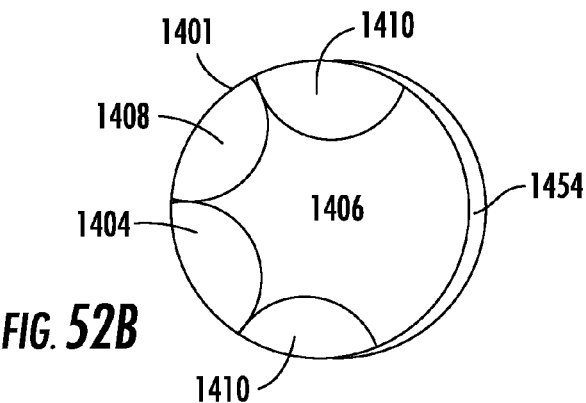
Figure 52C:
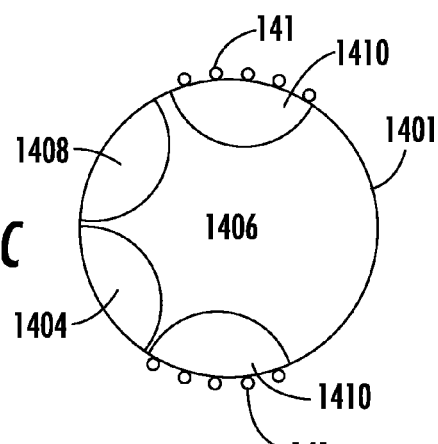

FIG. 52b shows a cross-section taken along line 52b-52b and showing the venturi of the nebulizer and the main lumen 1406, deflation/inflation lumen 1404, suction lumen 1410, and sump lumen 1408 that are similar as with the embodiment shown in FIGS. 51a-51e. The two suction lumens 1410 could merge near the proximal portion of the main body or be separate and provide either common suction at the same time above and below the cuff or individually controlled suction. The suction holes or ports as noted before include one-way valves to allow fluid into the suction lumen 1410, but not out. The valves could be formed as cut flaps that extend inward, but not outward to allow ingress, but not egress. This is advantageous such as when emesis extends upward around the tube from the stomach and can pass into the tube to be suctioned, but not passed back out. Also, secretions, if they get past the cuff, will be suctioned by the suction ports that are located above the cuff as illustrated.

The pressure transducers 1430 are located at various points such as at the distal tip at the sump to measure intra-abdominal pressure. A pressure transducer 1430 can be located below the cuff 1430 and above the cuff 1402 with leads extending through the sump lumen 1408 and connected to the handheld device. A pressure transducer 1430 in one example is located at the sump lumen as shown in FIG. 52f. As noted before, it is also possible to include pH sensors 1434 on the device that include leads extending through the sump lumen 1408, allowing pH to be measured to detect when emesis is rising from the stomach. The pH sensors 1434 could be located at different locations such as below the cuff and above the cuff and even farther up along the main device body 1401. The coating on the device could indicate pH.

This NG/OG device as illustrated in FIGS. 52a-52f is a multi-purpose NG/OG device that can be used in a variety of patients who are at risk for aspiration of gastric contents, elevated intra-abdominal and/or intra-esophageal pressures, and/or abnormal airway protection. The device is not limited to the illustrated embodiments, but can be configured with all or any variation in combination of different components to fit the needs of the patient.

The main lumen 1406 extends the entire length of the device and as noted before, the device has radio-opaque markings 1420 along its length, and also measurement markings 1421 as indicia in one example along its length. The entire cuff can be radio-opaque to enhance placement. This device 1400 permits gastric decompression and can be used with a low continuous or a low intermittent suction to remove gastric contents, including liquids and gaseous materials. The device allows enteral feeding that can be administered into the gastric cavity for nutritional support. Any enteral medication administration allows medications to be administered into the gastric cavity.

The sump port 1412 as noted before is intra-lumenal with its own sump lumen 1408 and is integrated the entire length of the device. The sump port opens at the end of the device and when located within the stomach, as when the device is in operation, prevents adherence of the device to the gastric wall and also vents gastric gaseous build-up.

The nebulizer venturi 1454 permits inhalation medication administration. The venturi 1454 is extralumenal and connects to a high-flow oxygen or air source in a non-limiting example. Nebulized medications are delivered through the venturi 1454, typically at the level of the larynx and hypopharynx. The involuntary reflex cough test can therefore be administered efficiently using the device as described.

The cuff or inflation lumen 1404 provides inflation for the esophageal cuff, which as an inflatable cuff is located at the mid-esophagus section and can be inflated and deflated via the leur lock tip balloon 1422 that provides a "feel" for the practitioner to aid in pressure measurements. The pressure of the cuff 1402 can be checked using a manometer 1424, which attaches to the leur lock tip. Gross pressure can be tested manually using the indicator balloon. The esophageal cuff 1402 provides a barrier for any refluxed gastric material from entering the upper esophagus and airway. An unplanned dislodgement of the esophageal cuff does not cause injury because of the particular cuff structure as a flexible material and its configuration to collapse when necessary. Also, the amount of pressure is not excessive enough to harm the esophageal wall in most instances.

The esophageal suction ports 1416, which in this embodiment are both above and below the cuff, permits suction to occur and uses one-way port holes that are located above and below the esophageal cuff such that emesis, reflux and other material can be sucked into the suction lumen 1410 but not pass out. The suction ports 1416 open with the administration of low pressure and intermittent suction. Low suction can be applied to remove the refluxed gastric material in the lower esophagus below the esophageal cuff. The low suction can also be applied to remove material such as, but not limited to, oral or nasal secretions, medications and/or tube feeding material that is collected in the esophagus above the esophageal cuff. For purposes of identification to the nurse or other practitioner, it can be labelled as "Intra-Esophageal Access: Do Not Instill."

The sump lumen typically will carry transducer leads that extend in the lumen and out past the discharge end of the sump lumen 1408, but the leads could be embedded in the wall of the device. The handheld device or other processing device can connect wirelessly or by wired connection to the transducer leads and monitor pressure within the upper esophagus, the lower esophagus, and within the gastric cavity. Sensors or probes for pH 1434 can be included as noted before and have leads extending through the sump lumen 1408 and out past the proximal end. The leads extending out of the sump lumen for those sensors, transducers or probes can connect to a transceiver for wireless signal transmission to the handheld unit (or wired connection) in one embodiment. Any pressure transducer can send its signal not only into the handheld device, but also into a monitoring system that includes alarms to notify the staff of any increased pressures above or below the esophageal cuff or within the gastric cavity. Sensors for pH can be configured to sound an alarm such as when emesis occurs.

Typically, the nebulizer venturi 1454 will be positioned at the level of the larynx between the nasal pharyngeal area/oral pharyngeal area and allow medication to be administered. The device can be used to measure both intra-abdominal hypertension and reflux. The dimensions of this device are typically not larger than a regular NG/OG tube and not larger than 18 to about 20 French. The sump lumen is much smaller as compared to the main tube, but in this example, large enough to accommodate various leads, which could extend through other lumens. The sump lumen, however, typically remains more clean.

The NG/OG antireflux/emesis device as described with reference to the preceding description includes suction both above and below the Lower Esophagael Sphincter (LES) as explained above. With placement of the "umbrella" or esophageal cuff close to a predetermined level below the aortic esophageal indentation, the inflation with saline or air opens a predetermined cuff shape similar to an hourglass cut in half in one non-limiting example. The bowl shape as identified above as an example collects swallowed secretions and allows passage through both directions for gases. The umbrella would open a limited amount under emesis pressure, and a sensor could flag or alert a monitoring system, triggered by the umbrella or cuff opening while at the same time, automatic suctioning could occur above the LES from the port. The device is also a fully functioning feeding tube for food, liquids or medicine to the stomach and acts as a separate reverse channel, to allow suctioning below the LES in the stomach, and the possibility for constant low-pressure suctioning for reflux above the LES. In a preferred example, the device collapses with pulling even if it is not deflated and pulled by a patient for safety. As noted before, xrays can be used to aid placement of the device in the esophagus. This device can be engineered as necessary for any severe neuro functions and risks for LES weakness or increased LER activity because of dysphagia or reflux, and protect general anesthesia patients after extubation. The device is useful for iRCT testing and protects the patient from neutral created anti-acid medicine stomach content reflux the might get past the ASIC receptors or RAR's (retinoic acid receptors).

The device as described has many different advantageous uses. The top portion of the device includes different ports and non-ports, all operating together as an NG/OG tube for oral or nasal uses. This device also can test reflex cough and deliver micro-nebulized medicines, such as disclosed in commonly assigned U.S. patent application Ser. No. 11/608,316 filed Dec. 8, 2006; Ser. No. 11/550,125 filed Oct. 17, 2006; Ser. No. 12/643,251 filed Dec. 21, 2009; and Ser. No. 12/643, 134 filed Dec. 21, 2009, the disclosures which are hereby incorporated by reference in their entirety.

The nebulizer lumen 1450 in one example typically extends about half the length of the tube, and in an example is flush with the side of the tube. In FIG. 52*a*, the device is shown broken in sections for clarity since it is not necessary to show the entire length of the device when only major components are to be illustrated. Nebulized medication enters through one of the ports at the top section of the nebulizer lumen, which terminates at the venturi as illustrated. The medication does not pass into the main tube, but around it, for example, at the level of the larynx in this example. For example, the venturi could be located between the nasal pharyngeal and oral pharyngeal and/or distal. Medication can be administered into that portion of the airway.

The suction lumen includes the one-way valves at the suction ports 1416. Suction can be activated as when emesis occurs and it is brought into the lumen. The main lumen 1406 forming the main device body 1401 provides for food and fluid to pass into the stomach while the other lumens as illustrated provide specific functions and are typically integrated with the main device body.

The esophageal cuff 1402 is located on the outside of the main tube and can be inflated and deflated as noted before. The balloon 1422 is located such that the practitioner can manually feel the pressure of the balloon to exert pressure on the cuff 1402. Manually manipulating the balloon can place pressure on the esophagus via the cuff, and thus, the practitioner can use the feel of the balloon and cuff in this non-limiting example such that the cuff will not cause tissue ischemic.

Suction can occur above and below the esophageal sphincter and suction can occur above and also below the cuff. There are, in some of these examples, one-way valves above and below the cuff that allow emesis or other material to go from outside the device to inside the tube. These one-way valves can be passive and fluid can enter through the one-way valves and be pushed down into the stomach or suctioned up in another example. The device is designed such that emesis cannot come up around the tube. This is important when the patient is unconscious and tube fed, allowing protection of the airway for the patient and protecting the patient from any lower esophageal reflux such as with involuntary events. If a patient inhales, the lower esophageal sphincter closes. If an involuntary event, such as an involuntary reflex cough occurs, and a patient has not inhaled, reflux can occur. This has been shown with a damaged or malfunctioning urethral sphincter or damaged or malfunctioning lower esophageal sphincter.

Guardian reflexes are typically parasympathetic driven. The parasympathetics are cranial and sacral and the sympathetics are cervical, thoracic and lumbar. When a patient inhales, the diaphragm drops and activates the dorsal and causes the lower esophageal sphincter (LES) above the stomach to close. If an event occurs and the internal sphincter does not close, the external sphincter is left alone. This is when patients leaked and why they often have stress incontinence. The involuntary cough happens in about 17 milliseconds and they are not able to inhale. There is no parasympathetic to close the inner sphincter, evident in graphs discussed before. This can be explained because the internal sphincter closes with inhalation. Between every cough, there is an inhalation and the diaphragm drops and the dorsal motor nucleus and para-abductal communicate with the parasympathetics from the cranial and sacral distribution. The device as explained is advantageous because when reflux occurs, and if there is an involuntary cough and reflux, the airway is protected, especially if the patient is unconscious.

When the patient aspirates, a practitioner typically may try to neutralize the stomach contents. The airway will not be able to protect itself because of the neutral pH, and the reflex cough will not activate because the acid receptors are not activated (because of the neutralized stomach). This protective device, in accordance with a non-limiting example, is advantageous to protect the patient.

Normally if the contents are acidic, even if a patient is unconscious and the cough is operative, then the patient would cough material out and this material would not move into the lungs. If the stomach has been neutralized, however, the contents of the stomach may go past the acid receptors and vocal cords and there could be an aspiration syndrome.

In the past, NG/OG tubes were not used with a patient that could not protect their airway. This protective NG/OG device as described, however, in accordance with a non-limiting example, is safely used with a patient that cannot protect their airway and especially useful when administering the iRCT in case reflex occurs. The device can be left in a patient for protection.

The sump port 1412 is integrated into the side of the main tube forming the main device body and exits the base of the tube into the stomach. The sump port vents and prevents adherence of the tube to the wall of the stomach if suctioning occurs, preventing complete vacuum and even collapse of the stomach. A pressure transducer is placed at the sump port (FIG. 52f) for pressure measurements. The various sensors, transducers and probes typically may have leads that extend through the sump lumen and extend outward to plug into the handheld device. The pressure of the stomach can be checked to give a measurement for intra-abdominal pressure and aid in determining intra-abdominal compartment syndrome resulting from excess pressure. This could be a resting pressure. It is preferred, of course, in these scenarios, that pressure not extend above 12 centimeters of water, for example, indicative of intra-abdominal hypertension. Thus, the device as described can be used not only to measure intra-abdominal hypertension syndrome, but also to measure reflex cough. Typically, the reflex cough is activated from the nebulizer venturi 1454 when the various leads 1432 are plugged into the handheld device either by wired or wireless connection. This is as effective in some instances as measuring intra-abdominal pressure from the bladder, but there are some evaluations that occur to reflect that the pressure is sometimes higher from the stomach than from the bladder, which could be a reflection of device position.

Typically, voluntary cough is higher from the stomach than from the bladder. During this process, there could be higher reference numbers for normal between the bladder and the stomach. If there is a rise in normal pressures, then there is possible intra-abdominal hypertension. Typically, the bladder is 12 centimeters of water as a cut-off and the stomach could possibly be 20 centimeters of water, but this value is to be determined with greater testing.

This device prevents reflux from hurting a patient. The pressure transducers 1430 located at the stomach below the cuff and at a point above the cuff are advantageous. If there is pressure build-up below the cuff, it is because the patient typically has vomited and there is now fluid rising and there is possibly esophageal stretch that is placing pressure on the esophagus. It is possible to have a continuous read-out at the handheld unit of the various pressures along the esophagus and in the stomach. It is possible to place alarms on the device, which will activate if there is abnormal high or low pressure. For example, an abnormal high pressure could trigger an alarm and a nurse could assess the patient to see if the patient needs to be suctioned, and whether suction needs to occur above or below the cuff. Also, the nurse could determine if there are intra-abdominal high pressures. It should be understood that the main lumen can be used to feed and the different fluid ports, transducers, sensors and other components as described before are positioned around the main lumen based on the necessary physiology and function required for the device.

The esophageal cuff 1402 is an umbrella-type device such that pressure opens the cuff and blocks emesis. This could be dangerous to the esophagus if proper designs are not used for the cuff. The cuff, i.e., "umbrella," is designed to readily collapse. If the cuff opens because of emesis or reflux, the opening could trigger a transducer operative with the cuff and activate an alarm. A pressure transducer could be located at that cuff location. If pressure occurs at the cuff by opening the cuff, it will set the alarm off. The cuff in one example could be designed as a static blocking mechanism, and thus, be a static cuff, and in other instances a dynamic cuff. The design is important to ensure that the cuff is not rigid such that it would rupture the esophagus.

Figure 52D:
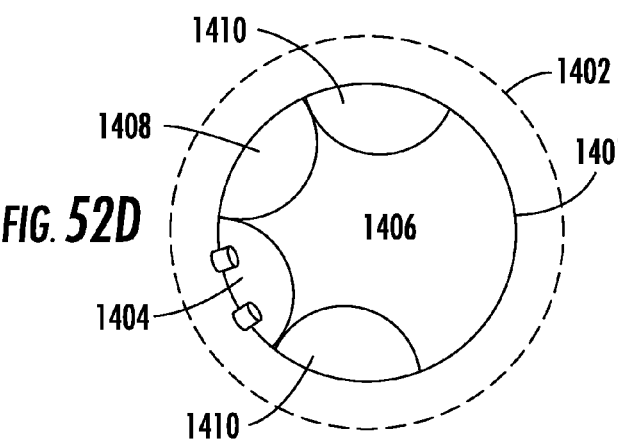
Figure 52F:
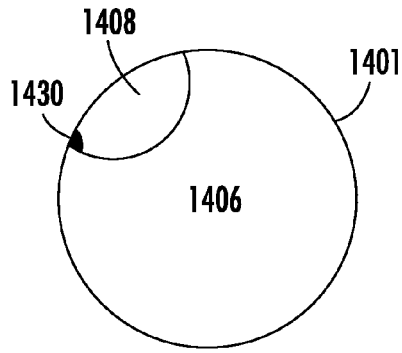
Figure 52E:
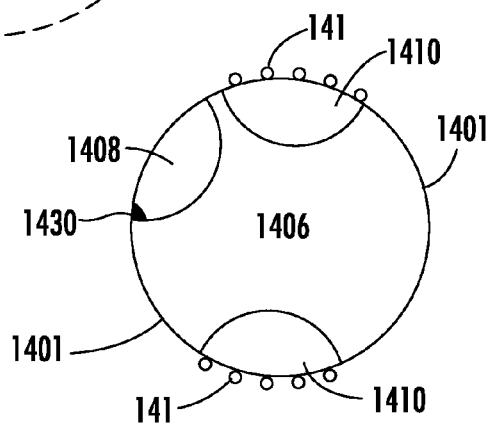
Figure 52G:
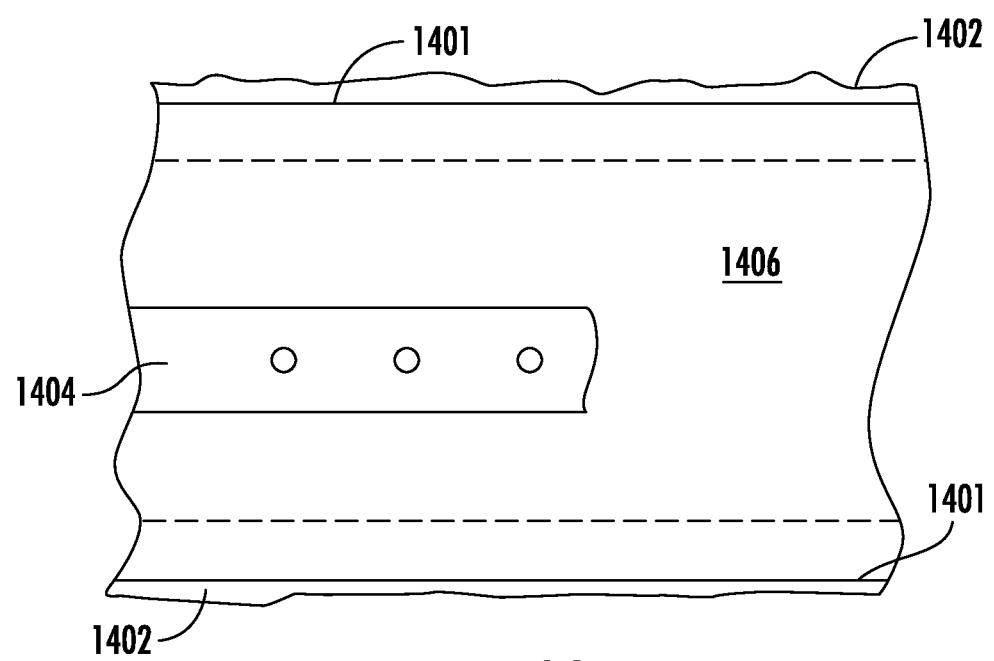

The cross-section views in FIGS. 52a and 52e show suction ports above and below the cuff (FIG. 52d). Any deflate/inflate port for the cuff could be just above the cuff with a pressure transducer above and below the cuff in a non-limiting example.

As is understood, the esophagus is a low-pressure system, and the cuff will typically operate as a low-pressure system. Low intermittent pressure is about 80 millimeters of mercury, and low continuous pressure is below about 80 millimeters of mercury. The esophagus is much smaller and the suction will typically be reduced to ensure that there is no excess pressure against the walls of the esophagus to cause damage. The pressure transducers, if strategically placed depending on the type of patient, can aid this determination. Air charged catheter technology can be used for pressure measurement where changes in physiological pressure are transmitted through a micro-volume of trapped air.

Figure 53A:
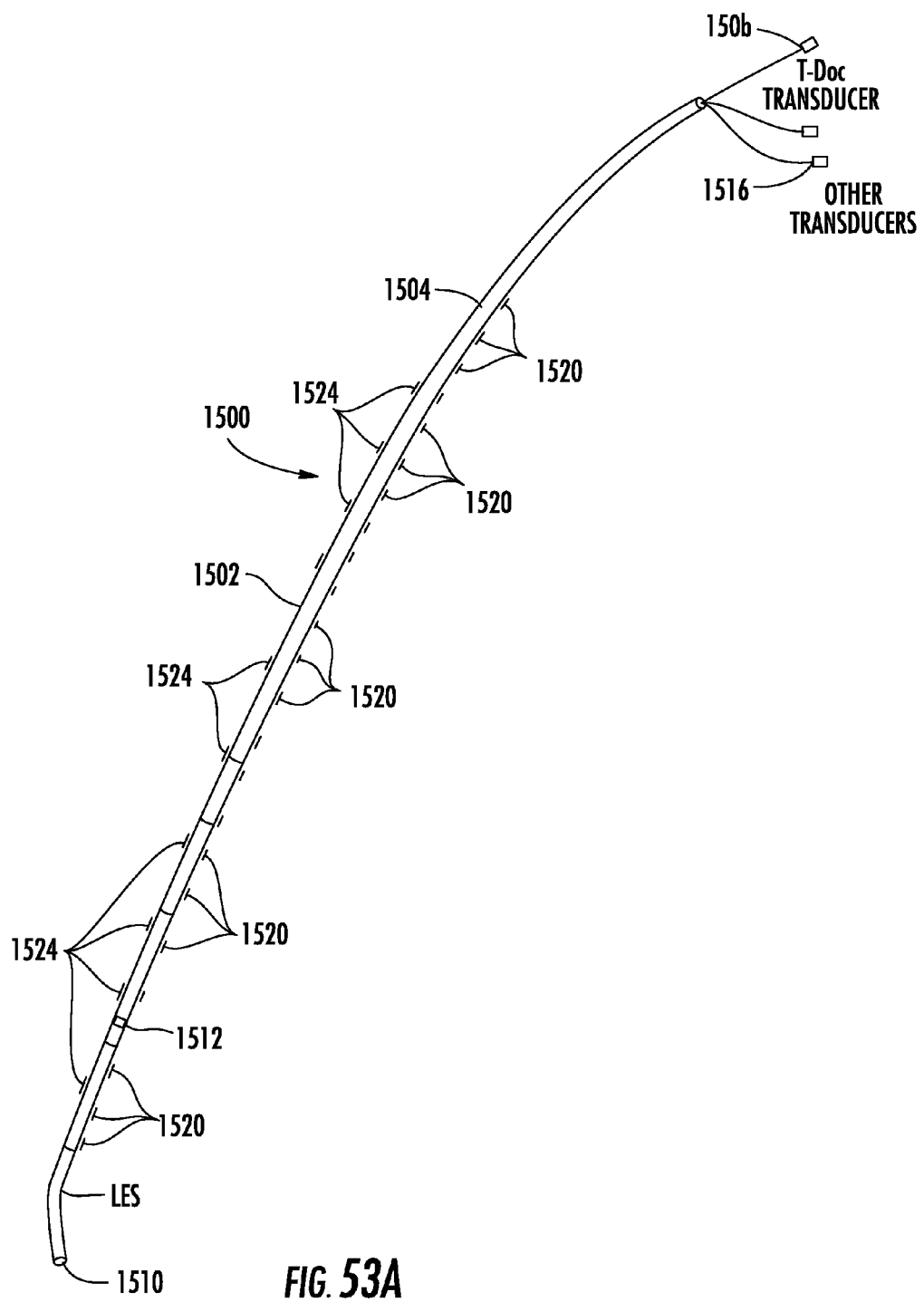
FIG. 53 is a plan view of a catheter that can assess the severity of reflux and compare a response of the involuntary reflex cough test and magnitude in accordance with a non-limiting example.

FIG. 53 shows a catheter 1500 as a device used in a method for diagnosing reflux during an involuntary event such as the involuntary reflex cough test. As illustrated, this catheter 1500 does not include any cuff as in previous embodiments shown in FIGS. 51a-51e and 52a-52g and includes a catheter body 1502 having a single lumen 1504 in this example with a T-DOC transducer 1506. It is formed as a small, semi-soft catheter. The adult size is about 6 French and the pediatric size is about 1-2 French. Two pressure sensor areas 1510, 1512 are formed for sensing pressure, for example, by using pressure transducers that are placed at the tip of the catheter and approximately 10-15 centimeters from the tip. Different types of sensors could be used and transducer leads 1516 could extend along the side or in the catheter to the end. The catheter could be an air charged catheter. In one example, the catheter is coated with a pH sensitive material 1520 that will change color when exposed to a pH less than about 4.0, indicating reflux. Measurement markings 1522 can be inserted or printed throughout the length of the catheter. In one example, the catheter is an air-charged (T-DOC) for pressure measurement, but other types of sensing mechanisms such as pressure sensors could be used as understood by those skilled in the art. Fiber optics could be used. The catheter is radio-opaque and includes such markings 1524, if radiologic placement is required and it can include in-patient and out-patient indications.

The catheter can operate as an NG/OG and is inserted orally or nasally into the esophagus and through the lower esophageal sphincter (LES) into the proximal stomach. Placement is measured from the lips (oral) or nares (nasal) to the TMJ (temporomandibular joint) to about four-finger breadths sub-xyphoid for adults.

The first sensor 1510 is located in the proximal stomach and can measure intra-gastric/intra-abdominal pressure. The second sensor 1512 is located approximately in the mid-to-lower esophagus and can measure intrathoracic pressure. A pressure grading can be over the LES. EMG information typically can be measured to simultaneously record changes in pressure and gradients. EMG can be measured from the paraspinals as described before. EMG sensors could be located at selected locations on the catheter for EMG measurement in some examples. The catheter can include color change indicia for the pH sensitive material to measure the height of refluxed, acidic gastric contents. The catheter can include pH sensors.

The catheter 1500 has the potential to identify SUI, assess Neurological airway protection (represented as one summated value) and SUI, and additionally assess bladder physiology and categorize any classification with a programmed algorithm in incontinent patients using this one small catheter with EMG measurement. Any inputs of different values can be to the handheld device as described.

When a different type of the same sized air charged gastric catheter is inserted from above, i.e. P.O. or NG, the device will measure Neurological airway for protection and assess gastro esophageal reflux from the involuntary maneuver epoch using the iRCT. This gastric catheter, which can also measure pressure below the LES, can predetermine gastric baseline pH and baseline esophageal pH above the LES at standard acid reflux levels already used in other pH testing. From that set up, with any catheters plugged into the handheld device (or eventually wirelessly to a wireless processing device), when given an iRCT, the handheld processing device will assess if reflux is present during the iRCT epoch, such as when it occurs during and/or after the epoch by pH change at these levels. Whether the patients are being treated with acid neutralizers or not, the determined baseline sets the ability to assess pH change when and where in the esophagus it occurs.

This approach will assess the severity of reflux compared to the response of the iRCT and magnitude of the involuntary cough epoch. Depending on the acid reflux elevation compared to the iRCT epoch, without inhalation tonicity protection, it could be instrumental in stratifying reflux severity and pivotal in directing treatment and demonstrating, with repeat testing, the efficacy of the treatment given. This device and process can be used for adult, pediatrics and newborn patients.

If gastro esophageal reflux occurs regularly, it is most likely secondary to an event that is a non-voluntary event, for example, a belch or involuntary cough, thus occurring without inhalation tonicity protection. The reflex acid stimulation to the lung could be from the distal esophagus reflex and very slow causing delayed cough, possibly involuntary coughs (possibly a vicious cycle) or irritable lung reactions causing inhalation and voluntary coughs. Regardless, they would not be temporally correlated by cough and reflux. This is reported in Chang, "An objective study of acid reflux and cough in children using an ambulatory pHmetry-cough logger" published online on Jun. 1, 2010 at Arch his Child. The cough sensor as described in Chang could not distinguish the different types of cough.

A question arises if an iRCT epoch when measured is temporarily related to reflux from the stomach during the epoch. It does not matter if there is a small distal esophageal reflux, which is supported by Irwin in the Abstract entitled, "The Cough Reflex and Its Relation to Gastroesophageal Reflux," *Am J Med*, March 2000, or a huge geyser airway laryngeal reflux that the ENT's describe as causing severe larynx damage over time because of acid burn. Both reflux events can hurt the lungs over time eventually.

Reflux should be diagnosed during the actual involuntary event when there is little or no inhalation tonicity protection. This will lead to appropriate treatment decisions to protect the lungs, i.e., acid suppression versus Fundoplication. The catheter device as described could be used for airway neuro measurement and bladder physiology, as well as mouth to stomach to prove reflux during an involuntary maneuver. In one example, this may require different types of catheters for different setups that all use the one handheld device for processing.

It should be understood that in the embodiments described above, the cuff operates similar to an umbrella. When the force of emesis hits it, the cuff will expand evenly without tearing or hurting the esophagus. The cuff material is typically a soft material. It should also be understood that this is advantageous because stroke could cause lower esophageal weakness and involuntary cough will not allow a patient to have inhalation protection in some instances. The cuff on the device provides such protection. The NG/OG tube as described with the cuff acts as an esophageal reflux protection device to protect a patient from the reflux caused by any weakness of the lower esophageal sphincter from both involuntary cough or muscle weakness from neurological injury or similar problems. When involuntary cough occurs, the stomach typically does not close down. The cough can cause reflux, which causes more cough as a vicious cycle. In some instances, it is possible have a Foley catheter and the smaller catheter tube as shown in FIG. 53 and leave the Foley and pull the catheter after a cough is measured for reflux. It is also possible that the Salem sump as described can be radio-opaque such as with a coating or a strip itself. The sump port itself could be radio-opaque to indicate where the port extends down into the stomach, such as about 6 centimeters in one example. Capillary pressure of the esophageal cuff can be about 7 to about 8 centimeters of water as a safety factor. The tube feeding channel, such as the main tube, would be a separate channel from the suction channel to ensure that the food is not mixed with any emesis.

The devices, catheter and functions as described above are advantageous. If there is an involuntary cough and reflux, a patient can be protected even if they are unconscious. For example, at times the stomach may be neutralized in a clinical setting and the protective device is advantageous to protect a patient from regurgitating their own stomach contents. Normally, when the stomach contents are acidic, and even if a patient is unconscious, if reflux occurs, a patient would normally cough it out and the reflux or emesis would not pass into the lungs. If the contents are neutral, however, they could discharge past the acid receptors and vocal cords, causing aspiration syndrome. The device and methodology therefore would test and prevent reflux damage and protect a patient's airway. The device can both feed and protect the patient.

Another advantageous aspect is that it is possible to accomplish involuntary cough and measure stomach pressure or intra-abdominal pressure during involuntary cough with the device as described. The involuntary maneuver as a diagnostic tool with the device can be used to diagnose reflux. When the device is pulled out of a patient, the configuration of the cuff allows the cuff to collapse.

The devices can be used to measure the cough epoch in conjunction with EMG measurements as noted in the flowcharts above. It is advantageous to diagnose the cough epoch and also diagnose severity of disease. The devices in conjunction with other measurements can be used to diagnose severity of reflux during the involuntary epoch and determine the best course of treatment. For example, if surgery is required or pelvic floor exercises or other treatment required. It allows a neuro anatomical finding. The devices can be used to measure pressure such as the abdominal pressure and reflux at the same time not only during the time of the reflux, but also determine the height of the reflux for severity.

It should be understood that a pH probe can be located in the stomach, one at the LES, one at the mid-esophageal region, and one at the superior esophageal region or any combination. pH sensors could be formed electrodes. The devices could have color changing indicia as a coating on all or part of the device to aid in measuring pH and reflux. The devices can include pH sensors and pressure sensors, for example, an air charged sensor. Fiber optics can be used as noted before. A device could be used to protect a patient's airway, feed the patient, administer medication, and vacuum or "suck up" contents and prevent aspiration in the stomach and esophagus. The device operates as a diagnostic tool in another example. The EMC shows a duration of the epoch or event and can be measured. It is typically measured from the paraspinals in an example. The device is used to diagnose GERD and prevent reflux in a non-limiting example.

It should be understood that the involuntary maneuver as described before can be used to test for damaged or malfunctioning abdominal-pelvic intrinsic sphincter. When either a physical or chemical substance stimulates receptors in the laryngeal mucosa, cough may result. Whether the cough is an involuntary reflex or a volitional response depends upon the quantity and type of stimulus. The laryngeal expiratory reflex (LER) is an involuntary, brainstem-mediated reflex. The vagus (X) nerve in one example mediates the afferent component of the LER, and the efferent component is conveyed via the vagus, phrenic, intercostal and abdominal nerves. The reflex cough test (RCT) is a cranial nerve examination assessing both the afferent sensory and efferent motor limbs of the laryngeal expiratory reflex. It is believed that the RCT is presently the only means to test the integrity of the LER.

The laryngeal receptors and afferent fibers of the internal branch of the superior laryngeal nerve are involved in the laryngeal expiratory reflex. Irritant receptors and Aδ afferent fibers appear to mediate laryngeal cough. The receptors of the laryngeal mucosa are well-innervated and sensitive to chemical stimuli. Fibers of the middle ramus of the internal branch of the superior laryngeal nerve (ibSLN) directly distribute to receptors in the central region of the vestibular aspect of the quadrangular membrane. The internal branch of the superior laryngeal nerve represents the afferent component of the laryngeal expiratory reflex (LER). A laryngeal evoked potential has been recorded from the ibSLN after inhalation of tartaric acid-induced cough (RCT). Bilateral anesthesia of the internal branch of the superior laryngeal nerve abolished the tartaric acid-induced laryngeal expiratory reflex.

Central processes of the superior laryngeal nerve (SLN) have been traced to clusters of neurons in the vicinity of the nucleus tractus solitarius (NTS, solitary nucleus). Although the internal morphology of the nucleus tractus solitarius in humans has been described, the central connections pertaining to the laryngeal expiratory reflex and voluntary cough have not been demonstrated in humans. SLN afferents terminate in the dorsal respiratory group (DRG). In cats, the respiratory related neurons are found in the DRG in the region of the nucleus tractus solitarius, and the ventral respiratory group (VRG) which is rostral and caudal to the obex and next to the nucleus ambiguus. The rostral VRG includes expiratory related neurons of the Bötzinger complex, located at the rostral end of the VRG. The Bötzinger complex is adjacent to the expiratory-related neurons of the retrofacial nucleus. The neurons project bilaterally to the ventrolateral region of the nucleus tractus solitarius, ventral respiratory group, phrenic nucleus, and spinal cord. The expiratory related neurons of the Bötzinger complex may have a role in integration of inhibitory influences from the laryngeal receptors and long, monosynaptic descending fibers from the Bötzinger complex may directly inhibit the motoneurons in the phrenic nucleus. The projection of this integrated information to the expiratory premotor neurons of the caudal VRG suggests a role in shaping the firing patterns of caudal VRG output.

Interneurons associated with the brainstem reticular formation probably convey sensory information from the NTS to the nucleus ambiguus, phrenic nucleus, dorsal motor nucleus of X, and medial motor cell column of the thoracic spinal cord. Efferent fibers from these nuclei course in the vagus nerve, phrenic nerve, and intercostal nerves, respectively, and produce the complex motor response described as cough.

Central Ascending Pathways. Sensory information originating from the laryngeal mucosa also projects to the cerebrum. Caudal and medial aspects of the nucleus tractus solitarius, including the retrofacial nucleus, project medullohypothalamic (solitarohypothalamic) fibers to the posterolateral hypothalamus, and also convey reciprocal connections with the paraventricular nucleus. In cats, the nucleus tractus solitarius projects to the lateral parabrachial nucleus and amygdala. Afferent information from the SLN may also reach the cerebral cortex in cats, and the forebrain in rats. The medial solitary nucleus, a recipient of many chemoreceptor afferents in cats, has reciprocal connections with the mesencephalic periaqueductal grey. In humans the nature of this pathway and how it may relate to the initiation of a volitional cough is unclear.

Central Descending Pathways. Although minor stimuli to the laryngeal mucosa may trigger the need for voluntary cough, laryngeal stimuli or sensory innervation are not necessary for the initiation of voluntary cough. Humans are capable of volitionally initiating or suppressing cough. Studies have reported disruption of the motor pattern involved in formulating a voluntary cough, a cortically mediated response in stroke subjects. Subjects, who had an infarct in the dominant cerebral hemisphere, were significantly more likely to demonstrate 'cough apraxia,' an inability to formulate the motor patterns and/or sequence involved in the VC response. In these subjects, the LER, as elicited by brisk inhalation of nebulized tartaric acid, was normal.

Descending influences from areas of the frontoparietal cortex and subcortical areas may modulate the laryngeal expiratory reflex or mediate the voluntary cough, Fibers from infralimbic and prelimbic regions of the medial frontal cortex terminate in the nucleus tractus solitarius in rats, bed nucleus of the stria terminalis, and amygdala in cats. In cats, efferent fibers from the cortical nucleus of amygdala descend to the hypothalamic ventromedial nucleus via the stria terminalis to the nucleus tractus solitarius and the nucleus ambiguus in the medulla. This pathway is responsible for production of spasmodic expiratory response like cough. Similar connections from the cortex, amygdala, and hypothalamus to the NTS have been reported in rats. In rats, the prefrontal cortical fibers descend through the cerebral peduncle and pyramidal tract to finally terminate in the dorsal NTS, a region that receives substantial vagal and glossopharyngeal afferent input. Descending fibers from subcortical areas such as the amygdala, bed nucleus of the stria terminalis, and the paraventricular, arcuate and posterolateral nuclei of the hypothalamus, course through the mesencephalic and pontine tegmentum to terminate principally in the ventral NTS. A case report indicated the inability to voluntarily cough following a left cerebrovascular stroke. This report suggested a possible role of amygdalo-hypothalamo-reticular efferents in humans. Studies in cats indicate that neuronal functions associated with respiration and respiratory-related activities can be suppressed by descending influences from periaqueductal gray matter and nucleus raphe magnus. The function of these descending fibers, and how they might relate to a cortically mediated voluntary cough pathway in humans requires further investigation.

Interneurons associated with the brainstem reticular formation may convey descending information from the cortical and subcortical regions to the nucleus ambiguus, phrenic nucleus, and medial motor cell column of the thoracic spinal cord. Efferent fibers from these nuclei course in the vagus nerve, phrenic nerve, and intercostal nerves, respectively, and produce the complex motor response described as cough. In humans the role of descending fibers in the voluntary cough pathway in modulating the laryngeal expiratory reflex or mediating the voluntary cough awaits further studies.

Figure 53B:
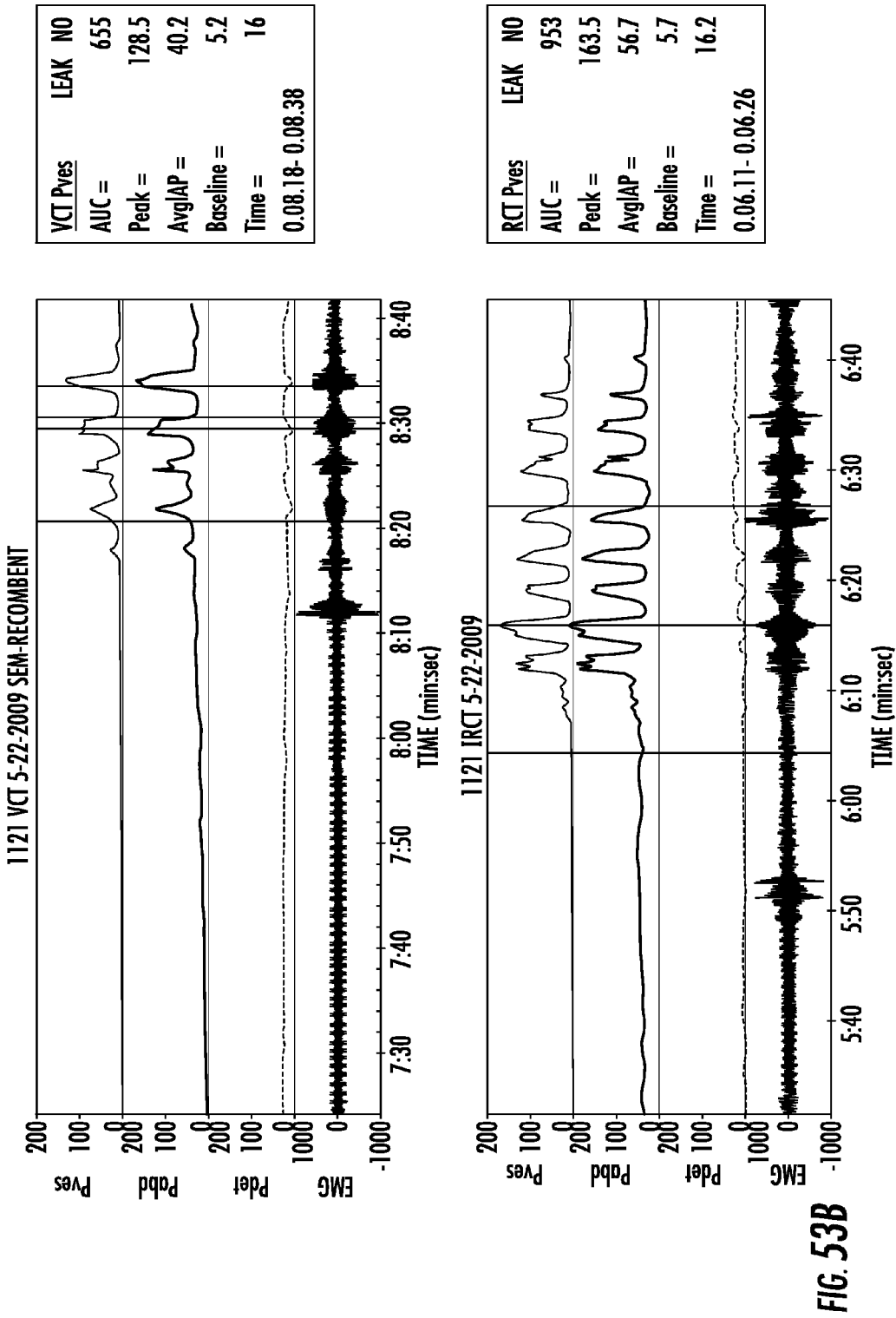

FIG. 53b is a urodynamic tracing of a series of voluntary cough (VC) in a normal female subject with a urinary bladder filled with 200 ml of saline. There is no evidence of SUI, i.e., urine leakage, during the series of VC or the five cough (C5) iRCT stimulus. With the iRCT the entire episode, which can have a duration of 14.8 seconds, during which there is no significant inhalation or lung inflation to activate US and LES tonicity. This subject is continent without the facilitatory effect of increased tonicity associated with lung inflation.

Figure 53C:
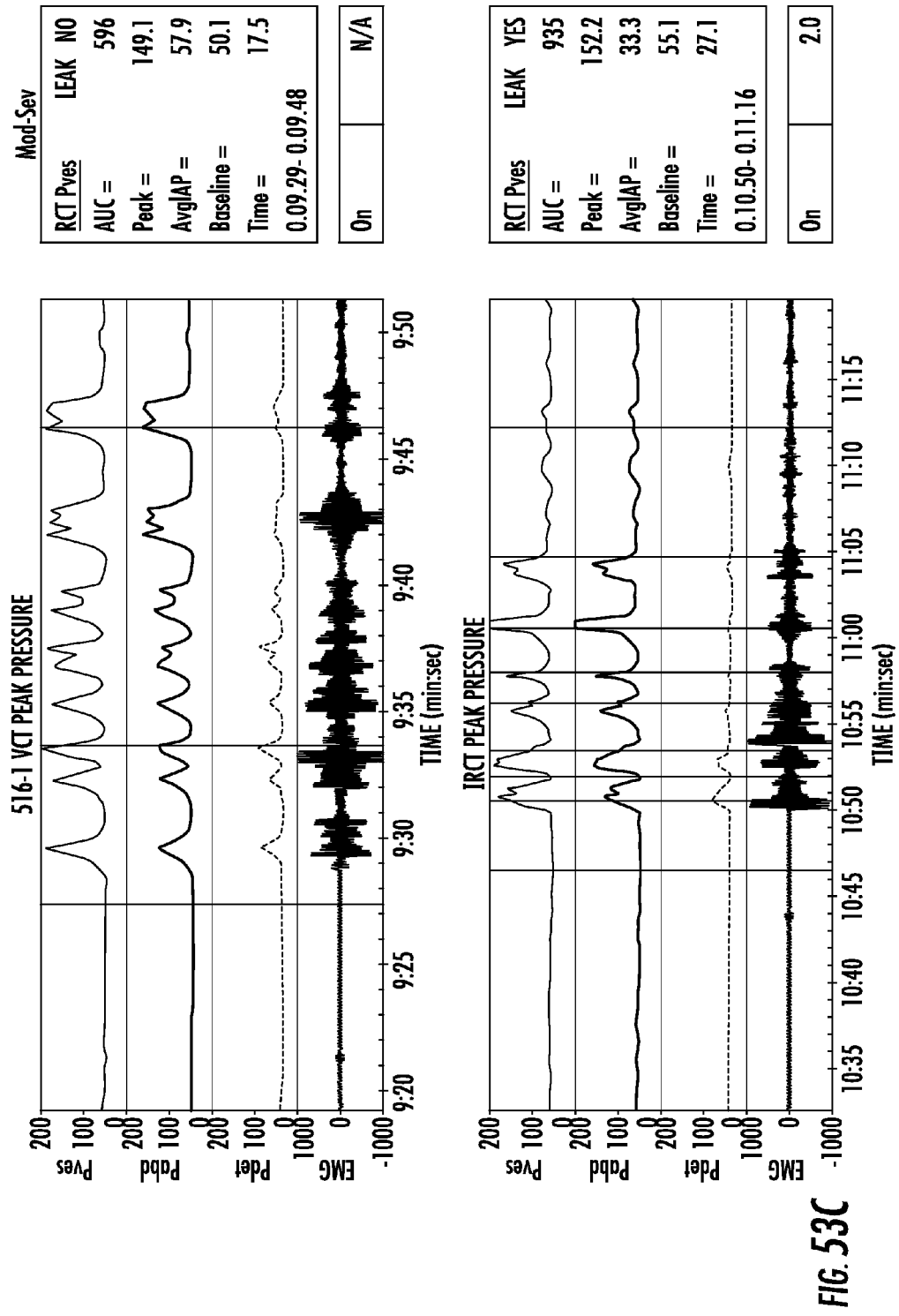

FIG. 53C is a urodynamic tracing of a series of VC in a female subject who has moderate/severe SUI. VC did not elicit urinary incontinence despite the series of vigorous individual consecutive inhalation VC efforts. The iRCT caused immediate SUI with multiple leakages (red lines) during the 26 second involuntary event.

Abdominal and pelvic floor musculature (PFM) are co-activated during voluntary cough response (VCR) and involuntary reflex maneuvers tasks. The abdominal activation may displace the bladder neck, but this effect may be different between the structurally and functionally different muscles of the abdominal wall (internal abdominal oblique (IAO), external abdominal oblique (OE), rectus abdominis (RA) and transversus abdominis (TA)). Furthermore, the timing of the abdominal and PFM contraction in relation to the IAP can be important.

Although continence may be dependent on the net effect of each of these factors, no study has comprehensively investigated multiple elements simultaneously or the potential of subtle differences in coordinative mechanisms.

Voluntary cough (VC) and the laryngeal expiratory reflex (LER) have distinctly different neurophysiological and pharmacological mechanisms. Voluntary cough (VC) is classically defined as a cough that starts with an inspiration due to contraction of the diaphragm followed by brief glottal closure, contraction of the external abdominal oblique muscles, and subsequent glottal opening for the expiratory phase of the VC. VC is a cortically mediated response that requires appropriate sensory and motor functions, praxis and cognition. As the lungs inflate during inspiration there is a corresponding in the tonicity of both the urethral sphincter (US) and lower esophageal sphincter (LES). It is a planned, learned motor event. Stroke subjects who had lesions involving the dominant cerebral hemisphere demonstrated cough apraxia—an inability to formulate the motor sequence associated with VC. Asking an obtunded, intubated or deaf patient to perform a VC poses obvious clinical difficulties. A videofluoroscopic study showed the depression of the diaphragm associated with inspiration following by an upward diaphragmatic displacement. VC did not displace (elevate) the diaphragm as much as reflex cough, which displaced the diaphragm to mid-sternal levels.

The laryngeal expiratory reflex (LER) is normally triggered when food, fluid or secretions enter the larynx during swallowing or inspiration. Reflex cough can be triggered by aspiration of food or fluid during inspiration, acid reflux stimulation of laryngeal receptors or post-nasal drip into the larynx or laryngeal inflammation or infection.

The LER is a brainstem-mediated reflex that initiates an immediate series of expiratory coughs without an inspiratory phase. The LER is the involuntary reflex that neurologically protects the upper airway from noxious aspirants and, as such, it has a critical neurological function, which is unique to humans. An induced reflex cough test (iRCT), using a nebulized 20% solution of a mild chemoirritant, has been used to elicit a LER in subjects. The iRCT is characterized by a series of, at least, five expiratory reflex coughs (C5) with a 17 ms latency to the EAO muscles. During the LER, contraction of the EAO muscles compress the abdominal viscera, which push against the relaxed diaphragm superiorly for the expiratory phase of VC and push inferiorly against the urinary bladder and rectum, with a concomitant increase in intra-abdominal pressure (IAP). Quantitative IAP measurements during VC and reflex cough have been reported using a strain gauge pressure transurethral bladder catheter and rectal catheter, and multi-channel urodynamic analysis of pressure changes.

Since reflex cough is expiratory and is not preceded by diaphragmatic contraction associated with inspiration, the iRCT indicates the native tonicity and function of the US and LES, which is critical in the diagnosis of SUI and GERDS, respectively. Animal models cannot adequately study VC and the LER, since the animals are surgically decerebrated and intubated.

During coughing, the urethral sphincter (US) and lower esophageal sphincter (LES) are tonically closed to prevent urinary incontinence (UI) or gastroesophageal reflux. During VC, the inhalation precedes the expiratory phase of VC and, like most cortically mediated motor events, causes a preparatory increase in US and LES muscle tone. Since the iRCT does not have an inspiratory phase, the US and LES muscle tone remains in its native state of tonic closure. Patients who have stress UI (SUI) complain that they leak urine when they (reflex) cough, sneeze, exercise or laugh. The patient often carefully performs VC and the patient's anticipation may trigger urethral reflexes ("guarding") that may increase US tone, if physically and neurologically possible. The result may be favorable to the patient (no leak), but represents a suboptimal test for SUI. If the patient demonstrates SUI during VC, they may have an intrinsic sphincter deficiency (ISD) involving the US, control circuits or structure.

A normal reflex cough, such as cough triggered by a brief aspiration of a food particle, would normally trigger the LER and a concomitant increase in IAP. If a patient has ISD involving the LES, then the increase the IAP associated with a C5 series of LER coughs, which may have a duration of 15 seconds or more without an inspiration, may cause reflux of gastric acid into the lower esophagus. The construct in this scenario is that normal reflex coughing, perhaps compounded by a high BMI, may be the initial stimulus for subsequent coughing with acid reflux into the hypopharynx or larynx. If so, iRCT would be clinically useful is testing the LES.

SUI and GERDS are two types of intrinsic sphincter deficiency (ISD). The iRCT may be clinically useful in improved evaluation of LES function and a more realistic assessment of SUI.

Figure 54A:
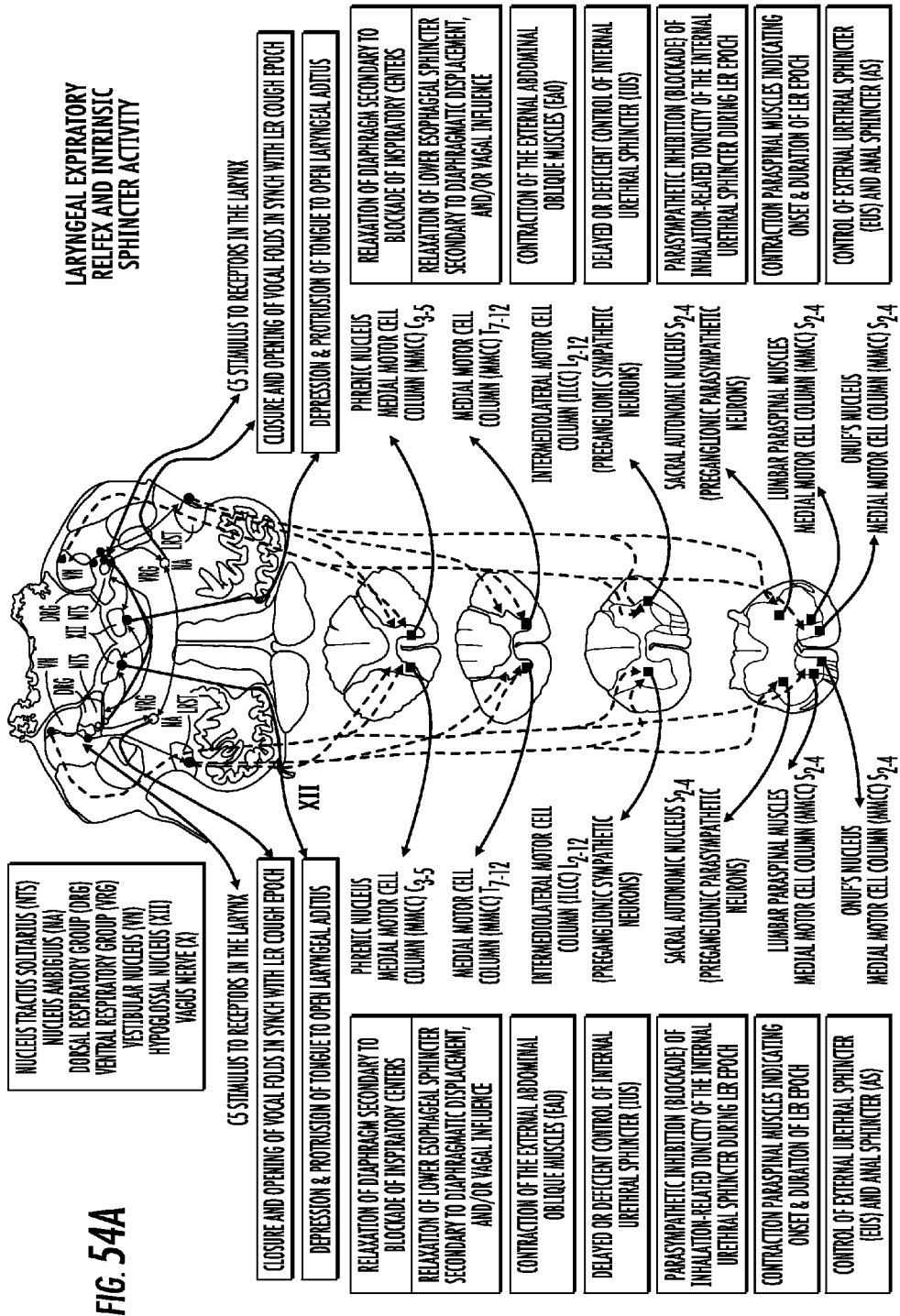

FIG. 54a is a diagram detailing what occurs during the LER (Laryngeal Expiratory Reflex) and Intrinsic Sphincter Activity). This diagram shows a schematic of the LER neural circuits. FIG. 54b illustrates Voluntary Cough (VC) pathways. There are some key points regarding VC, micturition, and the brainstem mediated LER. Voluntary Cough (VC) is a cortically mediated, conditioned (learning) response. It is not a reflex. It is a learned or developed neuromuscular sequence, which can be disrupted or absent in some stroke patients. All VC events begin with an inspiration (inhalation), which has a premotor effect on the muscle tone of the abdominal and pelvic sphincters. It can also be (and often is) attenuated by the subject during the urodynamic exam, since the subject empirically knows the "level" of effort that would produce a leak. The VC cortically medicated micturition and LER are not the same circuits and share only some motor nuclei, but probably not the same terminations in these nuclei. VC does not use neurons in the nucleus tractus solitarii (NTS), the principal sensory nucleus that mediates the LER patterned reflex pattern. The LER has a specific central pattern generator in the medulla that is programmed (wired) to elicit a rapid neural protective reflex, which:

(1) clears the upper airway of potential aspirants; and (2) closes abdominal and pelvic sphincters. This is a symmetrical and synchronous reflex to the associated muscle. However, the smooth muscle of the internal urethral sphincter is quite slow compared to the striated muscles of the EUS. This histological difference along with urinary bladder structural issues, patient demographics, and the possibility of dyssynchronous firing of the bilateral LER circuits (a useful test in itself) may also be contributing factors. Nevertheless, the test appears to be a very reliable indicator as to the functional integrity of the CNS component of the LES circuit and, more on point, the integrity of the external urethral sphincter (EUS). If the EUS fails, SUI is almost immediate. If the EUS is intact and functioning correctly, SUI is an unlikely issue. This scenario relates to the evolution of upright posture, the displacement of the urinary bladder into the pelvis in the late teens, and a social need for volitional control, except in situations where there is sphincter deficiency and an abrupt onset of intra-abdominal pressure).

The LER patterned reflex circuit is associated with a noxious stimulus (food or fluid aspiration) or a clinical test (such as the iRCT that mimetics the effect of a noxious stimulus) that triggers supraglottic receptors (superior to the vocal folds) in the larynx without a preceding inspiration. This last point plays a critical role in the LER circuit and its role in continence.

During the LER cough epoch, it is not possible to inhale (inspire), which may be due to inhibition or blockage of the phrenic nucleus or an effect on the inspiratory center in the brainstem, or both. Nevertheless, the subject cannot inhale during a properly administered iRCT. Without an inspiration (inhalation), the "presets" for the urethral sphincters appear to be quite different as shown on clinical trials.

The LER circuit involved a restricted region of the NTS and adjacent neuronal clusters. It has extensive reciprocal connections, which interconnect LER circuit neuronal groups with rapid descending pathways in the lateral reticulospinal tract (bulbospinal tract) and lateral vestibulospinal tract. These tracts have strong influences on autonomic nuclei in the spinal cord and motor nuclei to axial musculature.

Figure 55:
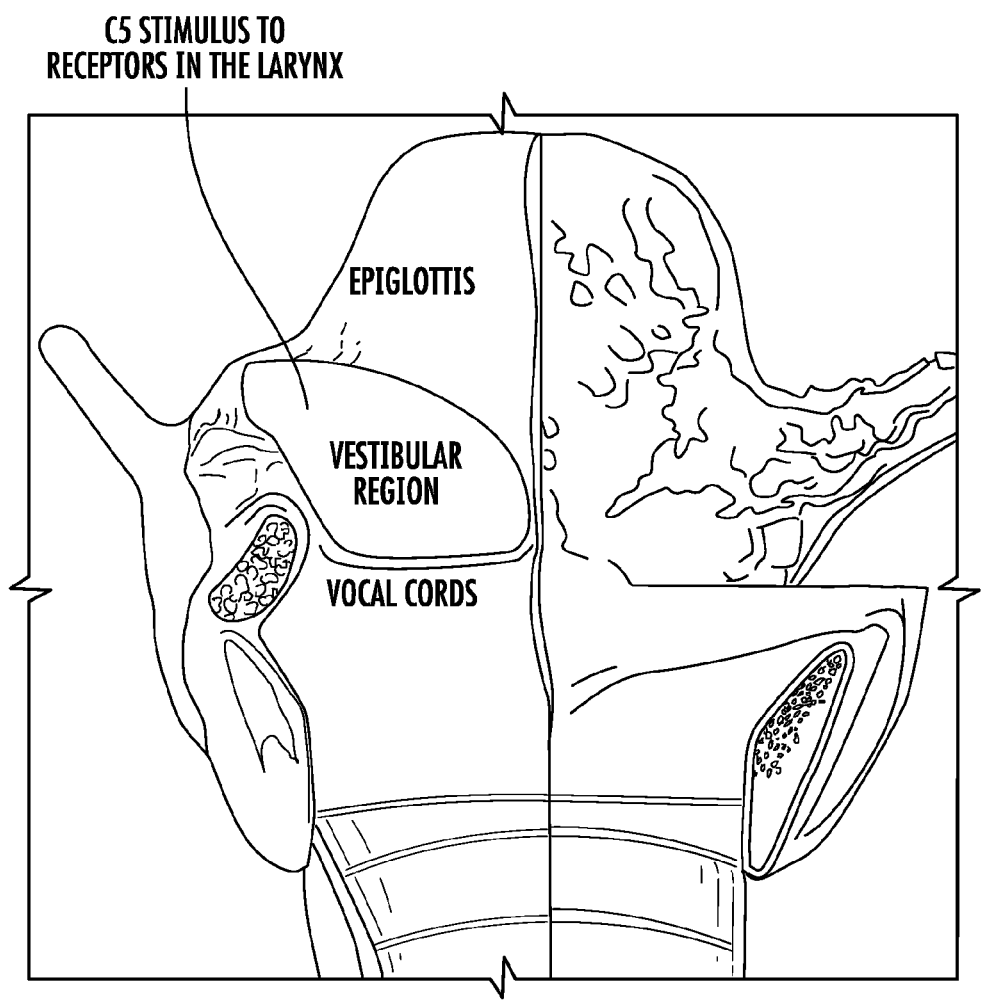

FIG. 55 is an enlarged view of the epiglottis, vocal cords and vestibular region in which the C5 stimulus is received to receptors in the larynx and the closure and opening of vocal folds are in synchronization with the LER cough epoch.

FIG. 56 is a diagram showing the diaphragm and the relaxation of the lower esophageal sphincter (LES) that occurs during the LER.

Figure 57:
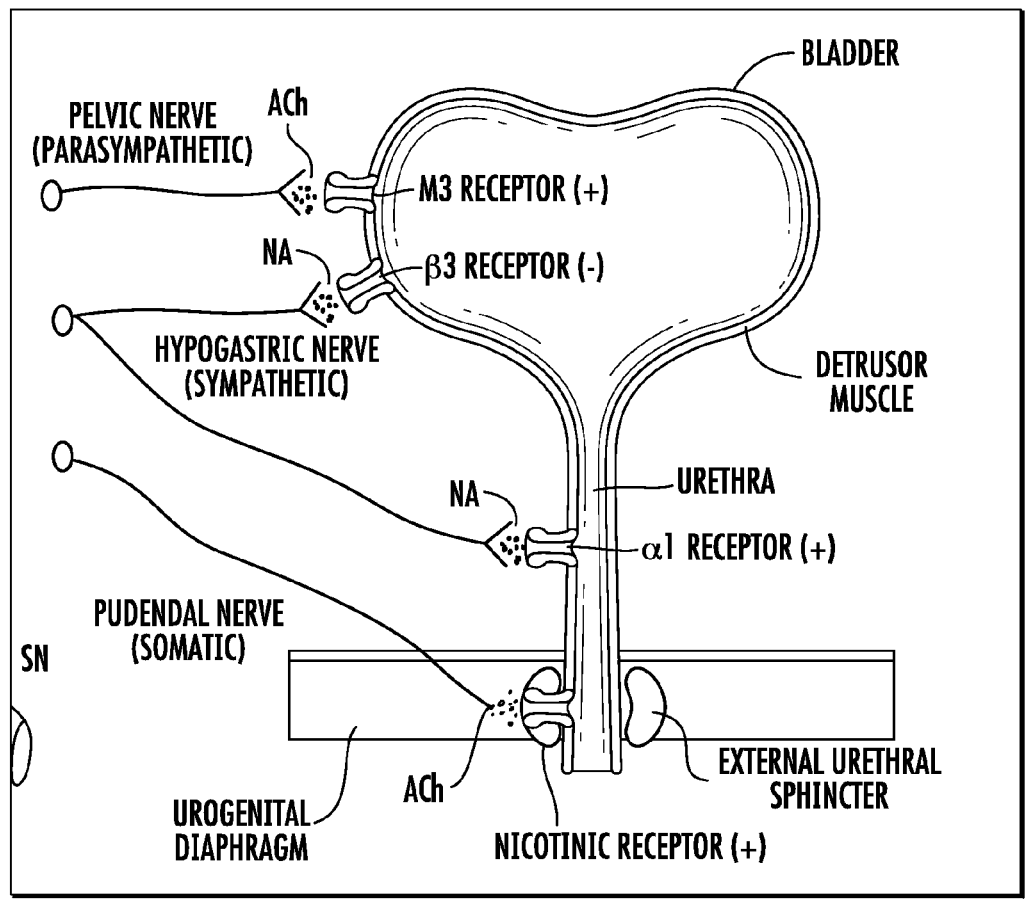

FIG. 57 is a diagram showing the bladder and other components and various nerves for purposes of illustration.

Figure 58:
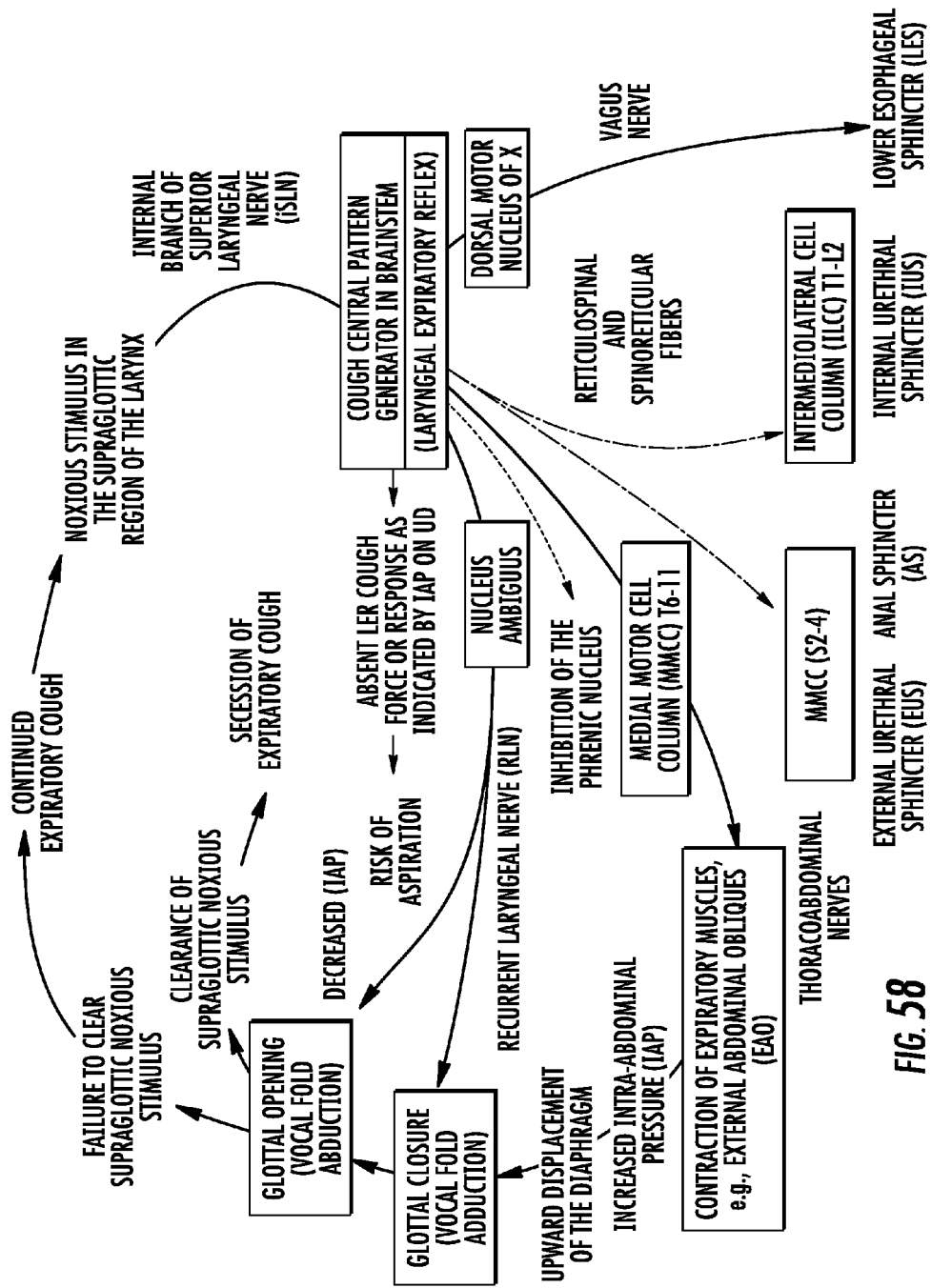

FIG. 58 shows a suggested sequence for the LER.

This application is related to copending patent applications entitled, "ORAL-ESOPHAGEAL-GASTRIC DEVICE WITH ESOPHAGEAL CUFF TO REDUCE GASTRIC REFLUX AND/OR EMESIS," and "ORAL-ESOPHAGEAL-GASTRIC DEVICE TO DIAGNOSE REFLUX AND/OR EMESIS," which are filed on the same date and by the same assignee and inventors, the disclosures which are hereby incorporated by reference.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A system of diagnosing a patient for a physiological abnormality while protecting their airway, comprising:
    an esophageal airway protection device that comprises an elongate device body having a distal end for insertion into the stomach through the esophagus and a proximal end, and having a main lumen extending the length of the device and an inflatable esophageal cuff carried by the device body mid-esophagus and an inflation lumen formed within the device body and connecting the inflatable esophageal cuff through which the esophageal cuff is inflated and deflated, wherein upon inflation of said esophageal cuff, emesis and/or reflux is blocked from passing out of the stomach past the esophageal cuff positioned mid-esophagus to protect a patient's airway during an involuntary cough event;
    a nebulizer lumen extending along the device body and comprising a port through which medication is delivered for administrating the involuntary cough event, wherein said esophageal cuff protects the airway during the involuntary cough event;
    at least one electromyogram (EMG) pad configured to obtain an EMG from involuntary cough activated paraspinal muscles; and
    a processing device configured to receive the EMG and process the EMG to determine a physiological abnormality.

2. The system according to claim 1, and further comprising a nebulizer venturi connecting the nebulizer lumen and configured to deliver nebulized medication around the device body.

3. The system according to claim 1, and further comprising at least one pressure sensor located on the device body and configured to measure intra-abdominal pressure (IAP), wherein said processing device receives the IAP and correlates the IAP and EMG and involuntary reflex cough epoch.

4. The system according to claim 3, wherein said at least one pressure sensor comprises a pressure transducer and a transducer lead connecting the pressure transducer.

5. The system according to claim 3, and further comprising at least one pH sensor carried by the device body, and said processing device receives pH measurements and processes same with EMG and IAP.

6. The system according to claim 3, wherein the said processing device comprises a portable handheld device comprising, a housing configured for handheld use; at least one interface carried by the housing and configured to receive the pressure measurements obtained during the involuntary cough reflex test; and a processor carried by the housing and connected to the interface and configured to receive the IAP and EMG.

7. The system according to claim 1, and further comprising a sump port at the distal end and sump lumen formed the length of the device body and configured for venting gas and preventing adherence of the device against the gastric wall.

8. The system according to claim 1, wherein the esophageal cuff is radio-opaque to aid in placing the esophageal cuff at a desired location within the esophagus.

9. A method of diagnosing a patient for a physiological abnormality while protecting their airway, comprising:
inducing an involuntary reflex cough event within a patient;
protecting the patient's airway from any reflux or emesis that results from the involuntary reflex cough event by blocking the reflux or emesis from rising into the patient's airway using an esophageal airway protection device that comprises an elongate device body having a distal end that is inserted into the stomach through the esophagus and a proximal end, and having a main lumen extending the length of the device and an inflatable esophageal cuff carried by the device body mid-esophagus, wherein upon inflation of said esophageal cuff, emesis and/or reflux is blocked from passing out of the stomach past the esophageal cuff positioned mid-esophagus to protect a patient's airway; and
obtaining an electromyogram (EMG) from involuntary cough activated paraspinal muscles and processing the EMG within a processing device to determine a physiological abnormality.

10. The method according to claim 9, and further comprising delivering medication to administer the involuntary reflex cough test through a nebulizer lumen extending along the device body.

11. The method according to claim 9, and further comprising measuring intra-abdominal pressure (IAP) and correlating the EMG and IAP within a processing device to diagnose a physiological abnormality.

12. The method according to claim 11, wherein the said processing device comprises a portable handheld device comprising, a housing configured for handheld use; at least one interface carried by the housing and configured to receive the pressure measurements obtained during the involuntary cough reflex test; and a processor carried by the housing and connected to the interface and configured to receive the IAP and EMG.

13. The method according to claim 12, wherein the esophageal cuff is radio-opaque to aid in placing the esophageal cuff at a desired location within the esophagus.

14. The method according to claim 12, and further comprising suctioning reflux or emesis through suction holes that communicate with a suction lumen formed within the device body.

15. The method according to claim 12, and further comprising venting gases from the stomach through a sump port connected to a sump lumen.

16. The method according to claim 12, and further comprising inflating the esophageal cuff through an inflation lumen that communicates with the esophageal cuff.

* * * * *